(12) United States Patent
Xu et al.

(10) Patent No.: US 10,471,124 B2
(45) Date of Patent: Nov. 12, 2019

(54) PROTEINACEOUS HETERODIMER AND USE THEREOF

(71) Applicant: DINGFU BIOTARGET CO., LTD., Suzhou, Jiangsu (CN)

(72) Inventors: Ting Xu, Jiangsu (CN); Yan Luan, Jiangsu (CN); Jianjian Peng, Jiangsu (CN); Shuli Ma, Jiangsu (CN); Meng Zhao, Jiangsu (CN); Xiaoxiao Wang, Jiangsu (CN); Hui Ma, Jiangsu (CN); Shilong Fu, Jiangsu (CN); Xiaolong Pan, Jiangsu (CN); Shanshan Ning, Jiangsu (CN)

(73) Assignee: DINGFU BIOTARGET CO., LTD., Jiangsu (CN)

( * ) Notice: Subject to any disclaimer, the term of this patent is extended or adjusted under 35 U.S.C. 154(b) by 0 days.

(21) Appl. No.: 15/528,909

(22) PCT Filed: Nov. 10, 2015

(86) PCT No.: PCT/CN2015/094235
§ 371 (c)(1),
(2) Date: May 23, 2017

(87) PCT Pub. No.: WO2016/082677
PCT Pub. Date: Jun. 2, 2016

(65) Prior Publication Data
US 2017/0340708 A1 Nov. 30, 2017

(30) Foreign Application Priority Data
Nov. 24, 2014 (CN) .......................... 2014 1 0681422

(51) Int. Cl.
| | | |
|---|---|---|
| A61K 38/19 | (2006.01) | |
| C07K 14/54 | (2006.01) | |
| C07K 14/56 | (2006.01) | |
| C07K 14/565 | (2006.01) | |
| C07K 16/28 | (2006.01) | |
| A61K 38/00 | (2006.01) | |
| C07K 19/00 | (2006.01) | |
| C12N 15/62 | (2006.01) | |
| C12N 15/63 | (2006.01) | |

(52) U.S. Cl.
CPC .......... *A61K 38/19* (2013.01); *C07K 14/5428* (2013.01); *C07K 14/56* (2013.01); *C07K 14/565* (2013.01); *C07K 16/2863* (2013.01); *C12N 15/62* (2013.01); *C12N 15/63* (2013.01); *A61K 38/00* (2013.01); *C07K 19/00* (2013.01); *C07K 2317/92* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 2002/0193569 A1 | 12/2002 | Hanna |
| 2014/0050660 A1 | 2/2014 | Chang et al. |

FOREIGN PATENT DOCUMENTS

| | | | |
|---|---|---|---|
| CN | 1206350 A | 1/1999 | |
| CN | 104403004 A | 3/2015 | |
| WO | 0006605 A2 | 2/2000 | |
| WO | 03/092737 A1 | 11/2003 | |
| WO | 2006/127757 A3 | 3/2007 | |
| WO | WO2007128563 | * 11/2007 | .......... C07K 14/535 |
| WO | 2009/039409 A1 | 3/2009 | |
| WO | WO2013070076 | * 5/2013 | ............. C07K 14/54 |
| WO | WO2013100702 | * 7/2013 | ............. C07K 16/28 |
| WO | 2014164427 A1 | 10/2014 | |

OTHER PUBLICATIONS

Ortiz-Sanchez et al. Antibody-cytokine fusion proteins: Applications in cancer therapy. Expert opinion in biological therapy. 8, 609-632, 2008. (Year: 2008).*
European Search Report from related application 15862694.5-1120/3227342 PCT/CN2015094235.

* cited by examiner

*Primary Examiner* — Elly-Gerald Stoica
(74) *Attorney, Agent, or Firm* — W&C IP

(57) ABSTRACT

The present disclosure provides proteinaceous heterodimers, pharmaceutical compositions, medicaments and/or kits comprising the proteinaceous heterodimers, methods for producing the proteinaceous heterodimers, and uses thereof.

3 Claims, 31 Drawing Sheets
Specification includes a Sequence Listing.

PROTEINACEOUS HETERODIMER AND USE THEREOF

BACKGROUND

Although immune responses against tumor antigens can be detected (Disis et al. (1997) J. Clin. Oncol. 15: 3363-3367), malignant cells causing diseases often fail to elicit an immune response that leads to rejection. Studies have demonstrated that it is possible to enhance the immunogenicity of tumor cells by introducing immunoregulatory molecules such as cytokines and costimulatory molecules into them; however, eradication of residual cancer cells may require the targeting of widely scattered micrometastatic tumor deposits that are not accessible to direct gene transfer. In addition, the expression and stability of the immunoregulatory molecules introduced are often far from satisfactory. Immunoregulators, such as cytokines, produced by cells of the immune system can, directly or indirectly, activate the cells of the adaptive immune response and can play an important role in eliciting protective antitumor immunity. The innate immune system can be triggered by bacterial products or "danger" signals that lead to the release of proinflammatory cytokines, such as IFN-α, TNF-α, and interleukins.

Multiple studies have shown that immunoregulators may be useful in exerting antitumor effects in both animal models and cancer patients. However, short half-life and systemic toxicity related with application of the immunoregulators have greatly limited their usage. In CN200880117225.8, a chimeric construct comprising an interferon attached to the c-terminus of an antibody targeting a tumor associated antigen has been described. However, fusion proteins expressed from such a chimeric construct are typically very unstable in vivo, and the expression yield thereof is typically not high enough for industrial-scale production.

SUMMARY

As such, there is a considerable need for targeted expression of immunoregulators, which could be produced with relatively high yield at industrial-scale and would have a relatively long half-life in vivo to be useful in treating disorders or diseases related with hyper proliferation of cells and/or tissues, e.g., various neoplasms, different types of cancer, and/or tumors.

The present disclosure addresses such a need and provides related advantages as well. The present disclosure encompasses proteinaceous heterodimers useful in inhibiting tumor growth, and compositions, medicaments and/or kits comprising the proteinaceous heterodimers. The disclosure also provides methods for the production of the proteinaceous heterodimers, as well as pharmaceutical uses of the proteinaceous heterodimers in inhibiting tumor growth, including but not limited to treatment of cancers.

In some aspects, the proteinaceous heterodimers of the present disclosure have significant anti-tumor activity. In some aspects, the proteinaceous heterodimers of the present disclosure have high expression yield. In some aspects, the proteinaceous heterodimers of the present disclosure have long in vivo half-life. In some aspects, the proteinaceous heterodimers of the present disclosure are particularly suitable for large scale industrial production.

In one aspect, the present disclosure provides proteinaceous heterodimers. In some embodiments, one member of the heterodimer comprises (i) a light chain and (ii) a heavy chain complexed to form a targeting moiety exhibiting binding specificity to a tumor antigen; and one other member of the heterodimer comprises a polypeptide comprising, from N-terminus to C-terminus, an immunoregulator fused to a heavy chain fragment, wherein the heavy chain fragment complexes with the heavy chain (ii) to form the heterodimer.

In some embodiments, the targeting moiety specifically binds to a tumor antigen that is a membrane protein. In some embodiments, the targeting moiety specifically binds to a tumor antigen that is a cell surface receptor. For example, the targeting moiety may specifically bind to a tumor antigen that is a cell surface receptor selected from the group consisting of transforming growth factor receptor (TGFR), epidermal growth factor receptor (EGFR), insulin-like growth factor receptor (IGFR), fibroblast growth factor receptor (FGFR) heregulin receptor, platelet-derived growth factor receptor (PDGFR), vascular endothelial growth factor receptor (VEGFR), and hypoxia inducible factor receptor (HIFR).

In some embodiments, the targeting moiety specifically binds to a tumor antigen that is a growth factor, hormone, or an extracellular matrix molecule. For example, the targeting moiety may specifically bind to a tumor antigen that is a growth factor, hormone, or an extracellular matrix molecule selected from the group consisting of transforming growth factor (TGF), epidermal growth factor (EGF), insulin-like growth factor (IGF), fibroblast growth factor (FGF), heregulin, platelet-derived growth factor (PDGF), vascular endothelial growth factor (VEGF), hypoxia inducible factor (HIF), c-Met, human chorionic gonadotropin, gonadotropin releasing hormone, androgen, estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, leptin, thrombopoietin, angiotensinogen, IL-1. IL-2, IL-3, IL-4, IL-5, IL-6, IL-7, IL-8, IL-9, IL-10, IL-II, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, collagen, elastin, biglycan, decorin, lumican, versican, perlecan, C-reactive protein, ApoE, and laminins.

In some embodiments, the targeting moiety specifically binds to a tumor antigen selected from the group consisting of EGFR mutant, HER2/neu, HER3, HER4, CD4, CD19, CD20, CD22, CD29b, CD30, CD33, CD37, CD38, CD52, CD70, CD79b, CD123, CD138, CD200, CD276, CXCR3, CXCR5, CCR3, CCR4, CCR9, CRTH2, PMCH, endoplasmin, CS1, CEA, mesothelin, G250, MUC1, MUC16, PSMA, ADAM17, EPCAM, EphA2, MCSP, GPA33, NAPi2b, STEAP1, CEACAM1, CEACAM5, GPNMB and TROP. For example, the targeting moiety may specifically bind to EGFR, an EGFR mutant, or HER2/neu. In some embodiments, the (i) light chain of the targeting moiety contains complementarity determining regions (CDRs) comprising an amino acid sequence that is at least 60%, 70%, 75%, 80%, 85%, 90%, 95%, 96%, 97%, 98%, 99% or 100% identical to that comprised in corresponding CDRs of a light chain of an antibody specifically directed to a tumor antigen. In some embodiments, the (i) light chain of the targeting moiety contains a variable region comprising an amino acid sequence that is at least 60%, 70%, 75%, 80%, 85%, 90%, 95%, 96%, 97%, 98%, 99% or 100% identical to that comprised in a variable region of a light chain of an antibody specifically directed to a tumor antigen.

In some embodiments, the (i) light chain of the targeting moiety comprises an amino acid sequence that is at least 60%, 70%, 75%, 80%, 85%, 90%, 95%, 96%, 97%, 98%, 99% or 100% identical to that comprised in a light chain of an antibody specifically directed to a tumor antigen. In some embodiments, the (ii) heavy chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of an antibody specifically directed to a tumor antigen. In some embodiments, the (ii) heavy chain of the targeting moiety contains a variable region comprising an amino acid sequence that is at least 60%, 70%, 75%, 80%, 85%, 90%, 95%, 96%, 97%, 98%, 99% or 100% identical to that comprised in a variable region of a heavy chain of an antibody specifically directed to a tumor antigen.

In some embodiments, the (ii) heavy chain of the targeting moiety comprises an amino acid sequence that is at least 60%, 70%, 75%, 80%, 85%, 90%, 95%, 96%, 97%, 98%, 99% or 100% identical to that comprised in a heavy chain of an antibody specifically directed to a tumor antigen. In some embodiments, the (i) light chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a light chain of an antibody specifically directed to a tumor antigen; and the (ii) heavy chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of the antibody specifically directed to a tumor antigen. In some embodiments, the (i) light chain of the targeting moiety contains a variable region comprising an amino acid sequence that is at least 60%, 70%, 75%, 80%, 85%, 90%, 95%, 96%, 97%, 98%, 99% or 100% identical to that comprised in a variable region of a light chain of an antibody specifically directed to a tumor antigen; and wherein the (ii) heavy chain of the targeting moiety contains a variable region comprising an amino acid sequence that is at least 60%, 70%, 75%, 80%, 85%, 90%, 95%, 96%, 97%, 98%, 99% or 100% identical to that comprised in a variable region of a heavy chain of the antibody specifically directed to a tumor antigen.

In some embodiments, the (i) light chain of the targeting moiety contains an amino acid sequence that is at least 60%, 70%, 75%, 80%, 85%, 90%, 95%, 96%, 97%, 98%, 99% or 100% identical to that comprised in a light chain of an antibody specifically directed to a tumor antigen; and wherein the (ii) heavy chain of the targeting moiety contains an amino acid sequence that is at least 60%, 70%, 75%, 80%, 85%, 90%, 95%, 96%, 97%, 98%, 99% or 100% identical to that comprised in a heavy chain of the antibody specifically directed to a tumor antigen. In some embodiments, the antibody specifically directed to a tumor antigen is an antibody selected from the group consisting of anti-HER2/neu, anti-HER3, anti-HER4, anti-CD4, anti-CD19, anti-CD20, anti-CD22, anti-CD29b, anti-CD30, anti-CD33, anti-CD37, anti-CD38, anti-CD52, anti-CD70, anti-CD79b, anti-CD123, anti-CD138, anti-CD200, anti-CD276, anti-CXCR3, anti-CXCR5, anti-CCR3, anti-CCR4, anti-CCR9, anti-CRTH2, anti-PMCH, anti-endoplasmin antibody, anti-VEGFR, anti-PDGFR, anti-CS1, anti-CEA, anti-mesothelin, anti-G250, anti-MUC1, anti-MUC16, anti-PSMA, anti-ADAM17, anti-EPCAM, anti-EphA2, anti-MCSP, anti-GPA33, anti-NAPi2b, anti-STEAP1, anti-CEACAM1, anti-CEACAM5, anti-GPNMB, anti-TROP, anti-TFGR, anti-EGFR, anti-IGFR, anti-FGFR, anti-HIFR, anti-heregulin receptor, anti-VEGF, anti-c-Met, anti-TGF, anti-EGF, anti-IGF, anti-FGF, anti-heregulin, anti-PDGF, anti-HIF, anti-human chorionic gonadotropin, anti-gonadotropin releasing hormone, anti-androgen, anti-estrogen, anti-thyroid-stimulating hormone, anti-follicle-stimulating hormone, anti-luteinizing hormone, anti-prolactin, anti-growth hormone, anti-adrenocorticotropic hormone, anti-antidiuretic hormone, anti-oxytocin, anti-thyrotropin-releasing hormone, anti-growth hormone releasing hormone, anti-corticotropin-releasing hormone, anti-somatostatin, anti-dopamine, anti-melatonin, anti-thyroxine, anti-calcitonin, anti-parathyroid hormone, anti-glucocorticoids, anti-mineralocorticoids, anti-adrenaline, anti-noradrenaline, anti-progesterone, anti-insulin, anti-glucagon, anti-amylin, anti-erythropoitin, anti-calcitriol, anti-calciferol, anti-atrial-natriuretic peptide, anti-gastrin, anti-secretin, anti-cholecystokinin, anti-neuropeptide Y, anti-ghrelin, anti-PYY3-36, anti-leptin, anti-thrombopoietin, anti-angiotensinogen, anti-IL-1, anti-IL-2, anti-IL-3, anti-IL-4, anti-IL-5, anti-IL-6, anti-IL-7, anti-IL-8, anti-IL-9, anti-IL-10, anti-IL-11, anti-IL-12, anti-IL-13, anti-IL-14, anti-IL-15, anti-IL-16, anti-IL-17, anti-IL-18, anti-IL-19, anti-IL-20, anti-IL-21, anti-IL-22, anti-IL-23, anti-IL-24, anti-IL-25, anti-IL-26, anti-IL-27, anti-IL-28, anti-IL-29, anti-IL-30, anti-IL-31, anti-IL-32, anti-IL-33, anti-IL-34, anti-IL-35, anti-IL-36, anti-collagen, anti-elastin, anti-biglycan, anti-decorin, anti-lumican, anti-versican, anti-perlecan, anti-C-reactive protein, anti-ApoE, and anti-laminin.

For example, the antibody specifically directed to a tumor antigen may be selected from the group consisting of anti-EGFR, anti-EGFR mutant, and anti-HER2.

In some embodiments, the immunoregulator comprised in the proteinaceous heterodimer augments an immune response. In some embodiments, the immunoregulator comprised in the proteinaceous heterodimer reduces an immune response. For example, the immunoregulator may be a cytokine. In some embodiments, the immunoregulator is a cytokine selected from the group consisting of interferon, interleukin, chemokine, lymphokine, and tumor necrosis factor. For example, the immunoregulator may be interferon alpha, interferon lamda or interferon beta. In some embodiments, the immunoregulator is selected from the group consisting of interleukin 10, interleukin 2, and super interleukin 2.

In some embodiments, the proteinaceous heterodimer of the present disclosure exhibits an expression yield that is at least 3-fold (e.g., at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, or more) higher than that of a corresponding control protein when expressed in a mammalian host cell, wherein the control protein comprises a dimer of two members, each member comprising a light chain and a heavy chain forming a targeting moiety specifically binding to the tumor antigen, wherein the heavy chain of each member further comprises the immunoregulator at a C-terminus. For example, the mammalian host cell may be HEK293 cell.

In some embodiments, the proteinaceous heterodimer of the present disclosure exhibits an in vivo half-life that is at least 2-fold (e.g., at least 3-fold, at least 4-fold, at least 5-fold, at least 6-fold, at least 7-fold, or more) longer than that of a corresponding control protein when expressed in mouse, wherein the control protein comprises a dimer of two members, each member comprising a light chain and a heavy chain forming a targeting moiety specifically binding to the tumor antigen, wherein the heavy chain of each member further comprises the immunoregulator at a C-terminus. In some embodiments, the heavy chain (ii) and the heavy chain fragment of the subject proteinaceous heterodimer each comprises a dimerization sequence that mediates heterodimerization of the one member and the other member to form the heterodimer. The dimerization sequence may be a heterodimerization sequence. In some embodiments, the heterodimerization sequence comprises one or more residues to effect heterodimerization via a covalent bond. In some embodiments, the dimerization sequence comprises Fc region of a heavy chain. For example, the dimerization sequence may comprise a constant region of an immunoglobulin selected from the group consisting of IgG1, IgG2, IgG3 and IgG4.

In some embodiments, the heterodimerization is effected via a non-covalent pairwise affinity of the dimerization or heterodimerization sequence contained in the heavy chain (ii) and the heavy chain fragment.

In some embodiments, the heavy chain fragment is fused in frame to the immunoregulator. For example, the heavy chain fragment may be fused in frame to the immunoregulator via a linker.

In some embodiments, the one other member comprises 2 or more immunoregulators fused in-frame to each other and to the heavy chain fragment. For example, the one other member may comprise 2 or more immunoregulators of the same type. In some embodiments, the one other member comprises 2 or more immunoregulators of different types.

In one aspect, the present disclosure provides an isolated polynucleotide encoding the subject proteinaceous heterodimer of the present disclosure.

In one aspect, the present disclosure provides a vector comprising the isolated polynucleotide of the present disclosure.

In one aspect, the present disclosure provides an isolated host cell comprising the isolated polynucleotide or the vector of the present disclosure.

In one aspect, the present disclosure provides a pharmaceutical composition comprising a pharmaceutically acceptable excipient and an isolated proteinaceous heterodimer of the present disclosure. The pharmaceutical composition may be formulated for oral administration, intravenous administration, intramuscular administration, in-situ administration at the site of a tumor, inhalation, rectal administration, vaginal administration, transdermal administration or administration via subcutaneous repository.

In one aspect, the present disclosure provides use of the subject proteinaceous heterodimer in the manufacture of a medicament and/or a kit for inhibiting growth of a tumor or a tumor cell.

In a further aspect, the present disclosure provides a method for inhibiting growth of a tumor or a tumor cell. In some embodiments, the method comprises contacting the tumor or tumor cell with an effective amount of the proteinaceous heterodimer of the present disclosure. In some embodiments, the contacting occurs in vitro. In some embodiments, the contacting occurs in vivo.

In one aspect, the present disclosure provides a method of producing a proteinaceous heterodimer, comprising (i) culturing the host cell of the present disclosure under conditions to effect expression of the heterodimer, and (ii) harvesting the expressed heterodimer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
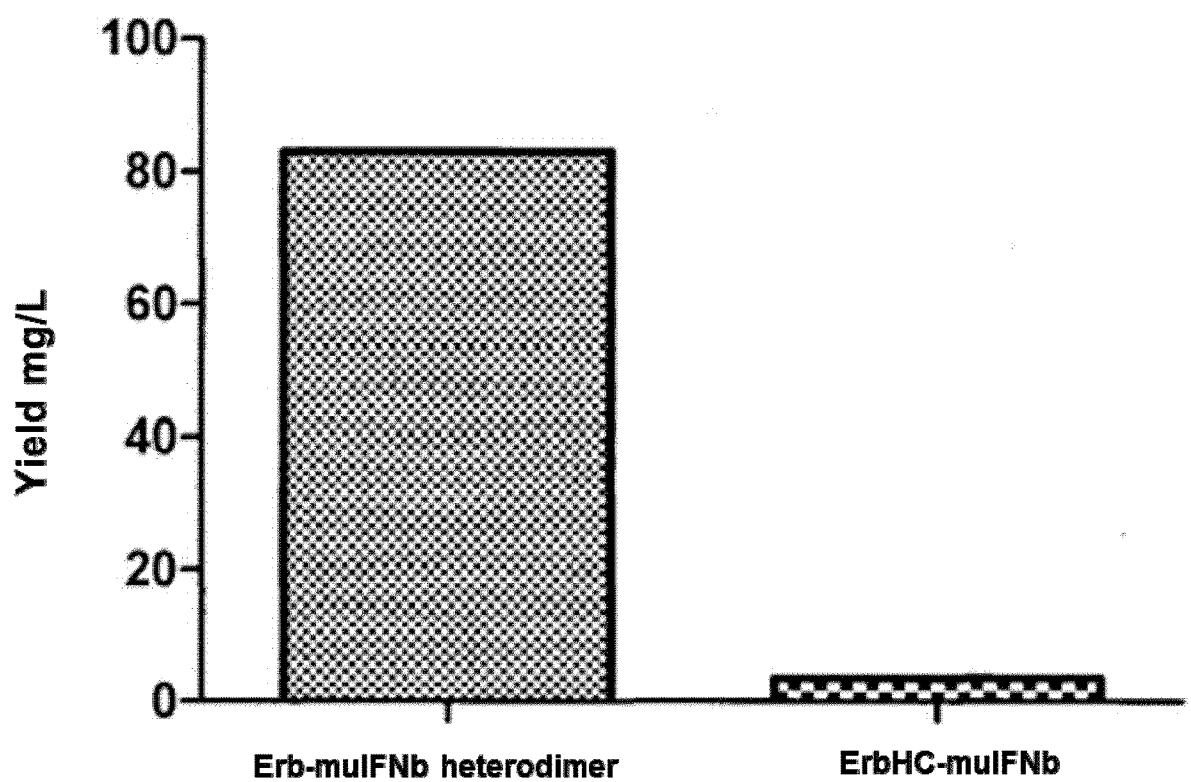
FIG. 1 illustrates expression yield of the heterodimer Erb-muIFNb and the control C-terminal fusion protein ErbHC-muIFNb.

Before the embodiments of the disclosure are described, it is to be understood that such embodiments are provided by way of example only, and that various alternatives to the embodiments of the disclosure described herein may be employed in practicing the disclosure. Numerous variations, changes, and substitutions will now occur to those skilled in the art without departing from the disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the disclosure.

The singular form "a," "an" and "the," as used herein, generally include plural references unless the context clearly dictates otherwise.

The term "proteinaceous," as used herein, generally refers to a material or molecule that is of, relating to, resembling, or being a polypeptide or a protein. For example, a proteinaceous heterodimer of the present disclosure may be a heterodimer protein, or a heterodimer comprising two or more polypeptides.

The term "heterodimer," as used herein, generally refers to a molecule (e.g. a proteinaceous molecule) composed of two different members. The two members of a heterodimer may differ in structure, function, activity and/or composition. For example, the two different members may comprise polypeptides differing in the order, number, or kind of amino acid residues forming these polypeptides. Each of the two different members of a heterodimer may independently comprise one, two or more units, polypeptide chains, or moieties.

The term "targeting moiety," as used herein, generally refers to a molecule, complex or aggregate, that binds specifically, selectively or preferentially to a target molecule, cell, particle, tissue or aggregate. For example, a targeting moiety may be an antibody, antigen-binding antibody fragment, bispecific antibody or other antibody-based molecule or compound. Other examples of targeting moieties may include, but are not limited to, aptamers, avimers, receptor-binding ligands, nucleic acids, biotin-avidin binding pairs, binding peptides or proteins, etc. The terms "targeting moiety" and "binding moiety" are used interchangeably herein.

The term "tumor antigen," as used herein, generally refers to an antigenic substance produced in or by tumor cells, which may have an ability to trigger an immune response in a host. For example, a tumor antigen may be a protein, a polypeptide, a peptide, or a fragment thereof, which constitutes part of a tumor cell and is capable of inducing tumor-specific cytotoxic T lymphocytes. A tumor antigen peptide may be a peptide that is generated as a result of degradation of the tumor antigen in a tumor cell and can induce or activate tumor-specific cytotoxic T lymphocytes upon being expressed on cell surface by binding to an HLA molecule. In some embodiments, the term "tumor antigen" may also refer to biomolecules (e.g., proteins, carbohydrates, glycoproteins, etc.) that are exclusively or preferentially or differentially expressed on a cancer cell and/or are found in association with a cancer cell and thereby provide targets preferential or specific to the cancer. For example, the preferential expression can be preferential expression as compared to any other cell in the organism, or preferential expression within a particular area of the organism (e.g. within a particular organ or tissue).

The terms "tumor antigen epitope" and "tumor antigen determinant" are used interchangeably herein and generally refer to the site of an amino acid sequence present in a tumor antigen that induces tumor-specific cytotoxic T lymphocytes.

The terms "immunoregulator" and "immunomodulator," are used interchangeably herein, and generally refer to a substance that affects the functioning of the immune system.

An immunoregulator may augment or reduce an immune response. For example, an immunoregulator may be an active agent of immunotherapy, including but not limited to, e.g., recombinant, synthetic and/or natural preparations of cytokines, granulocyte colony-stimulating factors (G-CSF), interferons, imiquimod, cellular membrane fractions from bacteria, chemokines, interleukins, cytosine phosphate-guanosine (CpG) oligodeoxynucleotides, and glucans. In some examples, the immunoregulator is a cytokine.

In some embodiments, the immunoregulator is selected from the group consisting of interferon, interleukin, chemokine, lymphokine, and tumor necrosis factor. For example, the immunoregulator may be selected from the group consisting of interferon alpha, interferon lamda, interferon beta, interleukin 10, interleukin 2, and super interleukin 2.

The term "membrane protein," as used herein, generally refers to a protein that interacts with a biological membrane. A membrane protein may be a protein attached to, or associated with, the membrane of a cell or organelle. For example, a membrane protein may be an integral membrane protein, a peripheral membrane protein, or a membrane-associated peptide. In some embodiments, a membrane protein is a cell surface receptor.

The term "cell surface receptor," as used herein, generally refers to cell-surface protein that binds to a bioactive molecule (e.g., a ligand) and mediates the effect of the ligand on the cell. A cell surface receptor may be a membrane-bound protein having a multi-domain structure comprising an extracellular ligand-binding domain and an intracellular effector domain that is typically involved in signal transduction. Binding of a ligand to a receptor may result in a conformational change in the receptor that causes an interaction between the effector domain and other molecule(s) in the cell. This interaction in turn may lead to an alteration in the metabolism of the cell. Metabolic events that are linked to receptor-ligand interactions may include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "expression yield," as used in the context of proteinaceous heterodimers herein, generally refers to an amount of a proteinaceous heterodimer being produced in functional form upon expression, e.g., when expressed by a host cell.

The term "dimerization sequence," as used herein, generally refers to an amino acid sequence capable of forming a dimer, or undergoing dimerization. A dimer may be a homodimer formed by two identical members. A dimer may be a heterodimer formed by two different members. In some cases, the two different members of a heterodimer may comprise identical dimerization sequences.

The term "heterodimerization sequence," as used herein, generally refers to an amino acid sequence preferentially resulting in formation of a heterodimer, or undergoing heterodimerization.

The term "covalent bond," as used herein, generally refers to a chemical bond formed between atoms by the sharing of electrons. For example, a covalent bond may be polar or non-polar. In some embodiments, a covalent bond is a disulfide bond.

The term "non-covalent pairwise affinity," as used herein, generally refers to that dimerization sequences or heterodimerization sequences capable of binding each other via non-covalent interaction, e.g., via ion pairs, hydrogen bonds, dipole-dipole interactions, charge transfer interactions, $\pi$-$\pi$ interactions, cation-$\pi$-electron interactions, van der Waals interactions and disperse interactions, hydrophobic (lipophilic) interactions, complex formation (e.g., complex formation of transition metal cations), or a combination of these interactions.

The term "linker," as used herein, generally refers to a synthetic amino acid sequence that connects or links two polypeptide sequences, e.g., that link two polypeptide domains. A linker may connect two amino acid sequences via peptide bonds. In some embodiments, a linker of the present disclosure connects a biologically active moiety to a second moiety in a linear sequence.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component. The terms may apply to amino acid polymers in which one or more amino acid residue is an artificial chemical analogue of a corresponding naturally occurring amino acid, as well as to naturally occurring amino acid polymers. The terms may also include variants on the traditional peptide linkage joining the amino acids making up the polypeptide. For example, the "peptides," "polypeptides," and "proteins" may be chains of amino acids whose alpha carbons are linked through peptide bonds. The terminal amino acid at one end of the chain (amino terminal) therefore may have a free amino group, while the terminal amino acid at the other end of the chain (carboxy terminal) may have a free carboxyl group. As used herein, the term "amino terminus" (abbreviated N-terminus) generally refers to the free $\alpha$-amino group on an amino acid at the amino terminal of a peptide or to the $\alpha$-amino group (imino group when participating in a peptide bond) of an amino acid at any other location within the peptide. Similarly, the term "carboxy terminus" generally refers to the free carboxyl group on the carboxy terminus of a peptide or the carboxyl group of an amino acid at any other location within the peptide. Peptides may also include essentially any poly amino acid including, but not limited to peptide mimetics such as amino acids joined by a ether as opposed to an amide bond.

The term "amino acid," as used herein, generally refers to either natural and/or unnatural or synthetic amino acids, including but not limited to, the D or L optical isomers or both, amino acid analogs and peptidomimetics. Standard single or three letter codes are used to designate amino acids.

The term "natural L-amino acid," as used herein, generally refers to the L optical isomer forms of glycine (G), proline (P), alanine (A), valine (V), leucine (L), isoleucine (I), methionine (M), cysteine (C), phenylalanine (F), tyrosine (Y), tryptophan (W), histidine (H), lysine (K), arginine (R), glutamine (Q), asparagine (N), glutamic acid (E), aspartic acid (D), serine (S), and threonine (T).

The term "non-naturally occurring," as used herein, generally refers to polypeptide or polynucleotide sequences that do not have a counterpart to, are not complementary to, or do not have a high degree of homology with a wild-type or naturally-occurring sequence (e.g., those found in a subject). For example, a non-naturally occurring polypeptide or fragment may share less than 99%, 98%, 95%, 90%, 80%, 70%, 60%, 50% or even less amino acid sequence identity as compared to a natural sequence when suitably aligned. Alternatively, a non-naturally occurring polypeptide or fragment may share more than 99%, 98%, 95%, 90%, 80%, 70%, 60%, 50% or even more amino acid sequence identity as compared to a natural sequence when suitably aligned.

The terms "hydrophilic" and "hydrophobic," as used herein, generally refer to the degree of affinity that a substance has with water. A hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be characterized based on their hydrophobicity. A number of scales have been developed. An example is a scale developed by Levitt, M, et al., J Mol Biol (1976) 104:59, which is listed in Hopp, T P, et al., Proc Natl Acad Sci USA (1981) 78:3824. Examples of "hydrophilic amino acids" are arginine, lysine, threonine, alanine, asparagine, and glutamine. Of particular interest are the hydrophilic amino acids aspartate, glutamate, and serine, and glycine. Examples of "hydrophobic amino acids" are tryptophan, tyrosine, phenylalanine, methionine, leucine, isoleucine, and valine.

The term "fragment," when used in the context of a proteinaceous molecule (e.g., a polypeptide or a protein), generally refers to a truncated form of a native biologically active protein that may or may not retain a portion of the therapeutic and/or biological activity.

The term "variant," when used in the context of a proteinaceous molecule (e.g., a polypeptide or a protein), generally refers to a proteinaceous molecule with sequence homology to the native biologically active protein that retains at least a portion of the therapeutic and/or biological activity of the biologically active protein. For example, a variant protein may share at least 60%, 65%, 70%, 75%, 80%, 85%, 90%, 95%, 96%, 97%, 98% or 99% amino acid sequence identity compared with the reference biologically active protein. In some embodiments, the "variant" may include proteins modified deliberately, as for example, by site directed mutagenesis, synthesis of the encoding gene, insertions, or accidentally through mutations.

The terms "conjugated," "linked," "fused," and "fusion" are used interchangeably herein, and generally refer to the joining together of two or more chemical elements, sequences or components, e.g., by means including chemical conjugation or recombinant means. For example, a promoter or enhancer is operably linked to a coding sequence if it effects the transcription of the sequence. Generally, "operably linked" means that the DNA sequences being linked are contiguous, and in reading phase or in-frame. An "in-frame fusion" refers to the joining of two or more open reading frames (ORFs) to form a continuous longer ORF, in a manner that maintains the correct reading frame of the original ORFs. Thus, the resulting "fusion polypeptide" is a single protein containing two or more fragments that correspond to polypeptides encoded by the original ORFs (which segments are not normally so joined in nature). The "fusion site" refers to the sequence where the two or more fragments are joined together. In some cases, the fusion site can be a sequence that is identical to sequences in the two or more fragments being joined. In some cases, the fusion site can further comprise a gap segment that is not identical to either of the sequences of the two or more fragments being joined.

In the context of polypeptides, a "linear sequence" or a "sequence" is an order of amino acids in a polypeptide in an amino to carboxyl terminus direction in which residues next to each other in the sequence are contiguous in the primary structure of the polypeptide. A "partial sequence" is a linear sequence forming part of a polypeptide that is known to comprise additional residues in one or both directions.

The terms "polynucleotides," "nucleic acids," "nucleotides" and "oligonucleotides" are used interchangeably herein, and they generally refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "gene" and "gene fragment" are used interchangeably herein and generally refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

The term "antibody," as used herein, generally refers to a protein comprising one or more polypeptides substantially encoded by immunoglobulin genes or fragments of immunoglobulin genes. The immunoglobulin genes may include the kappa, lambda, alpha, gamma, delta, epsilon and mu constant region genes, as well as myriad immunoglobulin variable region genes. As used herein, light chains may be classified as either kappa or lambda. Heavy chains may be classified as gamma, mu, alpha, delta, or epsilon, which in turn define the immunoglobulin classes, IgG, IgM, IgA, IgD and IgE, respectively. An antibody as used in the present disclosure may have a structural unit comprising a tetramer. Each tetramer may be composed of two identical pairs of polypeptide chains, each pair having one "light" (about 25 kD) and one "heavy" chain (about 50-70 kD). The N-terminus of each chain may define a variable region of about 100 to 110 or more amino acids primarily responsible for antigen recognition. The terms light chain variable region (VL) and heavy chain variable region (VH), as used herein, generally refer to these regions of the light and heavy chains respectively. Antibodies may exist as intact immunoglobulins or as a number of well characterized fragments produced by digestion with various peptidases or expressed de novo. Thus, for example, pepsin may digest an antibody below the disulfide linkages in the hinge region to produce F(ab)'2 (a dimer of Fab which itself is a light chain joined to VH-CH1 by a disulfide bond). The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term antibody, as used herein, may also include antibody fragments either produced by the modification of whole antibodies or synthesized de novo using recombinant DNA methodologies, including, but are not limited to, Fab'2, IgG, IgM, IgA, IgE, scFv, dAb, nanobodies, unibodies, and diabodies. In some embodiments, the antibodies include, but are not limited to Fab'2, IgG, IgM, IgA, IgE, and single chain antibodies, for example, single chain Fv (scFv) antibodies in which a variable heavy and a variable light chain are joined together (directly or through a peptide linker) to form a continuous polypeptide.

In some embodiments, antibodies and fragments in the present disclosure are bispecific. In some embodiments, bispecific antibodies or fragments thereof have binding specificities for at least two different epitopes (for example, at least one of the at least two different epitopes is a tumor associated antigen). In some embodiments, the antibodies and fragments may also be heteroantibodies, for example, they could be or could comprise two or more antibodies, or antibody binding fragments (e.g., Fab) linked together, with each antibody or fragment having a different specificity.

In some embodiments, antibodies and fragments thereof used herein can be bispecific. Bispecific antibodies or fragments thereof can be of various configurations. For example, bispecific antibodies may resemble single antibodies (or antibody fragments) but have two different antigen binding sites (variable regions). In various embodiments bispecific antibodies can be produced by chemical techniques (Kranz et al. (1981) Proc. Natl. Acad. Sci., USA, 78: 5807), by "polydoma" techniques (see, e.g., U.S. Pat. No. 4,474,893), or by recombinant DNA techniques. In some embodiments, bispecific antibodies as used herein may have binding specificities for at least two different epitopes and at least one of which is a tumor antigen. In some embodiments, the antibodies and fragments thereof may also be heteroantibodies. Heteroantibodies are two or more antibodies, or antibody binding fragments (e.g., Fab) linked together, each antibody or fragment having a different specificity.

The term "homology," "homologous" or "sequence identity," as used herein, generally refers to sequence similarity or interchangeability between two or more polynucleotide sequences or between two or more polypeptide sequences. When using a program (e.g. Emboss Needle or BestFit) to determine sequence identity, similarity or homology between two different amino acid sequences, the default settings may be used, or an appropriate scoring matrix, such as blosum45 or blosum80, may be selected to optimize identity, similarity or homology scores. In some embodiments, polynucleotides that are homologous are those which hybridize under stringent conditions and have at least 60%, at least 65%, at least 70%, at least 80%, at least 90%, at least 95%, at least 97%, at least 98%, at least 99%, and even 100% sequence identity compared to those sequences. Polypeptides that are homologous have sequence identities of at least 80%, or at least 90%, or at least 95%, or at least 97%, or at least 98%, or have at least 99% sequence identity when sequences of comparable length are optimally aligned.

The terms "percent identity" and "% identity," as used in the context of polynucleotide sequences, generally refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity may be measured over the length of an entire defined polynucleotide sequence, or may be measured over a shorter length, for example, over the length of a fragment taken from a larger, defined polynucleotide sequence. It is understood that any fragment length supported by the sequences shown herein, in the tables, figures or Sequence Listing, may be used to describe a length over which percentage identity may be measured.

The term "percent (%) sequence identity," as used in the context of polypeptide sequences identified herein, generally refers to the percentage of amino acid residues in a query sequence that are identical with the amino acid residues of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide sequence, or may be measured over a shorter length, for example, over the length of a fragment taken from a larger, defined polypeptide sequence. It is understood that any fragment length supported by the sequences shown herein, in the tables, figures or Sequence Listing, may be used to describe a length over which percentage identity may be measured.

The term "host cell," as used herein, generally includes an individual cell, a cell line or cell culture which can be or has been a recipient for the subject plasmids or vectors, comprise the polynucleotide of the present disclosure, or express the proteinaceous heterodimer (e.g. heterodimer protein) of the present disclosure. Host cells may include progeny of a single host cell. The progeny may not necessarily be completely identical (in morphology or in genomic of total DNA complement) to the original parent cell due to natural, accidental, or deliberate mutation. A host cell may include cells transfected in vitro with a vector of the present disclosure. A host cell may be a bacterial cell (e.g., *E. coli*), a yeast cell or other eukaryotic cells, e.g., a COS cell, a Chinese hamster ovary (CHO) cell, a HeLa cell, or a myeloma cell. In some embodiments, a host cell is a mammalian cell. In some embodiments, the mammalian cell is a HEK293 cell.

The term "vector," as used herein, generally refers to a nucleic acid molecule capable of self-replicating in an appropriate host, which transfers an inserted nucleic acid molecule into and/or between host cells. The term may include vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprising an expression vector that can function to yield a desired expression product.

The term "effective amount" or "therapeutically effective amount" refers to an amount of a composition (e.g., a proteinaceous heterodimer described herein) that is sufficient to effect the intended application, including but not limited to disease treatment. The therapeutically effective amount may vary depending upon the intended application (e.g., in vitro or in vivo), or the subject and disease condition being treated, e.g., the weight and age of the subject, the severity of the disease condition, the manner of administration and the like, which can readily be determined by one of ordinary skill in the art. The term may also apply to a dose that will induce a particular response in target cells, e.g. target gene induction, proliferation, and/or apoptosis. The specific dose will vary depending on the particular compounds chosen, the dosing regimen to be followed, whether it is administered in combination with other compounds, timing of administration, the tissue to which it is administered, and the physical delivery system in which it is carried.

The terms "treatment" or "treating," or "palliating" or "ameliorating" is used interchangeably herein, and refer to an approach for obtaining beneficial or desired results including but not limited to a therapeutic benefit and/or a prophylactic benefit. As used herein, therapeutic benefit generally refers to eradication or reduced severity of the underlying disorder being treated. Also, a therapeutic benefit is achieved with the eradication, reduced severity or reduced incidence of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

The term "therapeutic effect," as used herein, generally encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, generally encompass administration of two or more agents to an animal so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably herein, and they generally refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist," as used herein, generally refers to a compound having the ability to initiate or enhance a biological function of a target protein, whether by inhibiting or enhancing the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

The term "agent" or "biologically active agent," as used herein, generally refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

The term "anti-cancer agent," "anti-tumor agent" or "chemotherapeutic agent," as used herein, generally refers to any agent useful in the treatment of a neoplastic condition. One class of anti-cancer agents comprises chemotherapeutic agents.

The term "chemotherapy," as used herein, generally refers to the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation," as used herein, generally refers to a phenomenon by which the cell number has changed as a result of division. For example, cell proliferation may result in an increase in number of cells. This term also encompasses cell growth by which the cell morphology has changed (e.g., increased in size) consistent with a proliferative signal.

The term "in vivo," as used herein, generally refers to an event that takes place in a subject's body.

The term "in vitro," as used herein, generally refers to an event that takes places outside of a subject's body. For example, an in vitro assay encompasses any assay conducted outside of a subject. In vitro assays encompass cell-based assays in which dead or living cells are employed. In vitro assays also encompass a cell-free assay in which no intact cells are employed.

The term "interferon" (IFN), as used herein, generally refers to a signaling protein made and released by a host cell in response to the presence of pathogens, such as viruses, bacteria, parasites, or tumor cells. There are three major types of interferons, i.e. type I, type II and type III, wherein type I interferons may include IFN-α and IFN-β, and IFN-α may further comprise IFN-α subtypes, e.g., IFN-α2, IFN-α4, etc. Type I interferons may inhibit virus replication, have anti-parasitic activity, inhibit cell proliferation, stimulate cytotoxic activity of immune cells, be involved in immune regulation, and exhibit anti-tumor effects. Type II and Type III interferons may include IFN-γ, IFN-λ1 (IL-29), IFN-λ2 (IL-28a) and IFN-λ3 (IL-28b). As used herein, the term "interferon" may include full length interferons, or a fragment (e.g., a truncated form) or variant thereof substantially maintaining the biological activities of a corresponding wild-type interferon (e.g., having a biological activity that is at least 80%, at least 90%, at least 95%, at least 98%, at least 99%, or even at least 100% of the biological activity of a corresponding wild-type interferon). An interferon, as used herein, may be from any mammalian species. In some embodiments, the interferon is from a species selected from the group consisting of human, horse, cattle, murine, pig, rabbit, cat, dog, rat, goat, sheep, and non-human primate.

The term "interleukin," as used herein, generally refers to a secreted protein or a signaling molecule capable of promoting the development and differentiation of T and/or B lymphocytes and/or hematopoietic cells. An interleukin may be synthesized by helper CD4 T lymphocytes, as well as through monocytes, macrophages, and endothelial cells. As used herein, an interleukin (IL) may include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and/or IL-36. As used herein, the term "interleukin" may include full length interleukins, or a fragment (e.g., a truncated form) or variant thereof substantially maintaining the biological activities of a corresponding wild-type interleukin (e.g., having a biological activity that is at least 80%, at least 90%, at least 95%, at least 98%, at least 99%, or even at least 100% of the biological activity of a corresponding wild-type interleukin). An interleukin, as used herein, may be from any mammalian species. In some embodiments, the interleukin is from a species selected from the group consisting of human, horse, cattle, murine, pig, rabbit, cat, dog, rat, goat, sheep, and non-human primate. In some embodiments, the interleukin can be in a mutated form, for example, with increased or decreased affinity to its receptors. In specific embodiments, the interleukin can be a super IL-2 (also known as sIL2, see *Nature* 484, 529-533, 26 Apr. 2012), which may be obtained by modifying IL-2 to increase its binding affinity for IL-2Rβ. Mutations in sIL-2 are principally in the core of the cytokine, and molecular dynamics simulations indicated that the evolved mutations stabilized IL-2, reducing the flexibility of a helix in the IL-2Rβ binding site, into an optimized receptor-binding conformation resembling that when bound to CD25. Compared to IL-2, sIL-2 induced superior expansion of cytotoxic T cells, leading to improved anti-tumor responses in vivo, and elicited proportionally less expansion of T regulatory cells and reduced pulmonary edema.

The term "antibody," as used herein, generally refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as various immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The term "antigen-binding site" or "binding portion," as used herein, generally refers to a part of an antibody that participates in antigen binding. An antigen binding site may be formed by amino acid residues of the N-terminal variable ("V") regions of a heavy ("H") chain and/or a light ("L") chain. Three highly divergent stretches within the V regions of the heavy and light chains are referred to as "hypervariable regions" which are interposed between more conserved flanking stretches known as "framework regions" or "FRs". Thus, the term "FR," as used herein, generally refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three-dimensional space to form an antigen binding "surface". This surface may mediate recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4$^{th}$ ed. U.S. Dept. Health and Human Services, Public Health Services, Bethesda, Md. (1987).

The term "anti-HER2/neu antibody," as used herein, generally refers to an antibody that specifically or preferentially binds a HER2/neu receptor. For example, an anti-HER2/neu antibody or anti-HER2 antibody could be Trastuzumab, Pertuzumab, or antigen binding fragments thereof.

The term "anti-EGFR antibody," as used herein, generally refers to an antibody that specifically or preferentially binds an EGFR. In some cases, and anti-EGFR antibody may bind to a mutated form of EGFR (e.g., EGFR variant III (also known as EGFRvIII), which is the most common extracellular domain mutation of EGFR, this mutation leads to a deletion of exons 2-7 of the EGFR gene and renders the mutant receptor incapable of binding any known ligand). For example, an anti-EGFR antibody may be Cetuximab, Mab806, or antigen binding fragments thereof.

The term "subject," as used herein, generally refers to a human or non-human animal, including, but not limited to, a cat, dog, horse, pig, cow, sheep, goat, rabbit, mouse, rat, or monkey.

The term "anti-EGFR family antibody," as used herein, generally refers to an antibody that specifically binds to a member of the epidermal growth factor receptor family. For example, it may be an antibody that binds to ErbB-1 (also named as epidermal growth factor receptor (EGFR)), ErbB-2 (also named as HER2 in humans and as neu in rodents), ErbB-3 (also named as HER3), and/or to ErbB-4 (also named as HER4). Examples of anti-EGFR family antibodies include, but are not limited to one or more of the following antibodies: C6.5, C6mL3-9, C6 MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7, etc., also see, e.g., U.S. Patent publications US 2006/0099205 A1 and US 2004/0071696 A1, which are incorporated herein by reference.

The term "single chain Fv" ("sFv" or "scFv") polypeptide, as used herein, generally refers to a covalently linked VH (heavy chain variable region):VL (light chain variable region) heterodimer, which may be expressed from a nucleic acid including VH- and VL-encoding sequences either joined directly or joined by a peptide-encoding linker. (see Huston, et al. *Proc. Nat. Acad. Sci. USA*, 85: 5879-5883 (1988)).

The term "inhibition of growth and/or proliferation," when used with cancer cells, generally refers to decrease in the growth rate and/or proliferation rate of a cancer cell. For example, this may include death of a cancer cell (e.g. via apoptosis). In some embodiments, this term may also refer to inhibiting the growth and/or proliferation of a solid tumor and/or inducing tumor size reduction or elimination of the tumor.

The term "a cancer cell surface marker" or "a cancer cell associated marker," as used herein, generally refers to biomolecules such as proteins, carbohydrates, glycoproteins, and the like that are exclusively or preferentially or differentially expressed on a cancer cell and/or are found to be associated with a cancer cell and thereby provide targets preferential or specific to the cancer. In some embodiments, the preferential expression can be preferential expression as compared to any other cell in the organism, or preferential expression within a particular area of the organism (e.g. within a particular organ or tissue).

The term "CD20," as used herein, generally refers to a non-glycosylated phosphoprotein expressed on the surface of mature B-cells (see, e.g., Cragg et al. (2005) Curr. Dir. Autoimmun., 8: 140-174). It may also be found on B-cell lymphomas, hairy cell leukemia, B-cell chronic lymphocytic leukemia on skin/melanoma cancer stem cells, etc.

Proteinaceous Heterodimers, Isolated Polynucleotides, Vectors and Host Cells

In one aspect, the present disclosure provides proteinaceous heterodimers. One member of the heterodimer may comprise (i) a light chain and (ii) a heavy chain complexed to form a targeting moiety exhibiting binding specificity to a tumor antigen. One other member of the heterodimer may comprise a polypeptide comprising, from N-terminus to C-terminus, an immunoregulator fused to a heavy chain fragment. The heavy chain fragment may complex with the heavy chain (ii) to form the heterodimer.

In some embodiments, the heavy chain (ii) and the heavy chain fragment each comprises a dimerization sequence that mediates heterodimerization of the one member and the other member to form the heterodimer. For example, the heavy chain (ii) and the heavy chain fragment each may comprise an amino acid sequence capable of forming a dimer, or undergoing dimerization. Such dimers may be formed by two identical dimerization sequences or by two different dimerization sequences.

In some embodiments, the dimerization sequence is a heterodimerization sequence, wherein a heterodimer is formed via dimerization of two different dimerization sequences. In some embodiments, the heterodimerization sequence comprises one or more residues to effect heterodimerization via a covalent bond.

In some embodiments, the dimerization sequence comprises an Fc region of a heavy chain (such as an antibody heavy chain). In some embodiments, each of the dimerization sequences independently comprises a constant region of an immunoglobulin (e.g., from an immunoglobulin selected from the group consisting of IgG1, IgG2, IgG3 and IgG4), or a variant thereof. In some embodiments, the dimerization sequence in the heavy chain (ii) of the targeting moiety and that in the heavy chain fragment each comprises a constant region of an immunoglobulin of the same subtype. For example, said immunoglobulin constant region may comprise an amino acid sequence as set forth in SEQ ID NO:45, SEQ ID NO:46, SEQ ID NO:47, SEQ ID NO:48, or a variant thereof sharing more than 50%, 60%, 70%, 80%, 90%, 95%, 98%, 99% or even more amino acid sequence identity thereto.

In some embodiments, the dimerization sequence comprised in the heavy chain fragment may be that of a constant region from immunoglobulin γ1 (IgG1). In some embodiments, the IgG1 is human IgG1. In some embodiments, the dimerization sequence comprised in the heavy chain fragment comprises a point mutation, such as Y349C, T366S, L368A and/or Y407V at positions corresponding to positions 349, 366, 368 and/or 407 of human IgG1 constant region, when compared to the amino acid sequence of human IgG1 constant region.

In some embodiments, the heterodimerization is effected via a non-covalent pairwise affinity of the dimerization or heterodimerization sequence contained in the heavy chain (ii) and the heavy chain fragment.

In some embodiments, the heavy chain fragment is fused in frame to an immunoregulator. For example, the heavy chain fragment may be fused in frame to the immunoregulator via a linker. The linker may be a synthetic amino acid sequence that connects or links two polypeptide sequences, e.g., via peptide bonds. In some embodiments, a linker is a peptide comprising 1, 2, 3, 4, 5, 6, 7, 8, 9, 10, 11, 12, 13, 14, 15, 16, 17, 18, 19, 20, 21, 22, 23, 24, 25 or more amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. In some embodiments, the linker comprises an amino acid sequence as set forth in SEQ ID NO: 27, SEQ ID NO: 77, SEQ ID NO: 78, or SEQ ID NO: 79. In some embodiments, the linker is resistant to proteolysis or substantially resistant to proteolysis.

In some embodiments, the one other member of the proteinaceous heterodimer comprises two or more (e.g., 2, 3, 4, 5, or more) immunoregulators fused in-frame to each other and to the heavy chain fragment (e.g., as in Erb-(huIL10)2, Tmab-(huIL10)2, Mab806-(huIL10)2, or Pmab-(huIL10)2). For example, the two or more immunoregulators may be fused in-frame to each other and/or to the heavy chain fragment via a linker. The linker may be a synthetic amino acid sequence that connects or links two polypeptide sequences, e.g., via peptide bonds. In some embodiments, a linker is a peptide comprising e.g., 1, 2, 3, 4, 5, 6, 7, 8, 9, 10, 11, 12, 13, 14, 15, 16, 17, 18, 19, 20, 21, 22, 23, 24, 25 or more amino acids. The two or more immunoregulators may be of the same type or may be of different types. For example, the two or more immunoregulators may be two or more IL10, or may be one or more interferon and one or more interleukin. In some embodiments, one or more of the two or more immunoregulators may be selected from any of the immunoregulators described elsewhere in the present disclosure.

In some embodiments, the targeting moiety specifically binds to a tumor antigen that is a membrane protein. In some embodiments, the targeting moiety specifically binds to a tumor antigen that is a cell surface receptor. For example, the cell surface receptor may be selected from the group consisting of transforming growth factor receptor (TGFR), epidermal growth factor receptor (EGFR), insulin-like growth factor receptor (IGFR), fibroblast growth factor receptor (FGFR), heregulin receptor, platelet-derived growth factor receptor (PDGFR), vascular endothelial growth factor receptor (VEGFR), and hypoxia inducible factor receptor (HIFR).

In some embodiments, the targeting moiety specifically binds to a tumor antigen that is a growth factor, hormone, or an extracellular matrix molecule. For example, the growth factor, hormone, or extracellular matrix molecule may be selected from the group consisting of transforming growth factor (TGF), epidermal growth factor (EGF), insulin-like growth factor (IGF), fibroblast growth factor (FGF), heregulin, platelet-derived growth factor (PDGF), vascular endothelial growth factor (VEGF), hypoxia inducible factor (HIF), c-Met, human chorionic gonadotropin, gonadotropin releasing hormone, androgen, estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, leptin, thrombopoietin, angiotensinogen, IL-1, IL-2, IL-3, IL-4, IL-5, IL-6, IL-7, IL-8, IL-9, IL-10, IL-11, IL-12, IL-13, IL-14, IL-15. IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, collagen, elastin, biglycan, decorin, lumican, versican, perlecan, C-reactive protein, ApoE, and laminins.

In some embodiments, the targeting moiety specifically binds to a tumor antigen selected from the group consisting of EGFR mutant (e.g., EGFR variant III), HER2/neu, HER3, HER4, CD4, CD19, CD20, CD22, CD29b, CD30, CD33, CD37, CD38, CD52, CD70, CD79b, CD123, CD138, CD200, CD276, CXCR3, CXCR5, CCR3, CCR4, CCR9, CRTH2, PMCH, endoplasmin, CS1, CEA, mesothelin, 6250, MUC1, MUC16, PSMA, ADAM17, EPCAM, EphA2, MCSP, GPA33, NAPi2b, STEAP1, CEACAM1, CEACAM5, GPNMB and TROP. For example, the targeting moiety may specifically bind to EGFR, an EGFR mutant (e.g., EGFR variant III), or HER2/neu.

In some embodiments, the (i) light chain of the targeting moiety contains complementarity determining regions (e.g., CDR1, CDR2 and/or CDR3) comprising an amino acid sequence that is at least 60%, 70%, 75%, 80%, 85%, 90%, 95%, 96%, 97%, 98%, 99% or 100% identical to that comprised in the corresponding CDRs (e.g., corresponding CDR1, CDR2 and/or CDR3) of a light chain of an antibody specifically directed to a tumor antigen. In some embodiments, the identity is at least 80%, or at least 90%. The tumor antigen may be any of those defined or listed in the present disclosure. In some embodiments, the antibody specifically directed to a tumor antigen is anti-EGFR (e.g., Cetuximab), anti-EGFR mutant (e.g., anti-EGFR variant III, for example, Mab806) or anti-HER2 (e.g., Trastuzumab or Pertuzumab). For example, the amino acid sequence comprised in CDRs of a light chain of an antibody specifically directed to a tumor antigen may be selected from the group consisting of SEQ ID NO: 31, SEQ ID NO: 32, SEQ ID NO: 33, SEQ ID NO: 39, SEQ ID NO: 40, SEQ ID NO: 41, SEQ ID NO: 62, SEQ ID NO: 63, SEQ ID NO: 64, SEQ ID NO: 71, SEQ ID NO: 72, and SEQ ID NO: 73.

In some embodiments, the (i) light chain of the targeting moiety contains a variable region comprising an amino acid sequence that is at least 60%, 70%, 75%, 80%, 85%, 90%, 95%, 96%, 97%, 98%, 99% or 100% identical to that comprised in a variable region of a light chain of an antibody specifically directed to a tumor antigen. In some embodiments, the identity is at least 80%, or at least 90%.The tumor antigen may be any of those defined or listed in the present disclosure. In some embodiments, the antibody specifically directed to a tumor antigen is selected from anti-EGFR (e.g., Cetuximab), anti-EGFR mutant (e.g., anti-EGFR variant III, for example, Mab806) or anti-HER2 (e.g., Trastuzumab or Pertuzumab). For example, the amino acid sequence comprised in a variable region of a light chain of an antibody specifically directed to a tumor antigen may be selected from a group consisting of: SEQ ID NO: 29, SEQ ID NO: 37, SEQ ID NO: 58, and SEQ ID NO: 69.

In some embodiments, the (i) light chain of the targeting moiety comprises an amino acid sequence that is at least 60%, 70%, 75%, 80%, 85%, 90%, 95%, 96%, 97%, 98%, 99% or 100% identical to that comprised in a light chain of an antibody specifically directed to a tumor antigen. In some embodiments, the identity is at least 80%, or at least 90%. The tumor antigen may be any of those defined or listed in the present disclosure. In some embodiments, the antibody specifically directed to a tumor antigen may be anti-EGFR (e.g., Cetuximab), anti-EGFR mutant (e.g., anti-EGFR variant III, for example, Mab806) or anti-HER2 (e.g., Trastuzumab or Pertuzumab). For example, the amino acid sequence comprised in a light chain of an antibody specifically directed to a tumor antigen may be selected from a group consisting of: SEQ ID NO: 11, SEQ ID NO: 15, SEQ ID NO: 55, and SEQ ID NO: 65.

In some embodiments, the (ii) heavy chain of the targeting moiety may contain CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of an antibody specifically directed to a tumor antigen. In some embodiments, the identity is at least 80%, or at least 90%. The tumor antigen may be any of those defined or listed in the present disclosure. In some embodiments, the antibody specifically directed to a tumor antigen is anti-EGFR (e.g., Cetuximab), anti-EGFR mutant (e.g., anti-EGFR variant III, for example, Mab806) or anti-HER2 (e.g., Trastuzumab or Pertuzumab). For example, the amino acid sequence comprised in CDRs of a heavy chain of an antibody specifically directed to a tumor antigen may be selected from the group consisting of SEQ ID NO: 34, SEQ ID NO: 35, SEQ ID NO: 36, SEQ ID NO: 42, SEQ ID NO: 43, SEQ ID NO: 44, SEQ ID NO: 59, SEQ ID NO: 60, SEQ ID NO: 61, SEQ ID NO: 74, SEQ ID NO: 75, and SEQ ID NO: 76.

In some embodiments, the (ii) heavy chain of the targeting moiety contains a variable region comprising an amino acid sequence that is at least 60%, 70%, 75%, 80%, 85%, 90%, 95%, 96%, 97%, 98%, 99% or 100% identical to that comprised in a variable region of a heavy chain of an antibody specifically directed to a tumor antigen. In some embodiments, the identity is at least 80%, or at least 90%. The tumor antigen may be any of those defined or listed in the present disclosure. In some embodiments, the antibody specifically directed to a tumor antigen is anti-EGFR (e.g., Cetuximab), anti-EGFR mutant (e.g., anti-EGFR variant III, for example, Mab806) or anti-HER2 (e.g., Trastuzumab or Pertuzumab). For example, the amino acid sequence comprised in a variable region of a heavy chain of an antibody specifically directed to a tumor antigen may be selected from a group consisting of: SEQ ID NO: 30, SEQ ID NO: 38, SEQ ID NO: 57, and SEQ ID NO: 70.

In some embodiments, the (ii) heavy chain of the targeting moiety comprises an amino acid sequence that is at least 60%, 70%, 75%, 80%, 85%, 90%, 95%, 96%, 97%, 98%, 99% or 100% identical to that comprised in a heavy chain of an antibody specifically directed to a tumor antigen. In some embodiments, the identity is at least 80%, or at least 90%. The tumor antigen may be any of those defined or listed in the present disclosure. In some embodiments, the antibody specifically directed to a tumor antigen is anti-EGFR (e.g., Cetuximab), anti-EGFR mutant (e.g., anti-EGFR variant III, for example, Mab806) or anti-HER2 (e.g., Trastuzumab or Pertuzumab). For example, the amino acid sequence comprised in a heavy chain of an antibody specifically directed to a tumor antigen may be selected from a group consisting of: SEQ ID NO: 13, SEQ ID NO: 17, SEQ ID NO: 53, and SEQ ID NO: 67.

In some embodiments, the (i) light chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a light chain of an antibody specifically directed to a tumor antigen; and the (ii) heavy chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of the same antibody specifically directed to a tumor antigen. In some embodiments, the identity is at least 80%, or at least 90%. The tumor antigen may be any of those defined or listed in the present disclosure. In some embodiments, the antibody specifically directed to a tumor antigen is anti-EGFR (e.g., Cetuximab), anti-EGFR mutant (e.g., anti-EGFR variant III, for example, Mab806) or anti-HER2 (e.g., Trastuzumab or Pertuzumab). For example, the amino acid sequence comprised in CDRs of a light chain of an antibody specifically directed to a tumor antigen may be selected from the group consisting of SEQ ID NO: 31, SEQ ID NO: 32, and SEQ ID NO: 33, and the amino acid sequence comprised in CDRs of a heavy chain of the same antibody specifically directed to a tumor antigen may be selected from the group consisting of SEQ ID NO: 34, SEQ ID NO: 35, and SEQ ID NO: 36. In another example, the amino acid sequence comprised in CDRs of a light chain of an antibody specifically directed to a tumor antigen may be selected from the group consisting of SEQ ID NO: 39, SEQ ID NO: 40, and SEQ ID NO: 41, and the amino acid sequence comprised in CDRs of a heavy chain of the same antibody specifically directed to a tumor antigen may be selected from the group consisting of SEQ ID NO: 42, SEQ ID NO: 43, and SEQ ID NO: 44. In a further example, the amino acid sequence comprised in CDRs of a light chain of an antibody specifically directed to a tumor antigen may be selected from the group consisting of SEQ ID NO: 62, SEQ ID NO: 63, and SEQ ID NO: 64, and the amino acid sequence comprised in CDRs of a heavy chain of the same antibody specifically directed to a tumor antigen may be selected from the group consisting of SEQ ID NO: 59, SEQ ID NO: 60, and SEQ ID NO: 61. In another example, the amino acid sequence comprised in CDRs of a light chain of an antibody specifically directed to a tumor antigen may be selected from the group consisting of SEQ ID NO: 71, SEQ ID NO: 72, and SEQ ID NO: 73, and the amino acid sequence comprised in CDRs of a heavy chain of the same antibody specifically directed to a tumor antigen may be selected from the group consisting of SEQ ID NO: 74, SEQ ID NO: 75, and SEQ ID NO: 76.

In some embodiments, the (i) light chain of the targeting moiety may contain a variable region comprising an amino acid sequence that is at least 60%, 70%, 75%, 80%, 85%, 90%, 95%, 96%, 97%, 98%, 99% or 100% identical to that comprised in a variable region of a light chain of an antibody specifically directed to a tumor antigen; and the (ii) heavy chain of the targeting moiety contains a variable region comprising an amino acid sequence that is at least 60%, 70%, 75%, 80%, 85%, 90%, 95%, 96%, 97%, 98%, 99% or 100% identical to that comprised in a variable region of a heavy chain of the same antibody specifically directed to a tumor antigen. In some embodiments, the identity is at least 80%, or at least 90%. The tumor antigen may be any of those defined or listed in the present disclosure. In some embodiments, the antibody specifically directed to a tumor antigen may be anti-EGFR (e.g., Cetuximab), anti-EGFR mutant (e.g., anti-EGFR variant III, for example, Mab806) or anti-HER2 (e.g., Trastuzumab or Pertuzumab). For example, the amino acid sequence comprised in a variable region of a light chain of an antibody specifically directed to a tumor antigen may be as set forth in SEQ ID NO: 29, and the amino acid sequence comprised in a variable region of a heavy chain of the same antibody specifically directed to a tumor antigen may be as set forth in SEQ ID NO: 30. In another example, the amino acid sequence comprised in a variable region of a light chain of an antibody specifically directed to a tumor antigen may be as set forth in SEQ ID NO: 37, and the amino acid sequence comprised in a variable region of a heavy chain of the same antibody specifically directed to a tumor antigen may be as set forth in SEQ ID NO: 38. In a further example, the amino acid sequence comprised in a variable region of a light chain of an antibody specifically directed to a tumor antigen may be as set forth in SEQ ID NO: 58, and the amino acid sequence comprised in a variable region of a heavy chain of the same antibody specifically directed to a tumor antigen may be as set forth in SEQ ID NO: 57. In another example, the amino acid sequence comprised in a variable region of a light chain of an antibody specifically directed to a tumor antigen may be as set forth in SEQ ID NO: 69, and the amino acid sequence comprised in a variable region of a heavy chain of the same antibody specifically directed to a tumor antigen may be as set forth in SEQ ID NO: 70.

In some embodiments, the (i) light chain of the targeting moiety contains an amino acid sequence that is at least 60%, 70%, 75%, 80%, 85%, 90%, 95%, 96%, 97%, 98%, 99% or 100% identical to that comprised in a light chain of an antibody specifically directed to a tumor antigen; and the (ii) heavy chain of the targeting moiety contains an amino acid sequence that is at least 60%, 70%, 75%, 80%, 85%, 90%, 95%, 96%, 97%, 98%, 99% or 100% identical to that comprised in a heavy chain of the same antibody specifically directed to a tumor antigen. In some embodiments, the identity is at least 80%, or at least 90%. The tumor antigen may be any of those defined or listed in the present disclosure. In some embodiments, the antibody specifically directed to a tumor antigen is anti-EGFR (e.g., Cetuximab), anti-EGFR mutant (e.g., anti-EGFR variant III, for example, Mab806) or anti-HER2 (e.g., Trastuzumab or Pertuzumab). For example, the amino acid sequence comprised in a light chain of an antibody specifically directed to a tumor antigen may be as set forth in SEQ ID NO: 11, and the amino acid sequence comprised in a heavy chain of an antibody specifically directed to a tumor antigen may be as set forth in SEQ ID NO: 13. In another example, the amino acid sequence comprised in a light chain of an antibody specifically directed to a tumor antigen may be as set forth in SEQ ID NO: 15, and the amino acid sequence comprised in a heavy chain of an antibody specifically directed to a tumor antigen may be as set forth in SEQ ID NO: 17. In a further example, the amino acid sequence comprised in a light chain of an antibody specifically directed to a tumor antigen may be as set forth in SEQ ID NO: 55, and the amino acid sequence comprised in a heavy chain of an antibody specifically directed to a tumor antigen may be as set forth in SEQ ID NO: 53. In another example, the amino acid sequence comprised in a light chain of an antibody specifically directed to a tumor antigen may be as set forth in SEQ ID NO: 65, and the amino acid sequence comprised in a heavy chain of an antibody specifically directed to a tumor antigen may be as set forth in SEQ ID NO: 67.

In some embodiments, the antibody specifically directed to a tumor antigen is an antibody selected from the group consisting of anti-HER2/neu, anti-HER3, anti-HER4, anti-CD4, anti-CD19, anti-CD20, anti-CD22, anti-CD29b, anti-CD30, anti-CD33, anti-CD37, anti-CD38, anti-CD52, anti-CD70, anti-CD79b, anti-CD123, anti-CD138, anti-CD200, anti-CD276, anti-CXCR3, anti-CXCR5, anti-CCR3, anti-CCR4, anti-CCR9, anti-CRTH2, anti-PMCH, anti-endoplasmin antibody, anti-VEGFR, anti-PDGFR, anti-CS1, anti-CEA, anti-mesothelin, anti-G250, anti-MUC1, anti-MUC16, anti-PSMA, anti-ADAM17, anti-EPCAM, anti-EphA2, anti-MCSP, anti-GPA33, anti-NAPi2b, anti-STEAP1, anti-CEACAM1, anti-CEACAM5, anti-GPNMB, anti-TROP, anti-TFGR, anti-EGFR, anti-IGFR, anti-FGFR, anti-HIFR, anti-heregulin receptor, anti-VEGF, anti-TGF, anti-EGF, anti-IGF, anti-FGF, anti-heregulin, anti-PDGF, anti-HIF, anti-c-Met, anti-human chorionic gonadotropin, anti-gonadotropin releasing hormone, anti-androgen, anti-estrogen, anti-thyroid-stimulating hormone, anti-follicle-stimulating hormone, anti-luteinizing hormone, anti-prolactin, anti-growth hormone, anti-adrenocorticotropic hormone, anti-antidiuretic hormone, anti-oxytocin, anti-thyrotropin-releasing hormone, anti-growth hormone releasing hormone, anti-corticotropin-releasing hormone, anti-somatostatin, anti-dopamine, anti-melatonin, anti-thyroxine, anti-calcitonin, anti-parathyroid hormone, anti-glucocorticoids, anti-mineralocorticoids, anti-adrenaline, anti-noradrenaline, anti-progesterone, anti-insulin, anti-glucagon, anti-amylin, anti-erythropoitin, anti-calcitriol, anti-calciferol, anti-atrial-natriuretic peptide, anti-gastrin, anti-secretin, anti-cholecystokinin, anti-neuropeptide Y, anti-ghrelin, anti-PYY3-36, anti-leptin, anti-thrombopoietin, anti-angiotensinogen, anti-IL-1, anti-IL-2, anti-IL-3, anti-IL-4, anti-IL-5, anti-IL-6, anti-IL-7, anti-IL-8, anti-IL-9, anti-IL-10, anti-IL-11, anti-IL-12, anti-IL-13, anti-IL-14, anti-IL-15, anti-IL-16, anti-IL-17, anti-IL-18, anti-IL-19, anti-IL-20, anti-IL-21, anti-IL-22, anti-IL-23, anti-IL-24, anti-IL-25, anti-IL-26, anti-IL-27, anti-IL-28, anti-IL-29, anti-IL-30, anti-IL-31, anti-IL-32, anti-IL-33, anti-IL-34, anti-IL-35, anti-IL-36, anti-collagen, anti-elastin, anti-biglycan, anti-decorin, anti-lumican, anti-versican, anti-perlecan, anti-C-reactive protein, anti-ApoE, and anti-laminin. For example, the antibody specifically directed to a tumor antigen may be anti-EGFR, anti-EGFR mutant (e.g., anti-EGFR variant III), or anti-HER2.

In some embodiments, the immunoregulator augments an immune response. Examples of immunoregulators capable of augmenting an immune response include, without limitation, IL-2, IFNα, IFNβ, IFNγ, IFNλ, Tumor Necrosis Factor (TNF) a, IL-12, and IL-10.

In some embodiments, the the immunoregulator reduces an immune response. Non-limiting examples of immunoregulators capable of reducing an immune response include IL-10, and Transforming Growth Factor (TGF)-β.

In some embodiments, the immunoregulator is a cytokine. For example, the immunoregulator may be a cytokine selected from the group consisting of interferon, interleukin, chemokine, lymphokine, and tumor necrosis factor. In some embodiments, the immunoregulator is interferon alpha, interferon lamda or interferon beta. In some embodiments, the immunoregulator is interleukin 10, interleukin 2, or super interleukin 2.

In some embodiments, the proteinaceous heterodimer of the present disclosure exhibits an expression yield that is at least 2-fold higher than that of a corresponding control protein when expressed in a host cell. For example, the proteinaceous heterodimer of the present disclosure may exhibit an expression yield that is at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold or more higher than that of a corresponding control protein. The host cell may be a plant cell, a mammalian cell, an insect cell, or a bacterial cell. In some embodiments, the host cell is a mammalian cell. In some embodiments, the host cell is a HEK293 cell. The control protein may comprise a dimer of two members, and each member may comprise a light chain and a heavy chain forming a targeting moiety specifically binding to a tumor antigen. For example, the tumor antigen may be identical to that bound by the targeting moiety comprised in the proteinaceous heterodimer. In some embodiments, the heavy chain of each member of the control protein further comprises an immunoregulator at its C-terminus. For example, the immunoregulator may be identical to that comprised in the proteinaceous heterodimer.

In some embodiments, the proteinaceous heterodimer of the present disclosure exhibits an in vivo half-life that is at least 2-fold longer than that of a corresponding control protein when expressed in, or administered to, a subject. For example, the proteinaceous heterodimer of the present disclosure may exhibit an in vivo half-life that is at least 3-fold, at least 4-fold, at least 5-fold, at least 6-fold, at least 7-fold or more longer than that of a corresponding control protein when expressed in, or administered to, a subject. The subject may be a mammal, such as a rodent (e.g., a mouse, a rabbit, or a rat), a domestic animal (e.g., a cat, a swine, a dog, a cattle, a horse, or a sheep), an animal wild in nature (e.g., a deer, a fox, a wolf, or a lynx), or a primate (e.g., a monkey or a human being). The control protein may comprise a dimer of two members, and each member may comprise a light chain and a heavy chain forming a targeting moiety specifically binding to a tumor antigen. For example, the tumor antigen may be identical to that bound by the targeting moiety comprised in the proteinaceous heterodimer. In some embodiments, the heavy chain of each member further comprises an immunoregulator at its C-terminus. For example, the immunoregulator may be identical to that comprised in the proteinaceous heterodimer.

In some embodiments, the present disclosure provides a heterodimer protein, comprising a first member (e.g., a polypeptide) and a second member (e.g., a polypeptide) different from said first member. The first member may comprise a targeting moiety capable of binding to a tumor associated antigen, a cancer cell surface marker or a cancer cell associated marker. The second member may comprise an Fc region of an immunoglobulin and an interferon, an interleukin, or any other immunoregulator.

In some embodiments, the Fc region of the immunoglobulin is chemically coupled to the interferon, the interleukin, or said any other immunoregulator. For example, they could be coupled with a linker. The linker may be a polypeptide linker, which may comprise several to tens of amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. In some embodiments, the linker may comprise an amino acid sequence as set forth in SEQ ID NO: 27, SEQ ID NO: 77, SEQ ID NO: 78, or SEQ ID NO: 79. In some embodiments, the linker is resistant to proteolysis or substantially resistant to proteolysis.

Examples of immunoregulator include, but are not limited to, recombinant, synthetic and/or natural preparations of cytokines, granulocyte colony-stimulating factors (G-CSF), interferons, lymphokines, tumor necrosis factors, imiquimod, cellular membrane fractions from bacteria, chemokines, interleukins, cytosine phosphate-guanosine (CpG) oligodeoxynucleotides, and glucans. In some embodiments, the interferon is selected from the group consisting of type I interferon, type II interferon and type III interferon, e.g., interferon α, interferon β or interferon λ. For example, the interferon may be mouse interferon β, human interferon β, mouse interferon α4, human interferon α2, or human interferon λ. In some embodiments, the interleukin is selected from the group consisting of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and IL-36. For example the interleukin may be interleukin 10, interleukin 2, and/or super interleukin 2.

In some embodiments, the targeting moiety is an antibody capable of binding to a tumor associated antigen. In some embodiments, the targeting moiety is capable of specifically binding to a cancer cell surface marker or a cancer cell associated marker. For example, the targeting moiety may be an antibody specifically binding to an EGFR family member, such as an antibody specifically binding to EGFR (e.g., Cetuximab); or an antibody specifically binding to Her-2 (e.g., Trastuzumab). In some embodiments, the targeting moiety is a marker capable of specifically binding to a target selected from the group consisting of EGFR, HER2/neu, HER4, HER3, MUC-1, G250, mesothelin, gp100, CS1, tyrosinase and MAGE. In some embodiments, the targeting moiety is or comprises an antibody selected from the group consisting of panitumumab, nimotuzumab, Zalutumumab, Necitumumab, ABT-806, Sym004, pertuzumab, margetuximab, patritumab, rituximab, ofatumumab, obinutuzumab, ocrelizumab, ibritumoma, tositumomab, ocaratuzumab, veltuzumab, RTXM-83, alemtuzumab, gemtuzumab, daratumumab, epratuzumab, brentuximab, rilotumumab, ranibizumab, ramucirumab, bevacizumab, catumaxomab, Dalotuzumab, Ganitumab, Gemtuxumab, girentuximab, WX-G250, CC49, T84.66, labetuzumab, anetumab, hu7D9.v3, YYP-218, YP-223, YP-3, SD1, SD2, 111In-SS1-scFvSA, MDX-1382, RG-7787, MDX-1459, TF-10, m170, PankoMab, HmAb16, Elotuzumab, and fragments thereof. In some embodiments, the targeting moiety is a single chain antibody, and it may comprise CDRs and/or variable regions of an antibody selected from the group consisting of Cetuximab, Trastuzumab, Rituximab, Ibritumomab, tositumomab, panitumumab, nimotuzumab, Zalutumumab, Necitumumab, ABT-806, Sym004, Pertuzumab, margetuximab, MAGE-101, patritumab, ofatumumab, obinutuzumab, ocrelizumab, ibritumoma, ocaratuzumab, veltuzumab, RTXM-83, Campath-1H (Alemtuzumab), Mylotarg™ (Gemtuzumab, directed to CD33), daratumumab, epratuzumab, brentuximab, rilotumumab, ranibizumab, ramucirumab, Bevacizumab (Avastin™), catumaxomab, Dalotuzumab, Ganitumab, girentuximab (directed to G250), WX-G250 (directed to G250), CC49(directed to TAG-72), T84.66 (directed to CEA), labetuzumab (directed to CEA), anetumab (directed to mesothelin), hu7D9.v3 (directed to mesothelin), YYP-218, YP-223, YP-3, SD1, SD2, 111In-SS1-scFvSA, MDX-1382, RG-7787, MDX-1459, TF-10, m170 (directed to MUC1), PankoMab (directed to MUC1), HmAb16 (directed to MUC1) and Elotuzumab (directed to CS1).

In some embodiments, the targeting moiety is or comprises an antibody selected from the group consisting of Rituxan, IF5, B1, 1H4, CD19, B4, B43, FVS191, hLL2, LL2, RFB4, M195, HuM195, AT13/5, HERCEPTIN®, 4D5, HuCC49, and fragments thereof. In some embodiments, the targeting moiety is or comprises an antibody capable of binding to EGFR family member(s). In some embodiments, the antibody capable of binding to EGFR family member(s) is selected from the group consisting of C6. 5, C6ML3-9, C6MH3-B1, C6-B1D2, F5, HER3.A5, HER3. F4, HER3. H1, HER3. H3, HER3. E12, HER3. B12, EGFR. E12, EGFR. C10, EGFR. B11, EGFR. E8, HER4. B4, HER4. G4, HER4. F4, HER4. A8, HER4. B6, HER4. D4, HER4. D7, HER4. D1U, HER4. D12, HER4. E3, HER4. E7, HER4. F8 and HER4.C7. In some embodiments, the targeting moiety is or comprises the antibody Cetuximab, Trastuzumab, Pertuzumab, or Mab806. In some embodiments, the targeting moiety is an antibody comprising point mutations S354C and/or T366W at positions corresponding to position 354 and/or 366 of the heavy chain of Cetuximab, Trastuzumab, Pertuzumab, or Mab806. The point mutations may be comprised in the (ii) heavy chain of the proteinaceous heterodimer or the heavy chain constant region of the first member of the heterodimer protein.

In some embodiments, the antibody capable of binding to a tumor associated antigen comprises the 3 CDR sequences in heavy chain variable region (VH) and/or the 3 CDR sequences in light chain variable region (VL) of Cetuximab. Trastuzumab, Mab806, or Pertuzumab. In some cases, the antibody may comprise VH and/or VL sequences of Cetuximab, Trastuzumab, Mab806, or Pertuzumab. For example, the antibody may comprise a heavy chain and a light chain, wherein amino acid sequences of its VL may be as set forth in SEQ ID NO:29, and/or amino acid sequences of its VH may be as set forth in SEQ ID NO:30. In another example, the antibody may comprise a heavy chain and a light chain, wherein amino acid sequences of the three CDRs in its VL may be as set forth in SEQ ID NO:31(CDR-L1), SEQ ID NO:32(CDR-L2) and SEQ ID NO:33(CDR-L3), respectively, and/or amino acid sequences of the three CDRs in its VH may be as set forth in SEQ ID NO:34(CDR-H1), SEQ ID NO:35(CDR-H2) and SEQ ID NO:36(CDR-H3), respectively. In a further example, the antibody may comprise a heavy chain and a light chain, wherein amino acid sequences of its VL may be as set forth in SEQ ID NO:37, and/or amino acid sequences of its VH may be as set forth in SEQ ID NO:38. In another example, the antibody may comprise a heavy chain and a light chain, wherein amino acid sequences of the three CDRs in its VL may be as set forth in SEQ ID NO:39(CDR-L1), SEQ ID NO:40(CDR-L2) and SEQ ID NO:41(CDR-L3), respectively, and/or amino acid sequences of the three CDRs in its VH may be as set forth in SEQ ID NO:42(CDR-H1), SEQ ID NO:43(CDR-H2) and SEQ ID NO:44(CDR-H3), respectively. In some embodiments, the antibody may comprise a heavy chain and a light chain, wherein amino acid sequences of its VL may be as set forth in SEQ ID NO:58, and/or amino acid sequences of its VH may be as set forth in SEQ ID NO:57. In one example, the antibody may comprise a heavy chain and a light chain, wherein amino acid sequences of the three CDRs in its VL may be as set forth in SEQ ID NO:62(CDR-L1), SEQ ID NO:63(CDR-L2) and SEQ ID NO:64(CDR-L3), respectively, and/or amino acid sequences of the three CDRs in its VH may be as set forth in SEQ ID NO:59(CDR-H1), SEQ ID NO:60(CDR-H2) and SEQ ID NO:61(CDR-H3), respectively. In a further example, the antibody may comprise a heavy chain and a light chain, wherein amino acid sequences of its VL may be as set forth in SEQ ID NO:69, and/or amino acid sequences of its VH may be as set forth in SEQ ID NO:70. In another example, the antibody may comprise a heavy chain and a light chain, wherein amino acid sequences of the three CDRs in its VL may be as set forth in SEQ ID NO:71(CDR-L1), SEQ ID NO:72(CDR-L2) and SEQ ID NO:73(CDR-L3), respectively, and/or amino acid sequences of the three CDRs in its VH may be as set forth in SEQ ID NO:74(CDR-H1), SEQ ID NO:75(CDR-H2) and SEQ ID NO:76(CDR-H3), respectively. In some embodiments, the antibody comprises point mutations S354C and/or T366W at positions corresponding to position 354 and/or position 366 of the heavy chain of Cetuximab, Trastuzumab, Pertuzumab, or Mab806.

In some embodiments, the antibody capable of binding to a tumor associated antigen is or comprises an antibody selected from the group consisting of single chain Fv (ScFv), Fab, (Fab')2, (ScFv)2 and full length immunoglobulins.

In some embodiments, the antibody capable of binding to a tumor associated antigen comprises: i) a light chain having an amino acid sequence as set forth in SEQ ID NO:11, and/or ii) a heavy chain having an amino acid sequence as set forth in SEQ ID NO:13. In another example, the antibody capable of binding to a tumor associated antigen may comprise: i) a light chain having an amino acid sequence as set forth in SEQ ID NO:15, and/or ii) a heavy chain having an amino acid sequence as set forth in SEQ ID NO:17. In another example, the antibody capable of binding to a tumor associated antigen may comprise: i) a light chain having an amino acid sequence as set forth in SEQ ID NO:55, and/or ii) a heavy chain having an amino acid sequence as set forth in SEQ ID NO:53. In another example, the antibody capable of binding to a tumor associated antigen may comprise: i) a light chain having an amino acid sequence as set forth in SEQ ID NO:65, and/or ii) a heavy chain having an amino acid sequence as set forth in SEQ ID NO:67.

In some embodiments, the Fc region of an immunoglobulin comprised in the second member of the heterodimer is selected from a constant region of the following immunoglobulins: IgG1, IgG2, IgG3 and IgG4. In some embodiments, the targeting moiety comprised in the first member of the heterodimer is or comprises an antibody, and the antibody may comprise an Fc region that is from constant region of an immunoglobulin of the same subtype as that for the Fc region comprised in the second member of the heterodimer. For example, the immunoglobulin constant region may comprise an amino acid sequence as set forth in SEQ ID NO:45, SEQ ID NO:46, SEQ ID NO:47, SEQ ID NO:48, or homologues thereof having at least 50%, at least 60%, at least 70%, at least 80%, at least 90%, at least 95%, at least 98%, at or at least 99% amino acid sequence identity thereto. In some embodiments, the sequence identity of the homologue is at least 80%, or at least 90%.

In some embodiments, the immunoglobulin Fc region in the second member of the heterodimer comprises an amino acid sequence identical to that in the constant region of immunoglobulin γ1 (IgG1). In some embodiments, the IgG1 is human IgG1. In some embodiments, the immunoglobulin Fc region in the second member of the heterodimer comprises an amino acid sequence having point mutations Y349C, T366S, L368A and/or Y407V at positions corresponding to positions 349, 366, 368 and/or 407 of human IgG1 constant region, when compared to the amino acid sequence of human IgG1 constant region.

In some embodiments, the second member of the heterodimer comprises an amino acid sequence as set forth in SEQ ID NO:1, SEQ ID NO:3, SEQ ID NO:5, SEQ ID NO:7, SEQ ID NO:9, SEQ ID NO:49, SEQ ID NO:51, or homologues thereof having at least 50%, at least 60%, at least 70%, at least 80%, at least 90%, at least 95%, at least 98%, at or at least 99% amino acid sequence identity thereto. In some embodiments, the sequence identity of the homologue is at least 80%, or at least 90%. In some embodiments, the targeting moiety is or comprises a molecule capable of specifically or preferentially binding to a marker expressed by a target cell (e.g., a marker expressed on the surface of a target cell) or a marker associated with a target cell. Although the target cell may virtually be any type of cell, it may in particular relate to cells associated with a disease or a disorder characterized by cell over-proliferation (i.e., hyper-proliferation disorders). Examples of hyper-proliferative diseases include but are not limited to psoriasis, neutral leukocytosis, polycythemia, thrombocytosis and cancer.

Further non-limiting examples of hyper-proliferative disorders (e.g., those characterized as cancer) include solid tumors, such as cancers of the breast, respiratory tract, brain, reproductive organs, digestive tract, urinary tract, eye, liver, skin, head and neck, thyroid, parathyroid and their distant metastases. Additional examples of hyper-proliferative disorders also include lymphomas, sarcomas, and leukemias. Non-limiting examples of breast cancer include invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypothalamic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

In some embodiments, the targeting moiety is a moiety that binds a cancer marker (e.g., a tumor associated antigen). These markers are not necessarily unique to cancer cells, but can also be effective where the expression of the marker is elevated in a cancer cell (as compared to normal healthy cells) or where the marker is not present at comparable levels in surrounding tissues (especially when the proteinaceous heterodimer or heterodimer protein of the present disclosure is delivered locally).

Examples of cancer markers include, but are not limited to, the tumor marker recognized by the ND4 monoclonal antibody. This marker is found on poorly differentiated colorectal cancer, as well as gastrointestinal neuroendocrine tumors (see, e.g., Tobi et al. (1998) Cancer Detection and Prevention, 22(2): 147-152). Other examples of targets for cancer immunotherapy include membrane bound complement regulatory glycoprotein, such as CD46, CD55 and CD59, which have been found to be expressed on most tumor cells in vivo and in vitro. Human mucins (e.g. MUC1) are also examples of tumor markers, as are gp100, tyrosinase, and MAGE, which are found in melanoma. Wild-type Wilms' tumor gene WT1 is expressed at high levels not only in most of acute myelocytic, acute lymphocytic, and chronic myelocytic leukemia, but also in various types of solid tumors including lung cancer.

Acute lymphocytic leukemia has been characterized by the tumor-associated antigens (TAAs) HLA-Dr, CD1, CD2, CD5, CD7, CD19, and CD20. Acute myelogenous leukemia has been characterized by the TAAs HLA-Dr, CD7, CD13, CD14, CD15, CD33, and CD34. Breast cancer has been characterized by the markers EGFR, HER2, MUC1, Tag-72. Various carcinomas have been characterized by the markers MUC1, TAG-72, and CEA. Chronic lymphocytic leukemia has been characterized by the markers CD3, CD19, CD20, CD21, CD25, and HLA-DR. Hairy cell leukemia has been characterized by the markers CD19, CD20, CD21, CD25. Hodgkin's disease has been characterized by the Leu-M1 marker. Various melanomas have been characterized by the HMB 45 marker. Non-hodgkins lymphomas have been characterized by the CD20, CD19, and 1a marker. And various prostate cancers have been characterized by the PSMA and SE10 markers.

In some embodiments, tumor cells may display unusual antigens that are either inappropriate for the cell type and/or its environment, or are only normally present during the organisms' development (e.g. fetal antigens). Examples of such antigens include the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. GD2 is thus a convenient tumor-specific target for immunotherapies.

Other kinds of tumor cells may display cell surface receptors that are rare or absent on the surfaces of healthy cells, and which are responsible for activating cellular signaling pathways that cause the unregulated growth and division of the tumor cell. Examples include (ErbB2) HER2/neu, a constitutively active cell surface receptor that is produced at abnormally high levels on the surface of breast cancer tumor cells. Other useful examples of targets include, but are not limited to CD20, CD52, CD33, epidermal growth factor receptor and the like.

Any of the markers discussed above may be targeted by the targeting moiety comprised in the heterodimer of the present disclosure. In some embodiments, the targeted marker is one or more of a member of the EGFR family (e.g., HER2, HER3, EGFR, HER4), CD1, CD2, CD3, CD5, CD7, CD13, CD14, CD15, CD19, CD20, CD21, CD23, CD25, CD33, CD34, CD38, 5E10, CEA, HLA-DR, HM 1. 24, HMB 45, 1a, Leu-M1, MUC1, PMSA, TAG-72, phosphatidylserine, CS1, etc.

In one aspect, the present disclosure provides an isolated polynucleotide encoding a proteinaceous heterodimer of the present disclosure, a member thereof, or fragments thereof. In some embodiments, the present disclosure provides an isolated polynucleotide encoding a heterodimer protein of the present disclosure, a member thereof, or fragments thereof. The polynucleotide may be synthesized using recombinant techniques well known in the art. For example, the polynucleotide may be synthesized by use of an automated DNA synthesizer.

Standard recombinant DNA and molecular cloning techniques include those described by Sambrook, J, Fritsch, E. F. and Maniatis, T *Molecular Cloning: A Laboratory Manual*; Cold Spring Harbor Laboratory Press: Cold Spring Harbor, (1989) (Maniatis) and by T. J. Silhavy, M L. Bennan, and L. W. Enquist, *Experiments with Gene Fusions*, Cold Spring Harbor Laboratory, Cold Spring Harbor, N.Y. (1984) and by Ausubel, F. M et al., *Current Protocols in Molecular Biology*, pub. by Greene Publishing Assoc. and Wiley-Interscience (1987). Briefly, the subject nucleic acids can be prepared from genomic DNA fragments, cDNAs, and RNAs, all of which can be extracted directly from a cell or recombinantly produced by various amplification processes including but not limited to PCR and RT-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. See for example, Matteuci et al., *Tet. Lett.* 521:719 (1980); U.S. Pat. No. 4,500,707 to Caruthers et al.; and U.S. Pat. Nos. 5,436,327 and 5,700,637 to Southern et al. In a further aspect, the present disclosure provides a vector comprising an isolated polynucleotide of the present disclosure. The vector may be any linear nucleic acids, plasmids, phagemids, cosmids, RNA vectors, viral vectors and the like. Non-limiting examples of a viral vector may include a retrovirus, an adenovirus and an adeno-associated virus. In some embodiments, the vector is an expression vector, e.g. a phage display vector.

An expression vector may be suitable for use in particular types of host cells and not others. For example, the expression vector can be introduced into the host organism, which is then monitored for viability and expression of any genes/polynucleotides contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by a variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other examples of transformation methods include microinjection, DEAE dextran mediated transformation, and heat shock in the presence of lithium acetate. Lipid complexes, liposomes, and dendrimers may also be employed to transfect the host cells.

Upon introduction of the heterologous sequence into a host cell, a variety of methods can be practiced to identify the host cells into which the subject vectors have been introduced. One exemplary selection method involves subculturing individual cells to form individual colonies, followed by testing for expression of the desired protein product. Another method entails selecting host cells containing the heterologous sequence based upon phenotypic traits conferred through the expression of selectable marker genes contained within the expression vector.

For example, the introduction of various heterologous sequences of the disclosure into a host cell can be confirmed by methods such as PCR, Southern blot or Northern blot hybridization. For example, nucleic acids can be prepared from the resultant host cells, and the specific sequences of interest can be amplified by PCR using primers specific for the sequences of interest. The amplified product is subjected to agarose gel electrophoresis, polyacrylamide gel electrophoresis or capillary electrophoresis, followed by staining with ethidium bromide, SYBR Green solution or the like, or detection of DNA with a UV detection. Alternatively, nucleic acid probes specific for the sequences of interest can be employed in a hybridization reaction. The expression of a specific gene sequence can be ascertained by detecting the corresponding mRNA via reverse-transcription coupled with PCR, Northern blot hybridization, or by immunoassays using antibodies reactive with the encoded gene product. Exemplary immunoassays include but are not limited to ELISA, radioimmunoassays, and sandwich immunoassays.

Furthermore, the introduction of various heterologous sequences of the disclosure into a host cell can be confirmed by the enzymatic activity of an enzyme (e.g., an enzymatic marker) that the heterologous sequence encodes. The enzyme can be assayed by a variety of methods known in the art. In general, the enzymatic activity can be ascertained by the formation of the product or conversion of a substrate of an enzymatic reaction that is under investigation. The reaction can take place in vitro or in vivo.

In another aspect, the present disclosure provides a cell (e.g., a host cell) comprising a polynucleotide or a vector described elsewhere herein, and/or capable of expressing the proteinaceous heterodimer of the present disclosure and/or the isolated polynucleotide encoding the proteinaceous heterodimer. In some embodiments, the cell expresses the heterodimer protein of the present disclosure and/or the isolated polynucleotide encoding the heterodimer protein. The cell may be a eukaryotic cell or a prokaryotic cell. An appropriate cell may be transformed or transfected with the polynucleotide or vector of the present disclosure, and utilized for the expression and/or secretion of the heterodimer protein. For example, the cell may be E. coli cells, other bacterial host cells, yeast cells, or various higher eukaryotic cells (e.g., immortal hybridoma cells, NSO myeloma cells, 293 cells, Chinese hamster ovary cells, HeLa cells, COS cells, etc.). In some embodiments, polynucleotides encoding the proteinaceous heterodimer (e.g., a heterodimer protein) are operably connected to an expression control sequence suitable for expression in specific host cells.

Method for Preparing Proteinaceous Heterodimers

In one aspect, the present disclosure provides methods for producing proteinaceous heterodimers. In some embodiments, the method comprises the following steps:

(1) providing one member of the heterodimer, wherein the one member comprises (i) a light chain and (ii) a heavy chain complexed to form a targeting moiety exhibiting binding specificity to a tumor antigen;
(2) providing one other member of said heterodimer, wherein the one other member comprises a polypeptide comprising, from N-terminus to C-terminus, an immunoregulator fused to a heavy chain fragment, wherein the heavy chain fragment complexes with the heavy chain (ii) to form the heterodimer; and
3) obtaining the proteinaceous heterodimer.

In some embodiments, the method for producing proteinaceous heterodimers comprises the steps of: culturing a host cell of the present disclosure under conditions to effect expression of the heterodimer, and harvesting the expressed heterodimer.

In some embodiments, the present disclosure provides a method for producing heterodimer proteins of the present disclosure. In some embodiments, the method comprises the following steps:

(1) providing a first member (e.g., a first polypeptide), wherein the first member comprises a targeting moiety capable of binding to a tumor associated antigen, a cancer cell surface marker or a cancer cell associated marker;
(2) providing a second member (e.g., a second polypeptide), wherein the second member comprises Fc region of an immunoglobulin and an interferon, an interleukin, or any other immunoregulator; and
(3) obtaining the protein heterodimer.

In some embodiments, the method for producing heterodimer proteins of the present disclosure comprises the steps of: culturing a host cell of the present disclosure under conditions to effect expression of the heterodimer protein, and harvesting the expressed heterodimer protein.

In some embodiments, the method further comprises the steps of isolating and/or purifying the proteinaceous heterodimer or heterodimer proteins.

In some embodiments, the method further comprises the steps of transfecting/transforming host cells with polynucleotides/vectors encoding/expressing the heterodimer of the present disclosure, one or more members thereof, or fragments thereof.

In some embodiments, the proteinaceous heterodimer or heterodimer protein of the present disclosure is produced by expressing a vector in a cell under conditions suitable for protein expression.

Factors that may vary among suitable conditions for protein expression include factors such as incubation time, temperature, and medium, and may depend on cell type and will be readily determined by one of ordinary skill in the art.

In some embodiments, during the process of producing the proteinaceous heterodimer or heterodimer protein of the present disclosure, the host cells are grown in cultures, and in any apparatus that may be used to grow cultures, including fermenters. Cells may be grown as monolayers or attached to a surface. Alternatively, the host cells may be grown in suspension. The cells can be grown in a culture medium that is serum-free. The media can be a commercially available media, such as, but not limited to, Opti-CHO (Invitrogen, Catalogue #12681) supplemented with glutamine, such as 8 mM L-glutamine; RPMI 1640 medium, supplemented with 10% bovine calf serum, 10.5 ng/ml mIL-3 and L-glutamine; or 5% FCS medium.

Pharmaceutical Compositions

In one aspect, the present disclosure provides pharmaceutical compositions. In some embodiments, the pharmaceutical composition comprises an isolated proteinaceous heterodimer (e.g., an isolated heterodimer protein) or an isolated polynucleotide of the present disclosure. The pharmaceutical composition may further comprise a pharmaceutically acceptable excipient. Examples of pharmaceutically acceptable excipients include, but are not limited to inert solid diluents and fillers, diluents, sterile aqueous solution and various organic solvents, permeation enhancers, solubilizers and adjuvants.

In some embodiments, the pharmaceutical composition is formulated for oral administration, intravenous administration, intramuscular administration, in-situ administration at the site of a tumor, inhalation, rectal administration, vaginal administration, transdermal administration or administration via subcutaneous repository.

The pharmaceutical composition may be used for inhibiting tumor growth. For example, the pharmaceutical compositions, medicaments and/or kits may inhibit or delay the development or progress of a disease, may reduce tumor size (and even substantially eliminate tumors), and may alleviate and/or stabilize a disease condition.

Described below are non-limiting exemplary pharmaceutical compositions and methods for preparing the same.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition can further comprise a proteinaceous heterodimer (e.g., a heterodimer protein) according to the present disclosure as an active ingredient and may include a conventional pharmaceutical carrier or excipient. Further, it may include other medicinal or pharmaceutical agents, carriers, adjuvants, etc.

Exemplary parenteral administration forms include, but not limited to, solutions or suspensions of an active proteinaceous heterodimer (e.g., a heterodimer protein) in sterile aqueous solutions, for example, aqueous propylene glycol or dextrose solutions. Such dosage forms can be suitably buffered with salts such as histidine and/or phosphate, if desired.

In some embodiments, the present disclosure provides a pharmaceutical composition for injection containing a proteinaceous heterodimer (e.g., a heterodimer protein) of the present disclosure and a pharmaceutical excipient suitable for injection. Components and amounts of agents in the compositions are as described herein.

The forms in which the pharmaceutical compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline may also be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions can be prepared by incorporating the proteinaceous heterodimer (e.g., heterodimer protein) of the present disclosure in a suitable amount in the appropriate solvent with various other ingredients as enumerated above, as needed, followed by filtered sterilization. Generally, dispersions are prepared by incorporating the various sterilized active ingredients into a sterile vehicle which contains the basic dispersion medium and other ingredients from those enumerated above, as needed or desired. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

In some embodiments, the present disclosure provides a pharmaceutical composition for oral administration containing a proteinaceous heterodimer (e.g., a heterodimer protein) of the disclosure, and a pharmaceutical excipient suitable for oral administration.

In some embodiments, the present disclosure provides a solid pharmaceutical composition for oral administration containing: (i) an amount of a proteinaceous heterodimer (e.g., a heterodimer protein) of the disclosure; optionally (ii) an amount of a second agent; and (iii) a pharmaceutical excipient suitable for oral administration. In some embodiments, the composition further contains: (iv) an amount of a third agent. In some embodiments, amounts of the proteinaceous heterodimer, second agent, and optional third agent are amounts that, alone or in combination, are effective in treating a condition of a subject.

In some embodiments, the pharmaceutical composition may be a liquid pharmaceutical composition suitable for oral consumption. Pharmaceutical compositions of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods typically include the step of bringing the active ingredient into association with the carrier, which constitutes one or more other ingredients. In general, the compositions are prepared by uniformly and intimately admixing the active ingredient with liquid carriers or finely divided solid carriers or both, and then, if necessary, shaping the product into the desired presentation.

The present disclosure further encompasses anhydrous pharmaceutical compositions and dosage forms comprising an active ingredient (e.g., a proteinaceous heterodimer or a heterodimer protein of the present disclosure), since water can facilitate the degradation of some polypeptides. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

A proteinaceous heterodimer (e.g., a heterodimer protein) of the present disclosure can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the disclosure to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel, a coagulated aerosol of synthetic silica, and mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the disclosure include, but are not limited to, hydrophilic surfactants, lipophilic surfactants, and mixtures thereof. A mixture of hydrophilic surfactants may be employed, a mixture of lipophilic surfactants may be employed, or a mixture of at least one hydrophilic surfactant and at least one lipophilic surfactant may be employed.

Surfactants with lower hydrophilic-lipophilic balance (HLB) values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Examples of hydrophilic non-ionic surfactants include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other examples of hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phytosterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In some embodiments, the composition includes a solubilizer to ensure good solubilization and/or dissolution of the proteinaceous heterodimer of the present disclosure and to minimize precipitation of the proteinaceous heterodimer of the present disclosure. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

In some embodiments, the pharmaceutical compositions of the present disclosure may comprise an additional therapeutically and/or pharmaceutically desirable agent. For example, the additional therapeutically and/or pharmaceutically desirable agent may be an anti-tumor agent, including but not limited to alkylating agents (e.g., mechlorethamine, cyclophosphamide, ifosfamide, phenylalanine mustard, melphalen, chlorambucol, uracil mustard, estramustine, thiotepa, busulfan, lomustine, carmustine, streptozocin, dacarbazine, cis-platinum, cisplatin, carboplatin, altretamine, etc.), antimetabolites (e.g. methotrexate, 5-fluoruracil, floxuridine, 5-fluorodeoxyuridine, capecitabine, fludarabine, cytosine arabinoside, 6-mercaptopurine, 6-thioguanine, gemcitabine, cladribine, deoxycoformycin, pentostatin, etc.), antibiotics (e.g. doxorubicin, daunorubicin, idarubicin, valrubicin, mitoxantrone, dactinomycin, mithramycin, plicamycin, mitomycin C, bleomycin, procarbazine, etc.), mitotic inhibitors (e.g. paclitaxel, docetaxel, vinblatine sulfate, vincristine sulfate, vinorelbine sulfate, etc.), chromatin function inhibitors (e.g., topotecan, irinotecan, etoposide, teniposide, etc.), hormones and hormone inhibitors (e.g. diethylstilbesterol, estradiol, estrogen, esterified estrogens, estramustine, tamoxifen, toremifene, anastrozole, letrozole, 17-OH-progesterone, medroxyprogesterone, megestrol acetate, goserelin, leuprolide, testosteraone, methyltestosterone, fluoxmesterone, flutamide, bicalutamide, nilutamide, etc.), inhibitors of synthesis (e.g., aminoglutethimide, ketoconazole, etc.), immunomodulators (e.g., rituxan, Trastuzumab, denileukin diftitox, levamisole, bacillus Calmette-Guerin, interferon alpha-2a, alpha-2b, interleukin-2, aldesleukin, etc.) and other agents such as 1-aspariginase, pegaspasgase, hydroxyurea, leucovorin, mitotane, porfimer, tretinoin, etc.

The pharmaceutical compositions of the present disclosure may comprise a therapeutically effective amount of the active agent (e.g., the proteinaceous heterodimer or a heterodimer protein of the present disclosure). A therapeutically effective amount is an amount of the subject pharmaceutical composition capable of preventing and/or curing (at least partially) a condition or disorder (e.g., cancer) and/or any complications thereof in a subject suffering from or having a risk of developing said condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 50 mg/kg/day; sometimes, the dosage can be even higher. In some embodiments, the dosage applied may be from about 3 mg/kg/day to about 3.5 mg/kg/day, from 3.5 mg/kg/day to about 7.2 mg/kg/day, from about 7.2 mg/kg/day to about 11.0 mg/kg/day, from about 11.0 mg/kg/day to about 15.0 mg/kg/day. In some embodiments, the dosage applied is from about 10 mg/kg/day to about 50 mg/kg/day, for example, from about 20 mg to about 50 mg per day, administered twice/day. It shall be understood that these specific doses may be conveniently adjusted by a skilled person in the art (e.g., a doctor or a pharmacist) based on conditions of a specific patient, formulation, and/or disease.

Medical Use and Methods of Treatment

In one aspect, the present disclosure provides use of the proteinaceous heterodimer (e.g., heterodimer protein), the isolated polynucleotide or the pharmaceutical composition of the present disclosure in the manufacture of a medicament and/or a kit for inhibiting growth of a tumor or a tumor cell.

In some embodiments, the medicament and/or kit is used for specifically and/or preferentially inhibiting growth or differentiation of target cells (e.g., cancer cells) or killing target cells (e.g., cancer cells).

In one aspect, the present disclosure provides a method for inhibiting growth of a tumor or a tumor cell. The method may comprise contacting the tumor or the cell with an effective amount of the proteinaceous heterodimer or heterodimer protein of the present disclosure. In some embodiments, the contacting occurs in vitro. In some embodiments, the contacting occurs in vivo.

In some embodiments, said contacting includes systemically or locally administering the proteinaceous heterodimer (e.g., a heterodimer protein), the pharmacuetical composition or the medicament of the present disclosure to a subject (e.g., a mammal). In some embodiments, said contacting includes administering the proteinaceous heterodimer (e.g., a heterodimer protein), the pharmacuetical composition, or the medicament of the present disclosure directly at the site of a tumor. In some embodiments, the administering is conducted by oral administration, intravenous administration, intramuscular administration, in-situ administration at the site of a tumor, inhalation, rectal administration, vaginal administration, transdermal administration or administration via subcutaneous repository.

In some embodiments, the tumor (e.g., cancer) or tumor cell (e.g., a cancer cell) is or is from a solid tumor. For example, the cancer may be selected from the group consisting of a B cell lymphoma, a lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, an adrenal gland cancer, an osteosarcoma, a chondrosarcoma, a liposarcoma, a testes cancer, and a malignant fibrous histiocytoma.

In some embodiments, the cancer or cancer cell is within the body of a subject, e.g., a cancer or cancer cell within a human or in a non-human animal (e.g., a mammal).

In some embodiments, the mammal is a human. In some embodiments, the mammal is a mouse, a rat, a cat, a dog, a rabbit, a pig, a sheep, a horse, a bovine, a goat, a gerbil, a hamster, a guinea pig, a monkey or any other mammal. Many such mammals may be subjects that are known to the art as preclinical models for certain diseases or disorders, including solid tumors and/or other cancers (e.g., Talmadge et al., 2007 Am. J. Pathol. 170:793; Kerbel, 2003 Canc. Biol. Therap. 2(4 Suppl 1):S134; Man et al., 2007 Canc. Met. Rev. 26:737; Cespedes et al., 2006 Clin. TransL Oncol. 8:318).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EXAMPLES

The examples and preparations provided below further illustrate and exemplify the proteinaceous heterodimer of the present disclosure and methods of using and preparing thereof. It is to be understood that the scope of the present disclosure is not limited in any way by the scope of the following examples and preparations.

Example 1 Modification and Preparation of Polypeptides 1.1 Preparation of Cetuximab Full length amino acid sequences of the heavy chain and light chain of Cetuximab (also known as Erbitux or Erb, which is an antibody against epidermal growth factor receptor EGFR) were obtained, and corresponding DNA sequences encoding these amino acid sequences were obtained using online tool DNAworks (helixweb.nih.gov/dnaworks/). Then, nucleic acid molecules encoding the light chain of Cetuximab (Erb-LC) were synthesized. The amino acid sequence of Erb-LC is as set forth in SEQ ID NO:11, and the corresponding polynucleotide sequence encoding it is as set forth in SEQ ID NO:12. Then, point mutations (S354C, T366W) were introduced into the polynucleotide sequences encoding the Fc region of Cetuximab heavy chain gene, and nucleic acid molecules encoding the modified Cetuximab heavy chain were synthesized (referred to herein as erb-knob), the corresponding polypeptide encoding it was named as Erb-knob. The amino acid sequences of Erb-knob is as set forth in SEQ ID NO:13, and the polynucleotide sequence encoding it is as set forth in SEQ ID NO:14.

1.2 Preparation of Trastuzumab

Full length amino acid sequences of the heavy chain and light chain of Trastuzumab were obtained according to U.S. Pat. No. 7,879,325B2 (incorporated herein by reference). Then, corresponding DNA sequences encoding these amino acid sequences were obtained using online tool DNAworks (helixweb.nih.gov/dnaworks/). Nucleic acid molecules encoding the light chain of Trastuzumab (T-LC) were then synthesized. The amino acid sequence of T-LC is as set forth in SEQ ID NO:15, and the corresponding polynucleotide sequence encoding it is as set forth in SEQ ID NO:16. Then, point mutations (S354C, T366W) were introduced into the polynucleotide sequences encoding the Fc region of Trastuzumab heavy chain gene, and nucleic acid molecules encoding the modified Trastuzumab heavy chain were synthesized (referred to herein as t-knob), the corresponding polypeptide encoding it was named as T-knob. The amino acid sequences of T-knob is as set forth in SEQ ID NO:17, and the polynucleotide sequence encoding it is as set forth in SEQ ID NO:18.

1.3 Preparation of muIFNa4-Fc-Hole

First of all, sequence information of mouse interferon α4 (IFNa4) (NM_010504.2) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (Y349C, T366S, L368A, and Y407V) were introduced into the IgG1-Fc fragment, and the polypeptide obtained thereby is referred to as Fc-hole. Then, a linker sequence "GSGGG" (SEQ ID NO:27) was added to the N-terminus of the Fc-hole, to obtain linker-Fc-hole. The corresponding DNA sequence encoding it was then designed using online tool DNAworks (helixweb.nih.gov/dnaworks/). Polynucleotide sequences encoding mouse IFNa4 were added to the 5' end of the polynucleotide sequences encoding the linker-Fc-hole, thereby obtaining and synthesizing a polynucleotide sequence encoding the fusion protein muIFNa4-Fc-hole. The amino acid sequence of muIFNa4-Fc-hole is as set forth in SEQ ID NO:1, and the polynucleotide sequence encoding it is as set forth in SEQ ID NO:2.

1.4 Preparation of huIFNa2-Fc-Hole

First of all, sequence information of human interferon α2 (IFNa2) (NM_000605.3) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (Y349C, T366S, L368A, and Y407V) were introduced into the IgG1-Fc fragment, and the polypeptide obtained thereby is referred to as Fc-hole. Then, a linker sequence "GSGGG" (SEQ ID NO:27) was added to the N-terminus of the Fc-hole, to obtain linker-Fc-hole. The corresponding DNA sequence encoding it was then designed using online tool DNAworks (helixweb.nih.gov/dnaworks/). Polynucleotide sequences encoding human IFNa2 were added to the 5' end of the polynucleotide sequences encoding the linker-Fc-hole, thereby obtaining and synthesizing a polynucleotide sequence encoding the fusion protein huIFNa2-Fc-hole. The amino acid sequence of huIFNa2-Fc-hole is as set forth in SEQ ID NO:3, and the polynucleotide sequence encoding it is as set forth in SEQ ID NO:4.

1.5 Preparation of muIFNb-Fc-Hole

First of all, sequence information of mouse interferon β (IFNβ)(NM_005018.2) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (Y349C, T366S, L368A, and Y407V) were introduced into the IgG1-Fc fragment, and the polypeptide obtained thereby is referred to as Fc-hole. Then, a linker sequence "GSGGG" (SEQ ID NO:27) was added to the N-terminus of the Fc-hole, to obtain linker-Fc-hole. The corresponding DNA sequence encoding it was then designed using online tool DNAworks (helixweb.nih.gov/dnaworks/). Polynucleotide sequences encoding mouse IFNβ were added to the 5' end of the polynucleotide sequences encoding the linker-Fc-hole, thereby obtaining and synthesizing a polynucleotide sequence encoding the fusion protein muIFNb-Fc-hole. The amino acid sequence of muIFNb-Fc-hole is as set forth in SEQ ID NO:5, and the polynucleotide sequence encoding it is as set forth in SEQ ID NO:6.

1.6 Preparation of huIFNb-Fc-Hole

First of all, sequence information of human interferon β (IFNβ) (EF064725.1) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (Y349C, T366S, L368A, and Y407V) were introduced into the IgG1-Fc fragment, and the polypeptide obtained thereby is referred to as Fc-hole. Then, a linker sequence "GSGGG" (SEQ ID NO:27) was added to the N-terminus of the Fc-hole, to obtain linker-Fc-hole. The corresponding DNA sequence encoding it was then designed using online tool DNAworks (helixweb.nih.gov/dnaworks/). Polynucleotide sequences encoding human IFNβ were added to the 5' end of the polynucleotide sequences encoding the linker-Fc-hole, thereby obtaining and synthesizing a polynucleotide sequence encoding the fusion protein huIFNb-Fc-hole. The amino acid sequence of huIFNb-Fc-hole is as set forth in SEQ ID NO: 9, and the polynucleotide sequence encoding it is as set forth in SEQ ID NO: 10.

1.7 Preparation of huIFNL-Fc-Hole

First of all, sequence information of human interferon λ (IFNL) (BC117482.1) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (Y349C, T366S, L368A, and Y407V) were introduced into the IgG1-Fc fragment, and the polypeptide obtained thereby is referred to as Fc-hole. Then, a linker sequence "GSGGG" (SEQ ID NO:27) was added to the N-terminus of the Fc-hole, to obtain linker-Fc-hole. The corresponding DNA sequence encoding it was then designed using online tool DNAworks (helixweb.nih.gov/dnaworks/). Polynucleotide sequences encoding human IFNL were added to the 5' end of the polynucleotide sequences encoding the linker-Fc-hole, thereby obtaining and synthesizing a polynucleotide sequence encoding the fusion protein huIFNL-Fc-hole. The amino acid sequence of huIFNL-Fc-hole is as set forth in SEQ ID NO: 7, and the polynucleotide sequence encoding it is as set forth in SEQ ID NO: 8.

1.8 Preparation of Control C-Term or N-Term Fusion Proteins

First of all, full length amino acid sequences of Cetuximab light chain and heavy chain were obtained. The corresponding DNA sequences encoding them were then designed using online tool DNAworks (helixweb.nih.gov/dnaworks/), and nucleic acid molecules encoding Cetuximab light chain and heavy chain were synthesized. A linker sequence "SGGGGSGGGGSGGGGSGGGG" (SEQ ID NO:28) was added to the C terminus of the heavy chain, thereby obtaining Cetuximab heavy chain-linker. Then, DNA sequences encoding mouse IFNβ (NM_005018.2) were designed using on-line tool DNAworks (helixweb.nih.gov/dnaworks/). DNA sequences encoding mouse IFNβ were then added to the 3' end of the Cetuximab heavy chain-linker thus obtained, to produce and synthesize polynucleotide sequences encoding the fusion protein ErbHC-muIFNb. The amino acid sequence of ErbHC-muIFNb is as set forth in SEQ ID NO:19, and the polynucleotide sequence encoding it is as set forth in SEQ ID NO:20.

Similarly, full length amino acid sequences of Cetuximab light chain and heavy chain were obtained. The corresponding DNA sequences encoding them were then designed using online tool DNAworks (helixweb.nih.gov/dnaworks/), and nucleic acid molecules encoding Cetuximab light chain and heavy chain were synthesized. A linker sequence "GSGGG" was added to the N terminus of the heavy chain, thereby obtaining linker-Cetuximab heavy chain. Then, DNA sequences encoding human IFN, (BC117482.1) were designed using on-line tool DNAworks (helixweb.nih.gov/dnaworks/). DNA sequences encoding human IFNL were then added to the 5' end of the linker-Cetuximab heavy chain thus obtained, to produce and synthesize polynucleotide sequences encoding the fusion protein IFNL-ErbHC. The amino acid sequence of IFNL-ErbHC is as set forth in SEQ ID NO:21, and the polynucleotide sequence encoding it is as set forth in SEQ ID NO:22.

Full length amino acid sequences of Cetuximab light chain and heavy chain were obtained. The corresponding DNA sequences encoding them were then designed using online tool DNAworks (helixweb.nih.gov/dnaworks/), and nucleic acid molecules encoding Cetuximab light chain and heavy chain were synthesized. A linker sequence "SGGGGSGGGGSGGGGSGGGG" (SEQ ID NO:28) was added to the C terminus of the heavy chain, thereby obtaining Cetuximab heavy chain-linker. Then, DNA sequences encoding human IFNβ (EF064725.1) were designed using on-line tool DNAworks (helixweb.nih.gov/dnaworks/). DNA sequences encoding human IFNβ were then added to the 3' end of the Cetuximab heavy chain-linker thus obtained, to produce and synthesize polynucleotide sequences encoding the fusion protein ErbHC-huIFNb. The amino acid sequence of ErbHC-huIFNb is as set forth in SEQ ID NO:23, and the polynucleotide sequence encoding it is as set forth in SEQ ID NO:24.

Full length amino acid sequences of Cetuximab light chain and heavy chain were obtained. The corresponding DNA sequences encoding them were then designed using online tool DNAworks (helixweb.nih.gov/dnaworks/), and nucleic acid molecules encoding Cetuximab light chain and heavy chain were synthesized. A linker sequence "GSGGG" was added to the N terminus of the heavy chain, thereby obtaining linker-Cetuximab heavy chain. Then, DNA sequences encoding human IFNβ (EF064725.1) were designed using on-line tool DNAworks (helixweb.nih.gov/dnaworks/). DNA sequences encoding human IFNβ were then added to the 5' end of the linker-Cetuximab heavy chain thus obtained, to produce and synthesize polynucleotide sequences encoding the fusion protein huIFNb-ErbHC. The amino acid sequence of huIFNb-ErbHC is as set forth in SEQ ID NO:25, and the polynucleotide sequence encoding it is as set forth in SEQ ID NO:26.

1.9 Preparation of huIL10-Fc-Hole

First of all, sequence information of human interleukin 10 (huIL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (Y349C, T366S, L368A, and Y407V) were introduced into the IgG1-Fc fragment, and the polypeptide obtained thereby is referred to as Fc-hole. Then, a linker sequence "(GGGGS)$_3$" (SEQ ID NO:77) was added to the N-terminus of the Fc-hole, to obtain linker-Fc-hole. The corresponding DNA sequence encoding it was then designed using online tool DNAworks (helixweb.nih.gov/dnaworks/). Polynucleotide sequences encoding huIL10 were added to the 5' end of the polynucleotide sequences encoding the linker-Fc-hole, thereby obtaining and synthesizing a polynucleotide sequence encoding the fusion protein huIL10-Fc-hole. The amino acid sequence of huIL10-Fc-hole is as set forth in SEQ ID NO: 49, and the polynucleotide sequence encoding it is as set forth in SEQ ID NO: 50.

1.10 Preparation of (huIL10)2-Fc-Hole

First of all, sequence information of human interleukin 10 (huIL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (Y349C, T366S, L368A, and Y407V) were introduced into the IgG1-Fc fragment, and the polypeptide obtained thereby is referred to as Fc-hole. Then, a linker sequence "(GGGGS)$_3$" (SEQ ID NO:77) was added to the N-terminus of the Fc-hole, to obtain linker-Fc-hole. The corresponding DNA sequence encoding it was then designed using online tool DNAworks (helixweb.nih.gov/dnaworks/). Then, a linker sequence "(GGGGS)$_3$" (SEQ ID NO:77) was added between two copies of huIL10, to obtain (huIL10)2. Polynucleotide sequences encoding (huIL10)2 were then added to the 5' end of the polynucleotide sequences encoding the linker-Fc-hole, thereby obtaining and synthesizing a polynucleotide sequence encoding the fusion protein (huIL10)2-Fc-hole. The amino acid sequence of (huIL10)2-Fc-hole is as set forth in SEQ ID NO: 51, and the polynucleotide sequence encoding it is as set forth in SEQ ID NO: 52.

1.11 Preparation of Pertuzumab

Full length amino acid sequences of the heavy chain and light chain of Pertuzumab were obtained according to U.S. Pat. No. 7,879,325 (incorporated herein by reference). Then, corresponding DNA sequences encoding these amino acid sequences were obtained using online tool DNAworks (helixweb.nih.gov/dnaworks/). Nucleic acid molecules encoding the light chain of Pertuzumab (P-LC) were then synthesized. The amino acid sequence of P-LC is as set forth in SEQ ID NO:55, and the corresponding polynucleotide sequence encoding it is as set forth in SEQ ID NO:56. Then, point mutations (S354C, T366W) were introduced into the polynucleotide sequences encoding the Fc region of Pertuzumab heavy chain gene, and nucleic acid molecules encoding the modified Pertuzumab heavy chain were synthesized (referred to herein as p-knob), the corresponding polypeptide encoding it was named as P-knob. The amino acid sequences of P-knob is as set forth in SEQ ID NO:53, and the polynucleotide sequence encoding it is as set forth in SEQ ID NO:54.

1.12 Preparation of Mab806

Full length amino acid sequences of the heavy chain and light chain of Mab806 were obtained according to U.S. Pat. No. 7,879,325 (incorporated herein by reference). Then, corresponding DNA sequences encoding these amino acid sequences were obtained using online tool DNAworks (helixweb.nih.gov/dnaworks/). Nucleic acid molecules encoding the light chain of Mab806 (Mab806-LC) were then synthesized. The amino acid sequence of Mab806-LC is as set forth in SEQ ID NO:65, and the corresponding polynucleotide sequence encoding it is as set forth in SEQ ID NO:66. Then, point mutations (S354C, T366W) were introduced into the polynucleotide sequences encoding the Fc region of Mab806 heavy chain gene, and nucleic acid molecules encoding the modified Mab806 heavy chain were synthesized (referred to herein as mab806-knob), the corresponding polypeptide encoding it was named as Mab806-knob. The amino acid sequences of Mab806-knob is as set forth in SEQ ID NO:67, and the polynucleotide sequence encoding it is as set forth in SEQ ID NO:68.

Example 2 Construction of Recombinant Plasmids

The nucleic acid molecules (encoding huIFNb-ErbHC, ErbHC-huIFNb, IFNL-ErbHC, ErbHC-muIFNb, T-knob, Trastuzumab light chain (named as T-LC), Erb-knob, Cetuximab light chain (named as Erb-LC), muIFNa4-Fc-hole, huIFNa2-Fc-hole, muIFNb-Fc-hole, huIFNb-Fc-hole, huIFNL-Fc-hole, huIL10-Fc-hole, (huIL10)2-Fc-hole, Pertuzumab light chain (named as P-LC), P-knob, Mab806 light chain (named as Mab806-LC), and Mab806-knob, respectively) obtained according to Example 1 were digested with HindIII and EcoRI (Takara), and then sub-cloned into the vector pcDNA4/myc-HisA (Invitrogen, V863-20), respectively. The plasmids obtained were verified by sequencing, and the correct recombinant plasmids were named as: pcDNA4-huIFNb-ErbHC, pcDNA4-ErbHC-huIFNb, pcDNA4-huIFNL-ErbHC, pcDNA4-ErbHC-muIFNb, pcDNA4-T-knob, pcDNA4-TLC, pcDNA4-Erb-knob, pcDNA4-ErbLC, pcDNA4-muIFNa4-Fc-hole, pcDNA4-huIFNa2-Fc-hole, pcDNA4-muIFNb-Fc-hole, pcDNA4-huIFNb-Fc-hole, pcDNA4-huIFNL-Fc-hole, pcDNA4-huIL10-Fc-hole, pcDNA4-(huIL10)2-Fc-hole, pcDNA4-PLC, pcDNA4-P-knob, pcDNA4-Mab806-LC, and pcDNA4-Mab806-knob, respectively.

Example 3 Expression and Purification of Proteinaceous Heterodimers

Two days before transfection, 12×600 mL suspension domesticated HEK293 (ATCC, CRL-1573™) cells were prepared for transient transfection, the cells were seeded at a density of $0.8×10^6$ cells/mL. Two days later, three aliquots of cell suspension were centrifuged, and then resuspended in 600 mL Freestyle293 culture medium.

Figure 10:
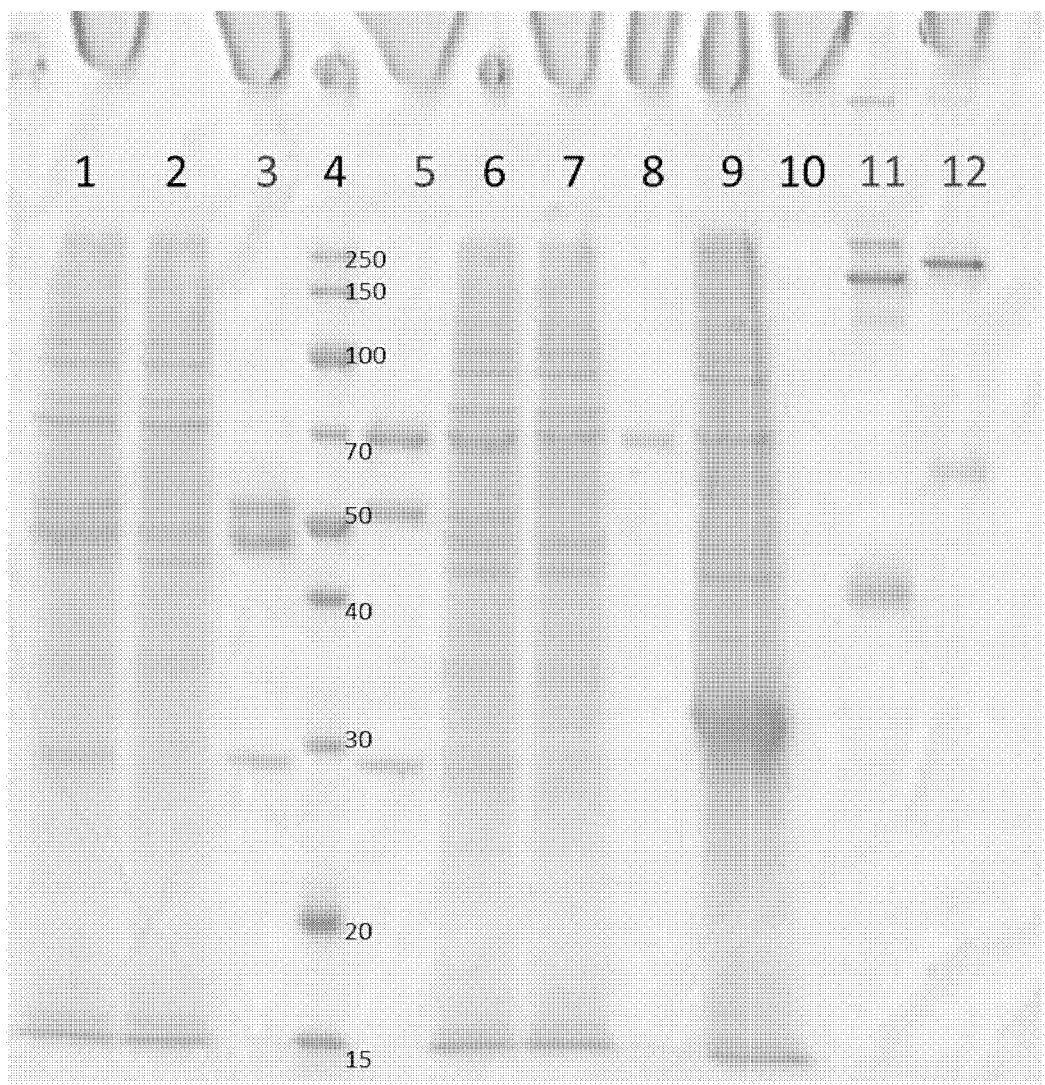
FIG. 10 illustrates SDS PAGE assay results for the purification of Erb-huIL10 and Erb-(huIL10)2 heterodimers. Lane 1:Erb-huIL10 (original sample); Lane 2: Erb-huIL10 (flow-through); Lane 3: Erb-huIL10 (eluted); Lane 4: Protein Marker; Lane 5: Erb-(huIL10)2 (eluted); Lane 6: Erb-(huIL10)2 (original); Lane 7: Erb-(huIL10)2 (flow through); Lane 8: Standard; Lane 9: Control; Lane 10: Blank; Lane 11: Erb-huIL10 (eluted, non-reduced); Lane 12: Erb-(huIL10)2 (eluted, non-reduced).

The recombinant expression vectors obtained from Example 2 were divided into the following groups:

Group 1: pcDNA4-Erb-knob (200 µg)+pcDNA4-ErbLC (200 µg)+pcDNA4-muIFNa4-Fc-hole (200 µg);
Group 2: pcDNA4-Erb-knob (200 µg)+pcDNA4-ErbCL (200 µg)+pcDNA4-huIFNa2-Fc-hole (200 µg);
Group 3: pcDNA4-Erb-knob (200 µg)+pcDNA4-ErbLC (200 µg)+pcDNA4-muIFNb-Fe-hole (200 µg);
Group 4: pcDNA4-Erb-knob (200 µg)+pcDNA4-ErbLC (200 µg)+pcDNA4-huIFNb-Fc-hole (200 µg);
Group 5: pcDNA4-Erb-knob (200 µg)+pcDNA4-ErbLC (200 µg)+pcDNA4-huIFNL-Fc-hole (200 µg);
Group 6: pcDNA4-T-knob (200 µg)+pcDNA4-TLC (200 µg)+pcDNA4-huIFNa2-Fc-hole (200 µg);
Group 7: pcDNA4-T-knob (200 µg)+pcDNA4-TCL (200 µg)+pcDNA4-huIFNb-Fc-hole (200 µg);
Group 8: pcDNA4-T-knob (200 µg)+pcDNA4-TLC (200 µg)+pcDNA4-(huIL10)2-Fc-hole (200 µg);
Group 9: pcDNA4-Erb-knob (200 µg)+pcDNA4-ErbLC (200 µg)+pcDNA4-huIL10-Fc-hole (200 µg);
Group 10: pcDNA4-Erb-knob (200 µg)+pcDNA4-ErbLC (200 µg)+pcDNA4-(huIL10)2-Fc-hole (200 µg);
Group 11: pcDNA4-Mab806-knob (200 µg)+pcDNA4-Mab806-LC (200 µg)+pcDNA4-(huIL10)2-Fe-hole (200 µg);
Group 12: pcDNA4-P-knob (200 µg)+pcDNA4-PLC (200 µg)+pcDNA4-(huIL10)2-Fe-hole (200 µg);

Each group of plasmid mixtures was diluted with 6 mL Freestyle293 medium and PEI (polyethylenimine) solution was added to perform transfection. Each group of plasmid/PEI mixtures was added into 600 mL cell suspension, respectively, which was then cultured at 37° C., 10% $CO_2$, 90 rpm, the medium was supplemented with 50 µg/L IGF-1 (insuline-like growth factor I). Four hours later, the culture was supplemented with 600 mL EX293 medium, 2 mM glutamine and 50 µg/L IGF-1, and cultured at 135 rpm. After 24 hours, 3.8 mM VPA was added. 5-6 days later, supernatant of 5×1200 mL cells was collected, and crude proteinaceous heterodimer samples were purified by Protein A affinity chromatography. The samples obtained were examined first with SDS-PAGE, and the target bands were clearly seen (examples are shown in FIG. 10). The proteinaceous heterodimers thus obtained are named as (from Group 1 to Group 12, respectively): Erb-muIFNa4, Erb-huIFNa2, Erb-muIFNb Erb-huIFNb Erb-huIFNL, Tmab-huIFNa2, Tmab-huIFNb, Tmab-(huIL10)2, Erb-huIL10, Erb-(huIL10)2, Mab806-(huIL10)2, and Pmab-(huIL10)2.

Example 4 Expression Yield of the Proteinaceous Heterodimers 4.1 Comparison of the Expression of the Heterodimer Erb-muIFNb with the C-Terminal Fusion Protein ErbHC-muIFNb Two days before transfection, 2×100 mL suspension domesticated HEK293 (ATCC, CRL-1573™) cells were prepared for transient transfection, the cells were seeded at a density of $0.8×10^6$ cells/mL. Two days later, cell suspension was centrifuged, and then resuspended in 100 mL Freestyle293 culture medium. The expression plasmids were divided into "heterodimer group" and "C-terminal fusion protein group," wherein the heterodimer group comprised: pcDNA4-Erb-knob (33 µg)+pcDNA4-ErbLC (33 µg)+pcDNA4-muIFNb-Fc-hole (33 µg); and the C-terminal fusion protein group comprised: pcDNA4-Erb-LC (50 µg)+pcDNA4-ErbHC-muIFNb (50 µg). Each group of plasmids mixture was diluted with 1 mL Freestyle293 medium and PEI (polyethylenimine) solution was added to perform transfection. Each group of plasmids/PEI mixture was added into 100 mL cell suspension, respectively, and it was then cultured at 37° C., 10% $CO_2$, 90 rpm, the medium was supplemented with 50 µg/L IGF-1. Four hours later, the culture was supplemented with 100 mL EX293 medium, 2 mM glutamine and 50 µg/L IGF-1, and cultured at 135 rpm. After 24 hours, 3.8 mM VPA was added. 5-6 days later, culture supernatant from the transient expression was collected, and the expression level of the heterodimer and the C-terminal fusion protein was examined by ELISA (enzyme linked immunosorbent assay).

As shown in FIG. 1, the expression yield of Erb-muIFNb heterodimer was 83 mg/L, and the expression yield of the C-terminal fusion protein ErbHC-muIFNb was 3 mg/L.

Similarly, expression yield of the other proteinaceous heterodimers of the present disclosure as well as control C-terminal fusion proteins and/or N-terminal fusion proteins was examined, the results are summarized in Table 1 below:

TABLE 1

| Product | Type | Expression yield |
|---|---|---|
| Erb-muIFNa4 | Heterodimer | 50 mg/L |
| Erb-huIFNa2 | Heterodimer | 55 mg/L |
| Erb-huIFNb | Heterodimer | 15.8 mg/L |
| ErbHC-huIFNb | C-terminal fusion | —* |
| huIFNb-ErbHC | N-terminal fusion | —* |
| Erb-huIFNL | Heterodimer | 70 mg/L |
| IFNL-ErbHC | N-terminal fusion | 42 mg/L |
| Tmab-huIFNa2 | Heterodimer | 50 mg/L |
| Tmab-huIFNb | Heterodimer | 50 mg/L |
| Erb-huIL10 | Heterodimer | 55.2 mg/L |
| Erb-(huIL10)2 | Heterodimer | 35 mg/L |
| Mab806-(huIL10)2 | Heterodimer | 13 mg/L |
| Tmab-(huIL10)2 | Heterodimer | 50 mg/L |
| Pmab-(huIL10)2 | Heterodimer | 32 mg/L |

—*: undetectable

Figure 2:
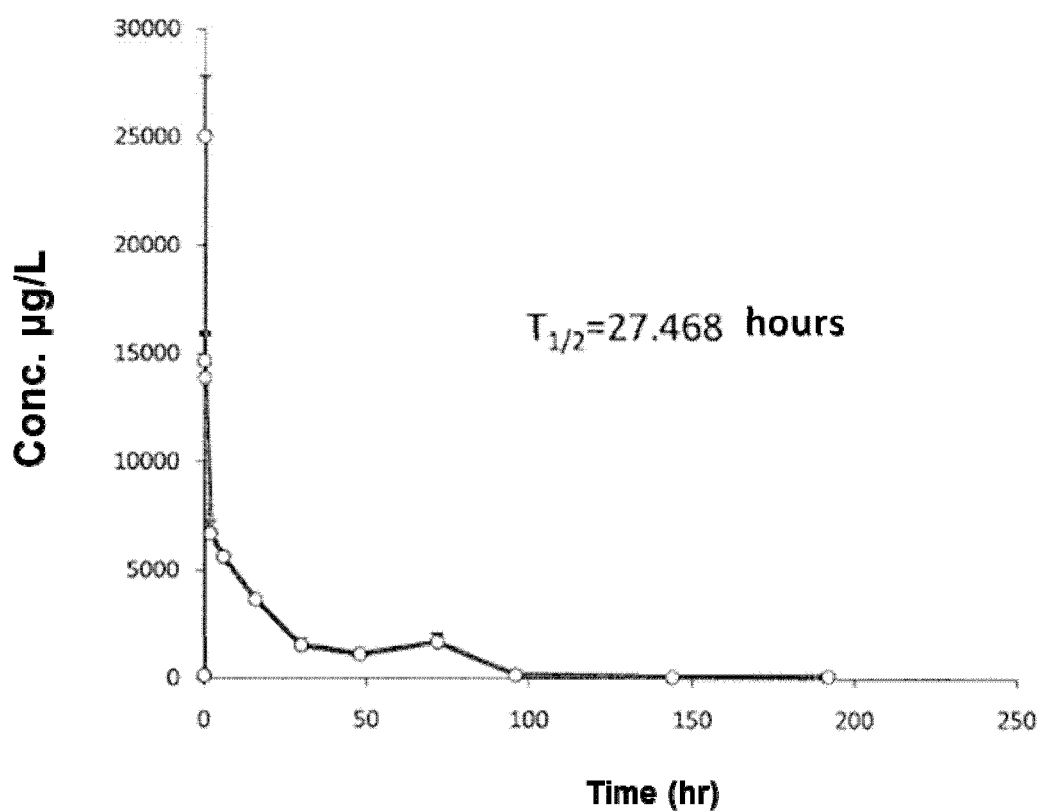
FIG. 2 illustrates results of pharmacokinetic analysis for the heterodimer Erb-huIFNb.

Example 5 In Vivo Stability of the Proteinaceous Heterodimers 5.1 Pharmacokinetic Profile of the Heterodimer Erb-huIFNb 12 Balb/C, female, 8-week old mice were divided into 3 groups (group A/B/C), with 4 mice in each group. 50 µg (2.5 mg/kg) Erb-huIFNb proteinaceous heterodimers were intravenously injected into each mouse, 100 µl of blood were taken at 13 different time points after administration of the heterodimers. At each time point, blood was taken from one group of mice, and the three groups rotated. Serum was isolated, then, concentration of the heterodimers in the serum was determined using ELISA. Briefly, the ELISA assay was performed as follows: plates were coated with mouse-anti-hIgG (Jackson Immuno Research: 209-005-082), then, appropriately diluted serum samples were added. Afterwards, mouse anti-hIENb-biotin (eBioscience: BMS1044BT) was added, and then, streptavidin-HRP (Sigma: S2438) was added for TMB development. Erb-huIFNb was used as standard to obtain a standard curve. WinNolin was used to calculate pharmacokinetic parameters. An average C-T curve obtained is as shown in FIG. 2. The calculated half-life ($T_{1/2}$) for the heterodimer Erb-huIFNb is 27.468 hours, while the $T_{1/2}$ of the C-terminal fusion protein between Erb and huIFNβ is reported to be only 8 hours.

5.2 Pharmacokinetic Profile of the Heterodimer Erb-huIFNL

Figure 3:
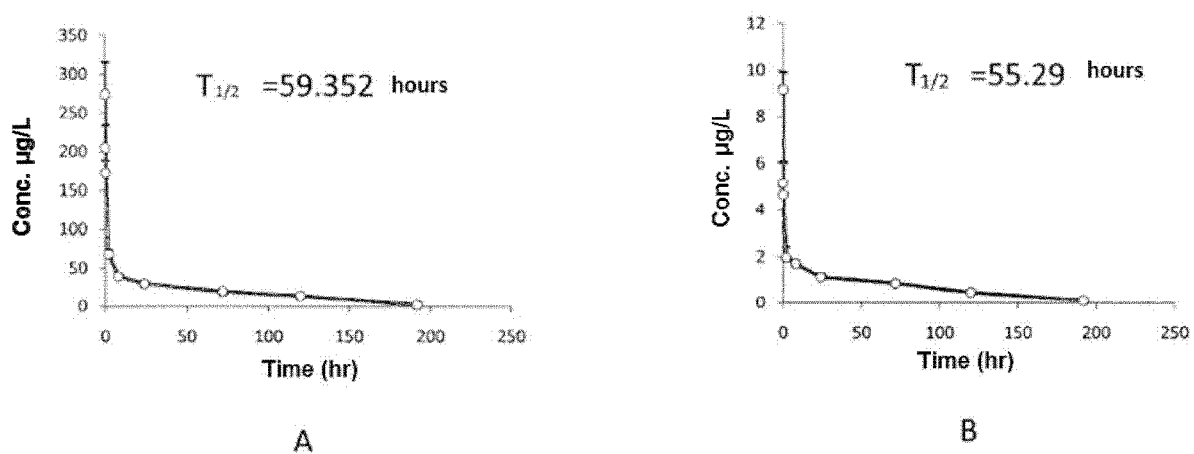
FIG. 3 illustrates results of pharmacokinetic analysis for the heterodimer Erb-huIFNL.

12 Balb/C, female, 8-week old mice were divided into 3 groups (group A/B/C), with 4 mice in each group. 200 µg (10 mg/kg) Erb-huIFNL proteinaceous heterodimers were intravenously injected into each mouse, 1000 of blood were taken at 13 different time points after administration of the heterodimers. At each time point, blood was taken from one group of mice, and the three groups rotated. Serum was isolated, then, concentration of the Fc fragment and the huIFNL in the serum was determined using ELISA, respectively. Briefly, for the Fc fragment, the ELISA assay was performed as follows: plates were coated with anti-hIgG-Fc fragment antibody (Bethyl: A80-104A), then, appropriately diluted serum samples were added. Afterwards, anti-human IgG Fc HRP (Bethyl: A80-104P) was added, and then, TMB development was conducted. For huIFNL, the huIFNL ELISA kit (eBioscience:88-7296) was used. Erb-huIFNL was used as standard to obtain a standard curve. WinNolin was used to calculate pharmacokinetic parameters. An average C-T curve obtained is as shown in FIG. 3. The calculated half-life ($T_{1/2}$) for the heterodimer Erb-huIFNL is 57.308 hours.

5.3 Pharmacokinetic Profile of the Heterodimers Erb-huIL10 and Erb-(huIL10)2

Figure 11:
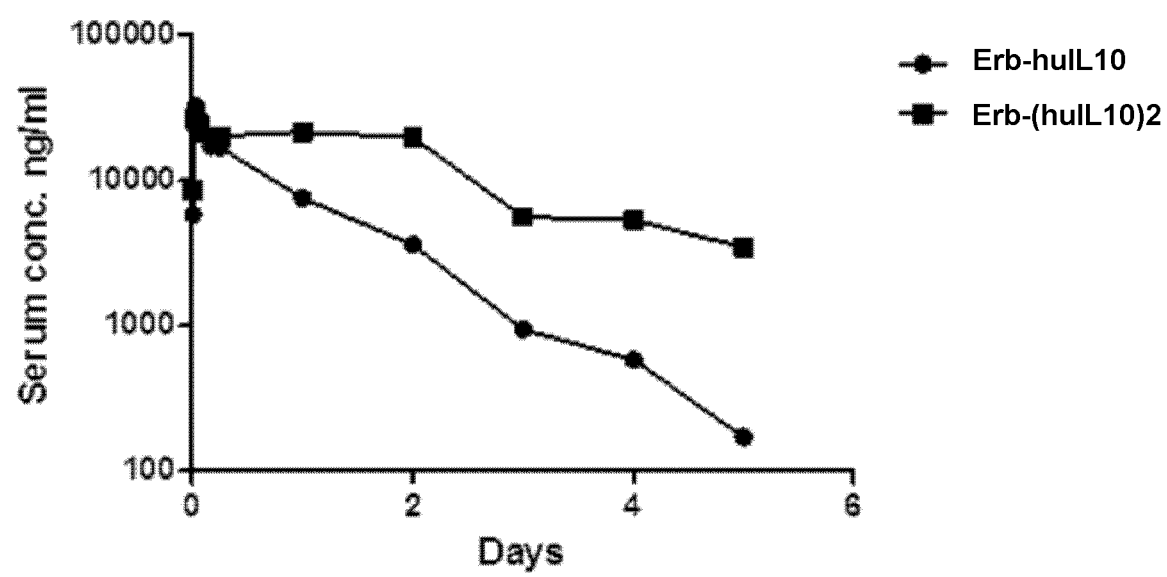
FIG. 11 illustrates results of pharmacokinetic analysis for the heterodimers Erb-huIL10 and Erb-(huIL10)2.

12 C57Bl/6, female, 8-week old mice were divided into 3 groups (group A/B/C), with 4 mice in each group. 20 µg (1 mg/kg) Erb-huIL10 or Erb-(huIL10)2 proteinaceous heterodimers were intraperitoneally injected into the mice (12 mice for each of Erb-huIL10 and Erb-(huIL10)2), 100 µl of blood were taken at 13 different time points after administration of the heterodimers. At each time point, blood was taken from one group of mice, and the three groups rotated. Serum was isolated, then, concentration of Erb-huIL10 or Erb-(huIL10)2 in the serum was determined using ELISA, respectively. Briefly, the ELISA assay was performed as follows: plates were coated with purified anti-human IL-10 (BioLegend, Cat.NO: 501505) at 5 µg/ml then, appropriately diluted serum samples were added. Afterwards, anti-human IgG HRP (Sigma, A0170) was added, and then, TMB development was conducted. WinNolin was used to calculate pharmacokinetic parameters. An average C-T curve obtained, as shown in FIG. 11. The calculated half-life (T1/2) for the heterodimer Erb-huIL10 is 17.63 hours, while for the heterodimer Erb-(huIL10)2 is 33.56 hours.

Figure 28:
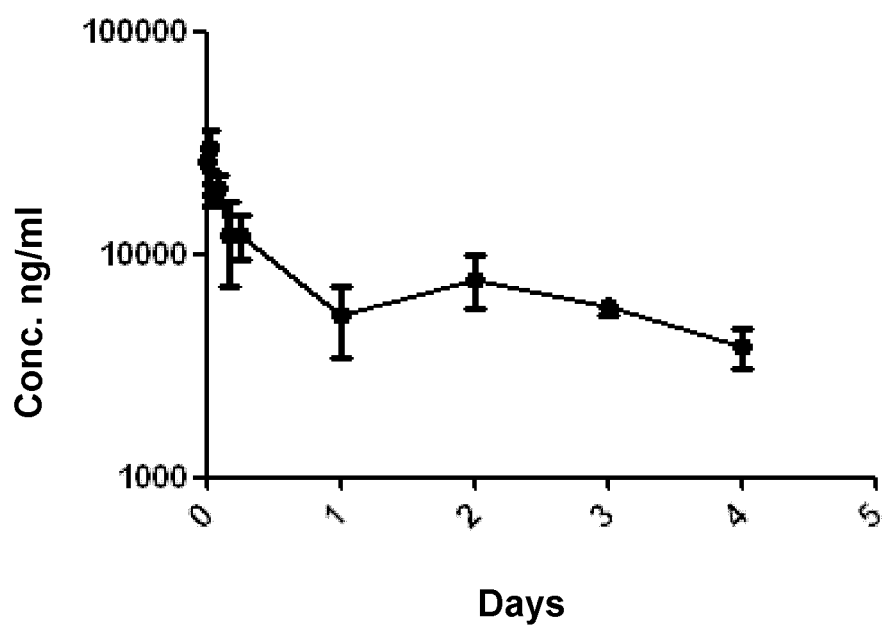
FIG. 28 illustrates results of pharmacokinetic analysis for the heterodimer Erb-(huIL10)2 when injected intravenously.

The pharmacokinetic profile of the heterodimer Erb-(huIL10)2 was further examined by intravenously injecting 20 µg (1 mg/kg) Erb-(huIL10)2 into C57BL/6 mice. The experiments were conducted similarly to those described for intraperitoneal injection. ELISA assay was performed as follows: plates were coated with purified anti-human IL-10 antibody (BioLegend, Cat.NO: 501505) at 5m/ml, then, appropriately diluted serum samples were added. Afterwards, EGFR-biotin and SA-HRP were added, followed with TMB development. WinNolin was used to calculate pharmacokinetic parameters. An average C-T curve obtained is as shown in FIG. 28. The calculated half-life ($T_{1/2}$) for the heterodimer Erb-(huIL10)2 is 49.8 hours.

5.4 Pharmacokinetic of the Heterodimer Erb-huIFNa2

Figure 29:
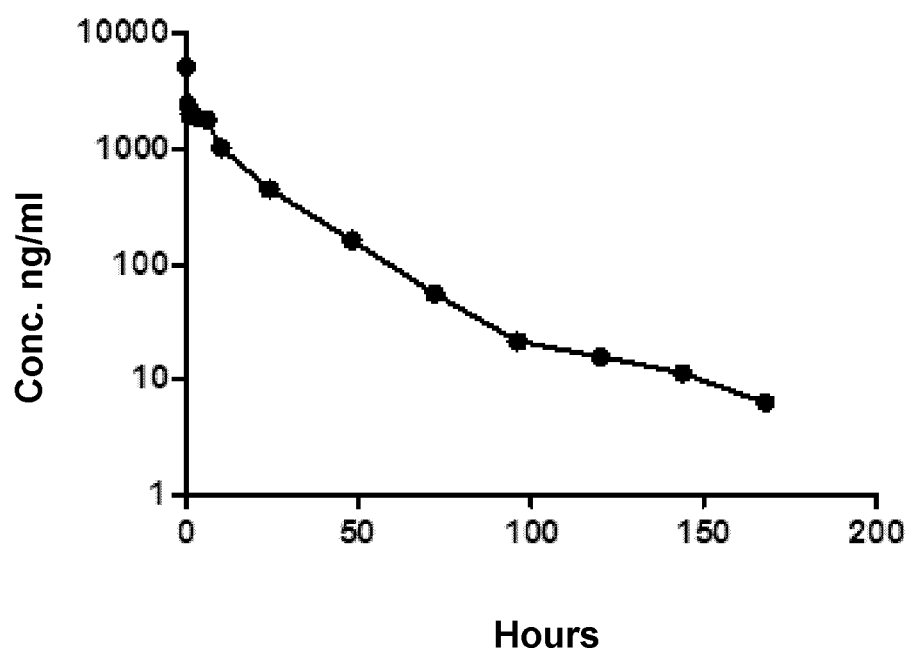
FIG. 29 illustrates results of pharmacokinetic analysis for the heterodimer Erb-huIFNa2 in Cynomolgus monkey.

One male Cynomolgus monkey, was intravenously injected with the proteinaceous heterodimer Erb-huIFNa2 at 0.2 mg/kg. 500 µl of blood were taken at 13 different time points in two weeks after administration of the heterodimer, then, concentration of the heterodimer in the serum was determined using ELISA. Briefly, the ELISA assay was performed as follows: plates were coated with EGFR-Fc protein at 0.8 µg/ml, then, appropriately diluted serum samples were added. Afterwards, anti-human IFNα biotin antibody (eBioscince, BMS-1016BT) was added, and then, streptavidin-HRP (Sigma: 52438) was added for TMB development. WinNolin was used to calculate pharmacokinetic parameters. An average C-T curve obtained is as shown in FIG. 29. The calculated half-life ($T_{1/2}$) for the heterodimer Erb-huIFNa2 is 41.6 hours in Cynomolgus monkey.

5.5 Pharmacokinetic Profile of the Other Proteinaceous Heterodimers of the Present Disclosure Similarly, in vivo half-life (in mouse) of the heterodimer Erb-muIFNb was determined, and the calculated half-life ($T_{1/2}$) for Erb-muIFNb is 34.5 hours (data not shown).

Figure 4:
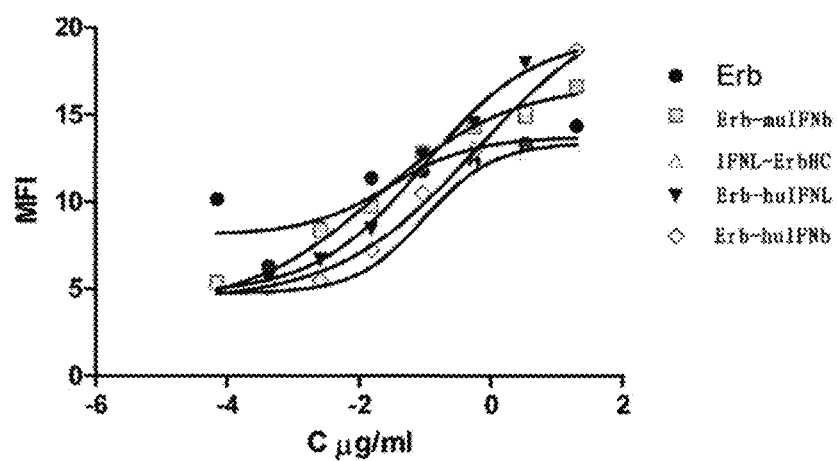
FIG. 4 illustrates specific target binding affinity of the heterodimers Erb-muIFNb, Erb-huIFNb and Erb-huIFNL to EGFR.

Example 6 Binding of the Proteinaceous Heterodimers to Corresponding Targets 6.1 Binding of Erb-Interferon Proteinaceous Heterodimers to EGFR Mouse melanoma cell lines stably expressing human EGFR antigens (B16 cell line, ATCC, CRL6475™) were used to examine binding of the proteinaceous heterodimers to EGFR. Flow cytometry was used, wherein series diluted Erb-interferon proteinaceous heterodimers of the present disclosure (or control Erb antibody Cetuximab (Merck, Erbitux)) and anti-human IgG Fc specific PE (eBioscience: 12-4998-82) secondary antibody were added sequentially into the cells. Then, flow cytometry was performed, and dosage-effect curve was made with protein concentration and medium fluorescence intensity (MFI) from the PE channel. As demonstrated in FIG. 4, various Erb-interferon proteinaceous heterodimers of the present disclosure (e.g., Erb-muIFNb, Erb-huIFNL, and Erb-huIFNb) could specifically bind to EGFR, and the binding affinity was not significantly different from that of the control antibody Cetuximab.

6.2 Binding of Erb-Interleukin Proteinaceous Heterodimers to EGFR

Human squamous cell carcinoma A431 cell line was used to examine binding of the Erb-interleukin proteinaceous heterodimers to EGFR. Flow cytometry analysis was used, wherein series diluted Erb-interleukin proteinaceous heterodimers of the present disclosure (or control Erb antibody (Merck Erbitux)) and anti-human IgG Fc specific PE (eBioscience:12-4998-82) secondary antibody were added sequentially into the cells. Then, flow cytometry analysis was performed, and dosage-effect curve was made with protein concentration and medium fluorescence intensity (MFI) from the PE channel. As demonstrated in panel (A) of FIG. 12, proteinaceous heterodimers Erb-huIL10 and Erb-(huIL10)2 specifically bind to the target EGFR, in a manner similar to the control antibody Cetuximab.

Figure 12:
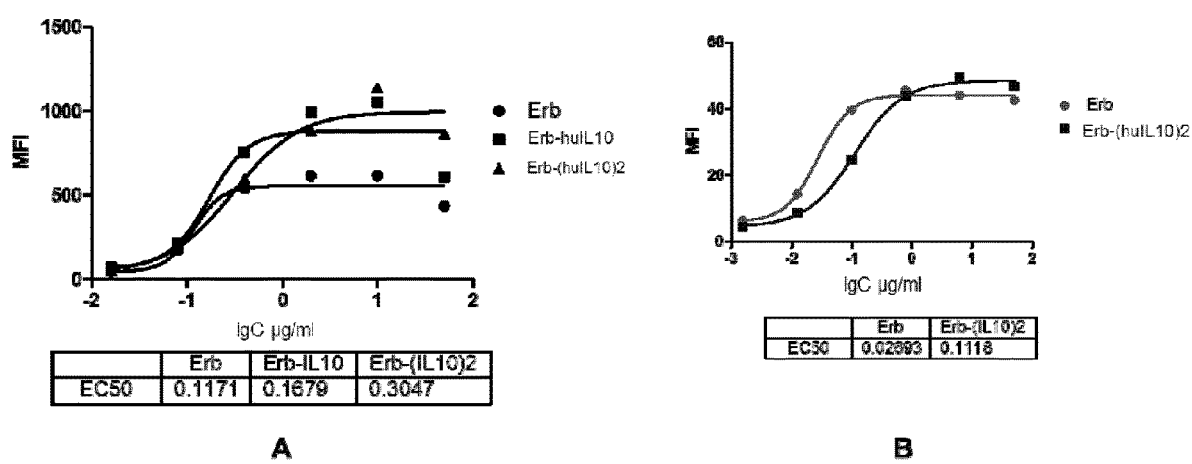
FIG. 12 illustrates specific target binding affinity of the heterodimers Erb-huIL10 and Erb-(huIL10)2 to EGFR using A431 cell line (A) and B16 cell line (B), respectively.

The binding affinity of Erb-(huIL10)2 to its target EGFR was also examined using Mouse melanoma cell lines stably expressing human EGFR (B16 cell line), the result is shown in panel (B) of FIG. 12. It can be seen that Erb-(huIL10)2 specifically bind to the target EGFR, in a manner similar to the control antibody Cetuximab.

Figure 13:
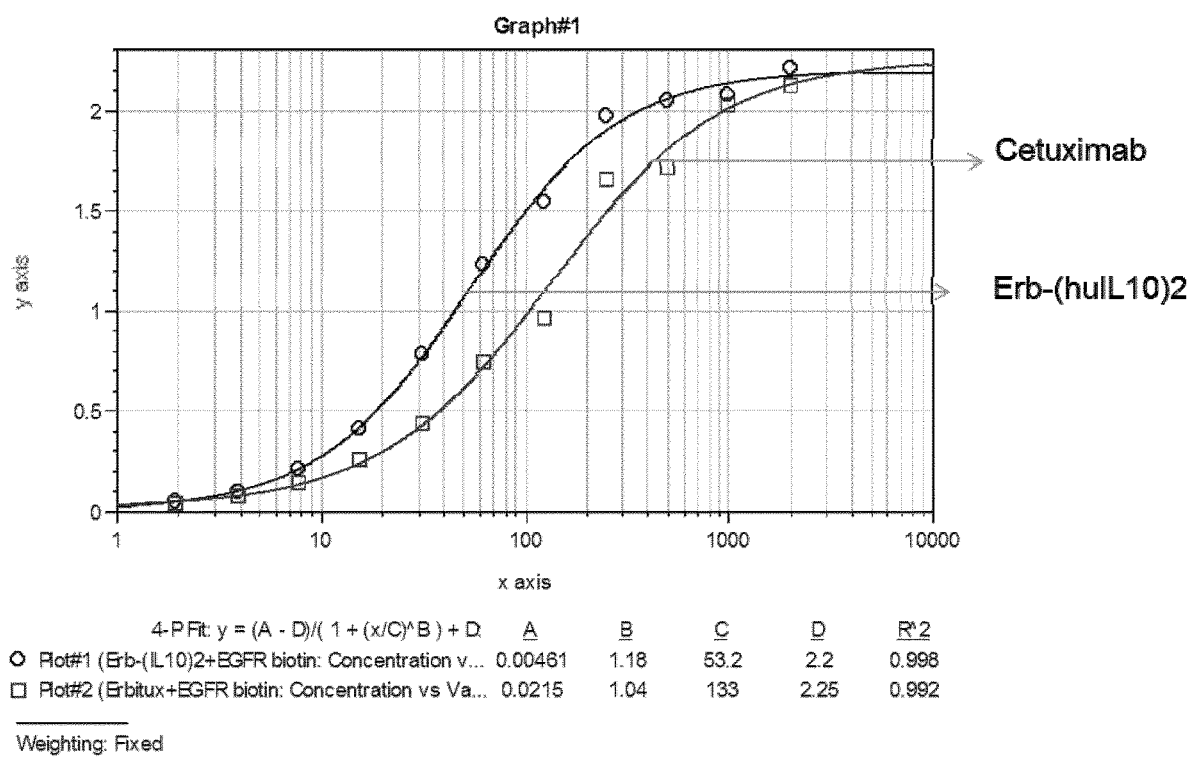
FIG. 13 illustrates specific target binding affinity of the heterodimer Erb-(huIL10)2 to EGFR with ELISA assay.

The specific binding of Erb-(huIL10)2 to EGFR was also confirmed with ELISA, as shown in FIG. 13.

6.3 Binding of Mab806-Interleukin Proteinaceous Heterodimers to EGFR

Figure 14:
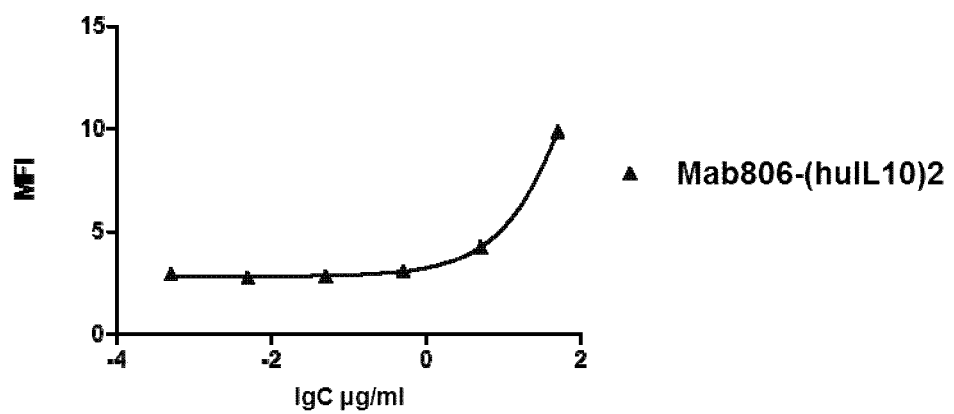
FIG. 14 illustrates specific target binding affinity of the heterodimer Mab806-(huIL10)2 to EGFR.

Similarly, binding affinity of Mab806-(huIL10)2 to EGFR was also examined using Mouse melanoma cell line stably expressing human EGFR (B16 cell line). Mab806 is an antibody targeting the EGFRvIII mutant, however, it may also bind to wild-type EGFR with low affinity. Flow cytometry was performed, and the result is shown in FIG. 14. As can be seen from FIG. 14, Mab806-(huIL10)2 binds to EGFR in a dosage-dependent manner.

6.4 Binding of Tmab-Interferon and Tmab-Interleukin Proteinaceous Heterodimers to her2

Figure 15:
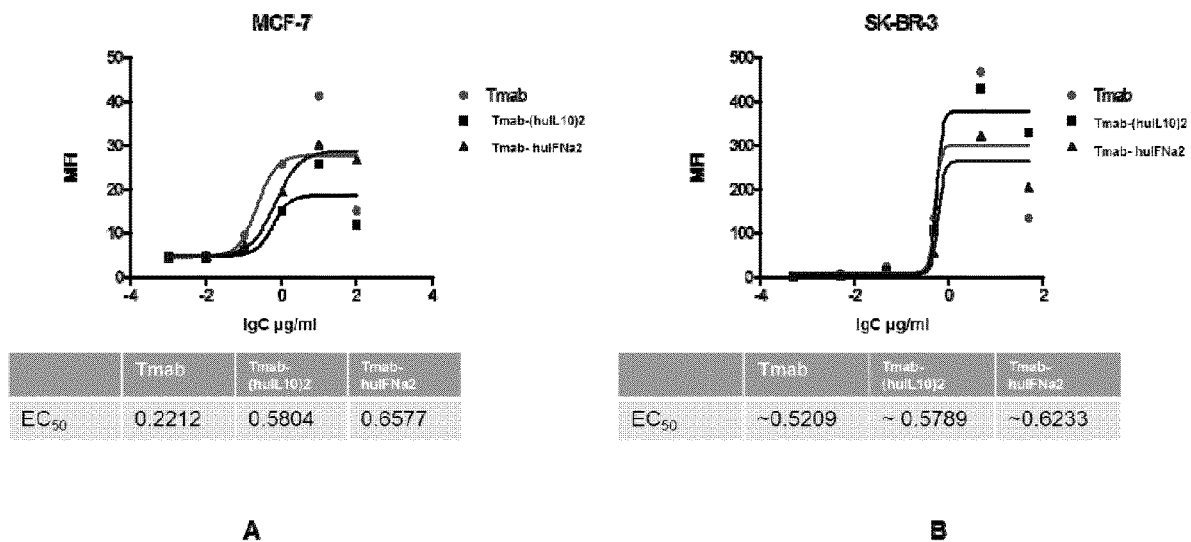
FIG. 15 illustrates specific target binding affinity of the heterodimers Tmab-(huIL10)2 and Tmab-huIFNa2 to HER2, using MCF-7 cell line (A) and SK-BR-3 cell line (B), respectively.

Binding affinity of Tmab-huIFNa2 and Tmab-(huIL10)2 to their target Her2 was also examined, the experiments were conducted using human breast cancer cell-line MCF-7 (ATCC, HTB-22™) and human breast carcinoma cell line SK-BR-3. The results are shown in panel (A) of FIG. 15 (with human breast cancer cell-line MCF-7) and panel (B) of FIG. 15 (with human breast carcinoma cell line SK-BR-3), respectively. As shown in FIG. 15, both Tmab-huIFNa2 and Tmab-(huIL10)2 specifically bind to HER-2, in a way similar to the control antibody Trastuzumab.

6.5 Binding of Pmab-Interleukin Proteinaceous Heterodimers to her2

Figure 16:
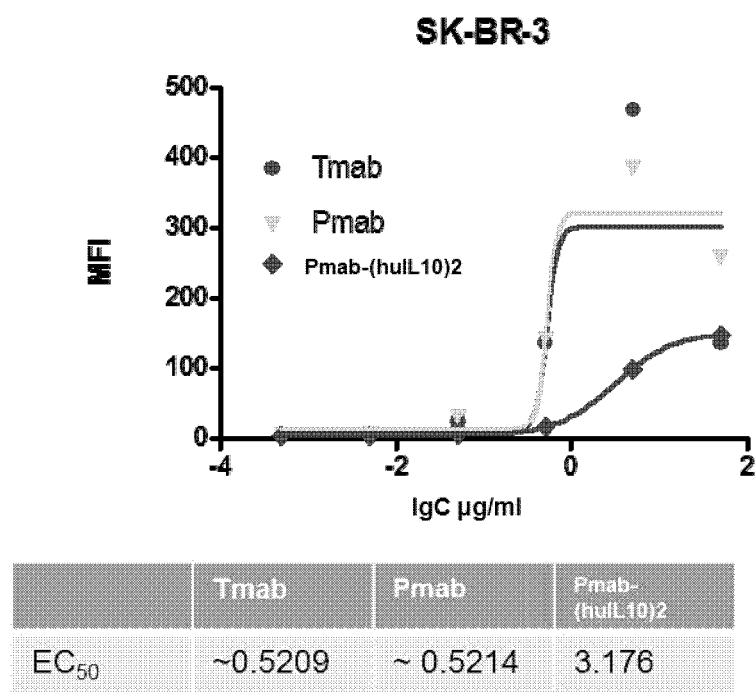
FIG. 16 illustrates specific target binding affinity of the heterodimer Pmab-(huIL10)2 to HER2, using the SK-BR-3 cell line.

Binding affinity of Pmab-(huIL10)2 to its target Her2 was examined using human breast carcinoma cell line SK-BR-3. The results are shown in FIG. 16. As shown in FIG. 16, Pmab-(huIL10)2 specifically bind to HER-2, although its binding affinity is not as good as the control antibodies Trastuzumab and Pertuzumab.

Figure 5:
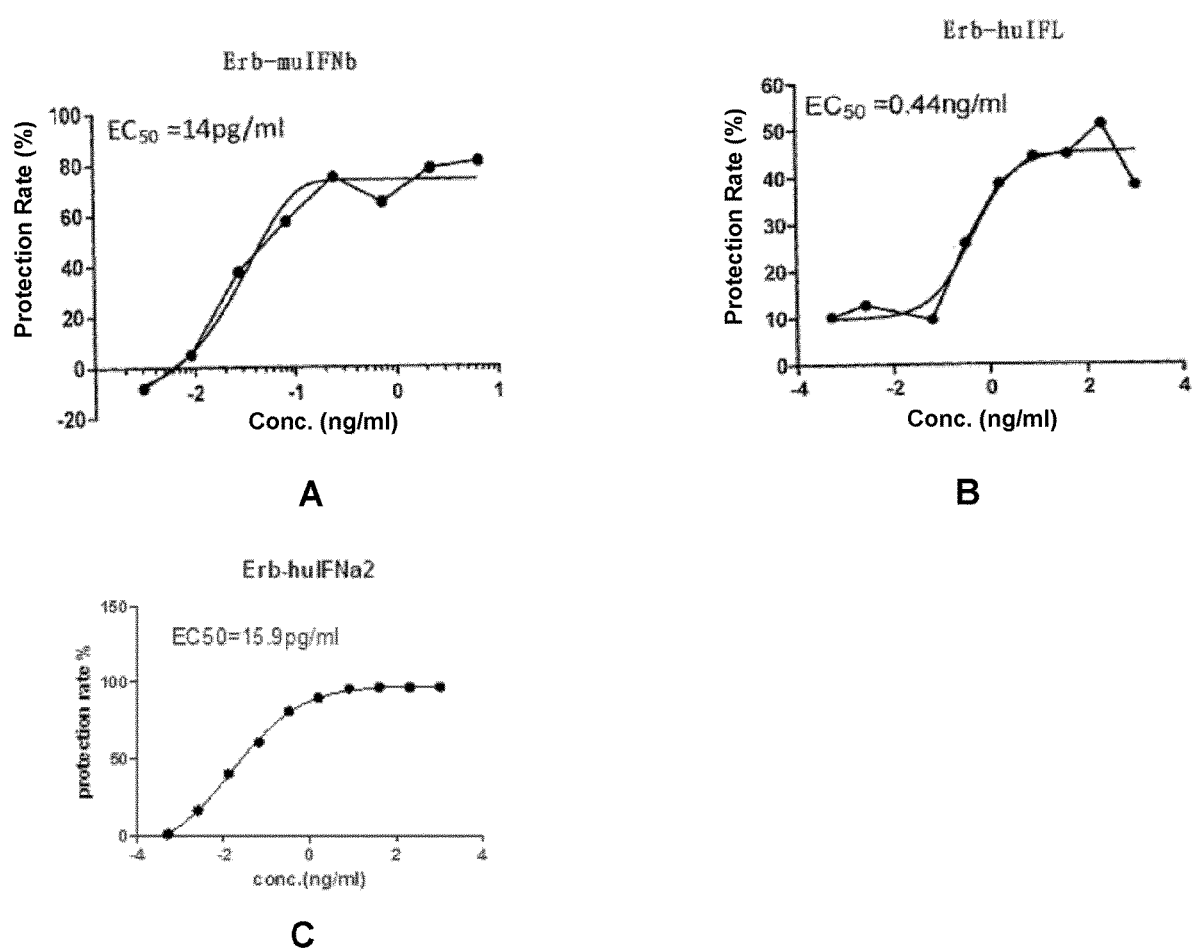
FIG. 5 illustrates anti-virus activities of the heterodimers Erb-muIFNb (A), Erb-huIFNL (B) and Erb-huIFNa2 (C).

Example 7 Biological Activity of the Immunoregulators Comprised in the Proteinaceous Heterodimers 7.1 Biological Activity of Interferons in Erb-Interferon Heterodimers Mouse fibroblast cell line L929 or human hepatoma cell line HepG2 was infected with EGFP (Enhanced Green Fluorescent Protein) labeled Vesicular stomatitis viruses (VSV), to examine the activity of interferons in increasing anti-virus ability of cells. The activity of muIFNb, huIFNa2 and huIFNL was examined, respectively. Briefly, cells were cultured for 8 hours in the presence of series diluted proteinaceous heterodimers of the present disclosure, then, appropriate amount of cells infected with VSV-EGFP was added. 24 hours later, the percentage of infected cells was determined with flow cytometry analysis, and protection rate of the proteinaceous heterodimers for virus infection was calculated. $EC_{50}$ was then obtained according to the dosage-effect curve of protection rate and concentration of the proteinaceous heterodimers. As shown in FIG. 5, the heterodimers Erb-muIFNb, Erb-huIFNa2 and Erb-huIFNL protected the cells from virus infection.

7.2 Biological Activity of Interleukins in Erb-Interleukin Heterodimers

Figure 17:
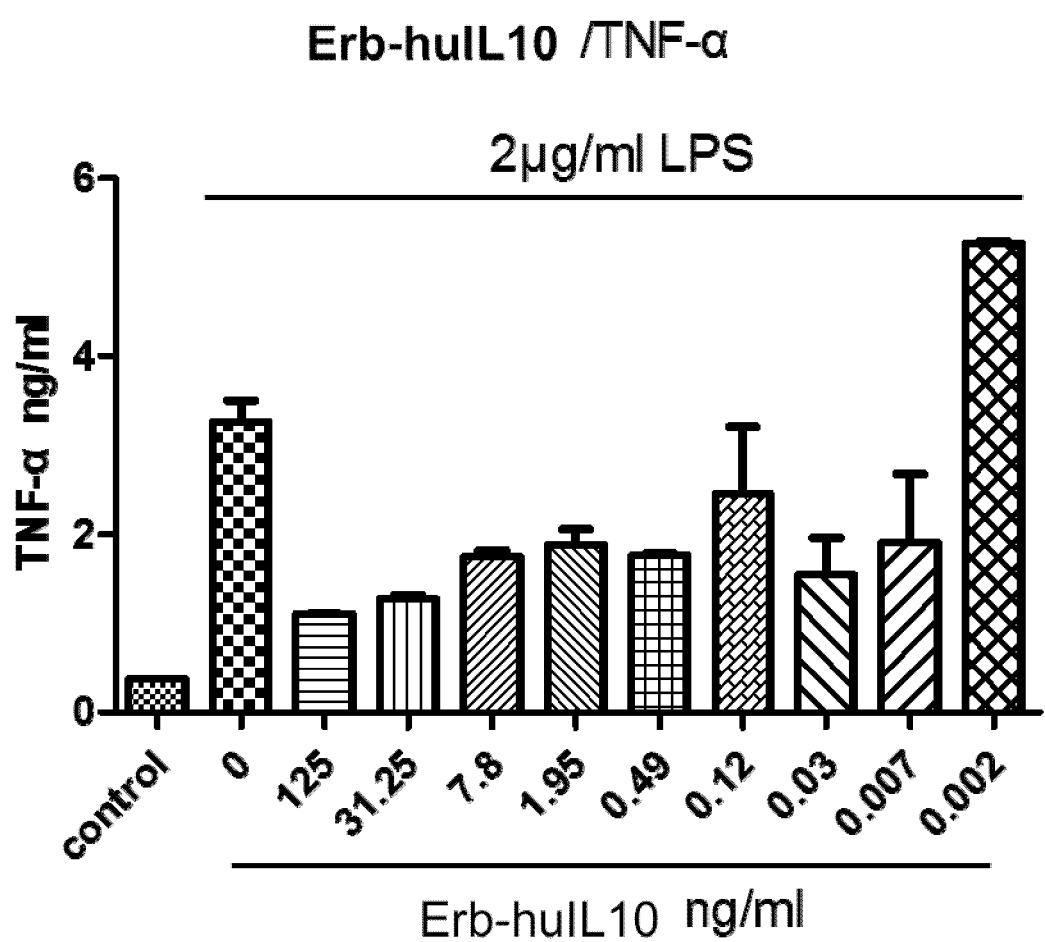
FIG. 17 illustrates the activity of Erb-huIL10 in inhibiting lipopolysaccharide (LPS) stimulated release of TNF-α by human peripheral blood mononuclear cells (PBMC).
Figure 18:
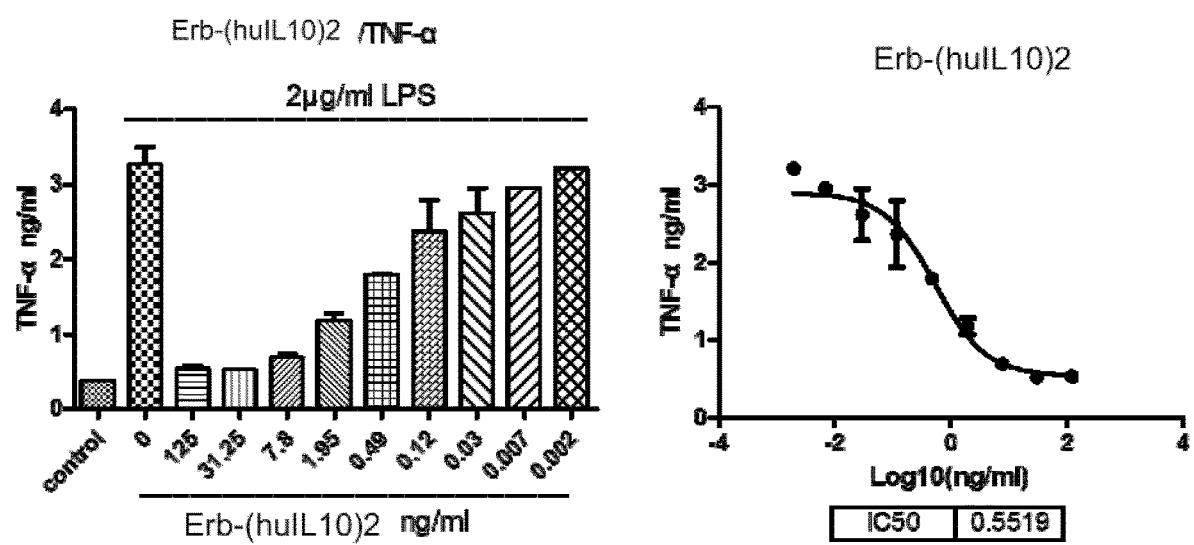
FIG. 18 illustrates the activity of Erb-(huIL10)2 in inhibiting lipopolysaccharide (LPS) stimulated release of TNF-α by human peripheral blood mononuclear cells (PBMC).

Interleukins can inhibit lipopolysaccharide (LPS) stimulated release of TNF-α from macrophages (David F. et al., 1991, The Journal of Immunology. Vol. 147.3815-3822). To test this activity of interleukins in the proteinaceous heterodimers of the present disclosure, human peripheral blood mononuclear cells (PBMC) were seeded in a 96-well plate, suspended cells were washed away after 3-4 hours. Then, various concentrations of Erb-huIL10 or Erb-(huIL10)2 of the present disclosure were added, and 2 hrs later, 2 μg/ml LPS was added for stimulation of 24 hours. Supernatant was collected, and release of TNF-α was examined using ELISA. The ELISA was conducted according to the instructions included in the TNF-α Kit (eBioscience, 88-7346). Briefly, capture antibody was diluted with coating buffer, then, Costar 9018 ELISA plate was coated; then, a standard and appropriately diluted samples were added. Afterwards, reaction was detected using detection antibody, and developed with TMB. The results are shown in FIG. 17 and FIG. 18. As demonstrated in FIG. 17, Erb-huIL10 inhibits release of TNF-α in a dosage dependent manner. FIG. 18 shows that Erb-(huIL10)2 of the present disclosure also effectively inhibits release of TNF-α in a dosage dependent manner, and the dosage dependent inhibition is even more evident comparing to that of Erb-huIL10.

7.3 Biological Activity of Immunoregulators in Other Proteinaceous Heterodimers

Figure 19:
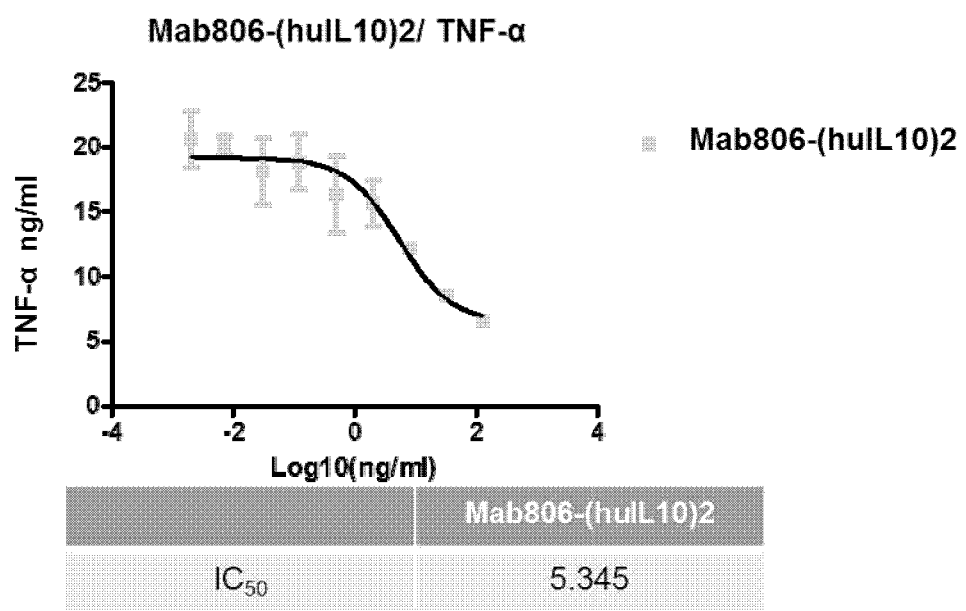
FIG. 19 illustrates the activity of Mab806-(huIL10)2 in inhibiting lipopolysaccharide (LPS) stimulated release of TNF-α by human peripheral blood mononuclear cells (PBMC).
Figure 20:
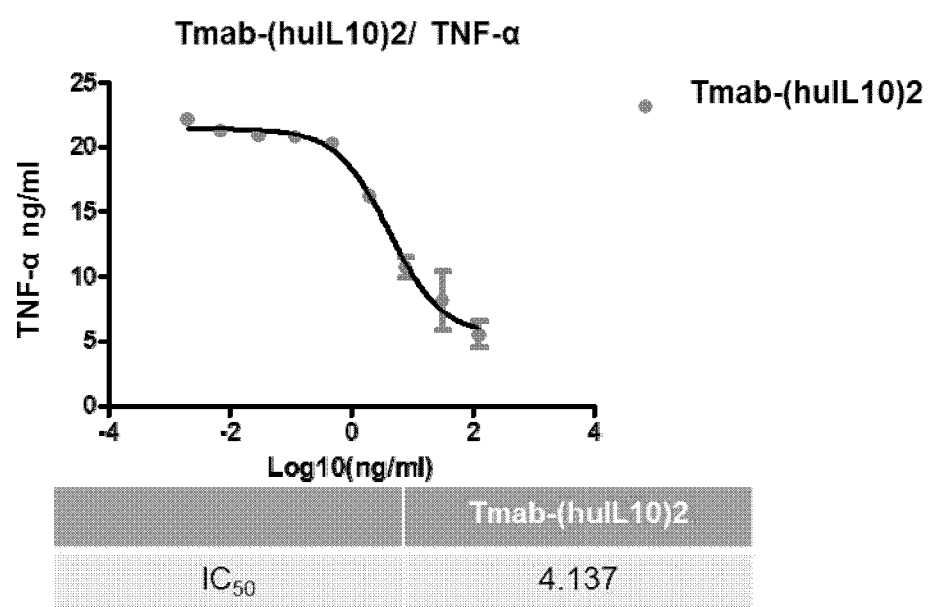
FIG. 20 illustrates the activity of Tmab-(huIL10)2 in inhibiting lipopolysaccharide (LPS) stimulated release of TNF-α by human peripheral blood mononuclear cells (PBMC).
Figure 21:
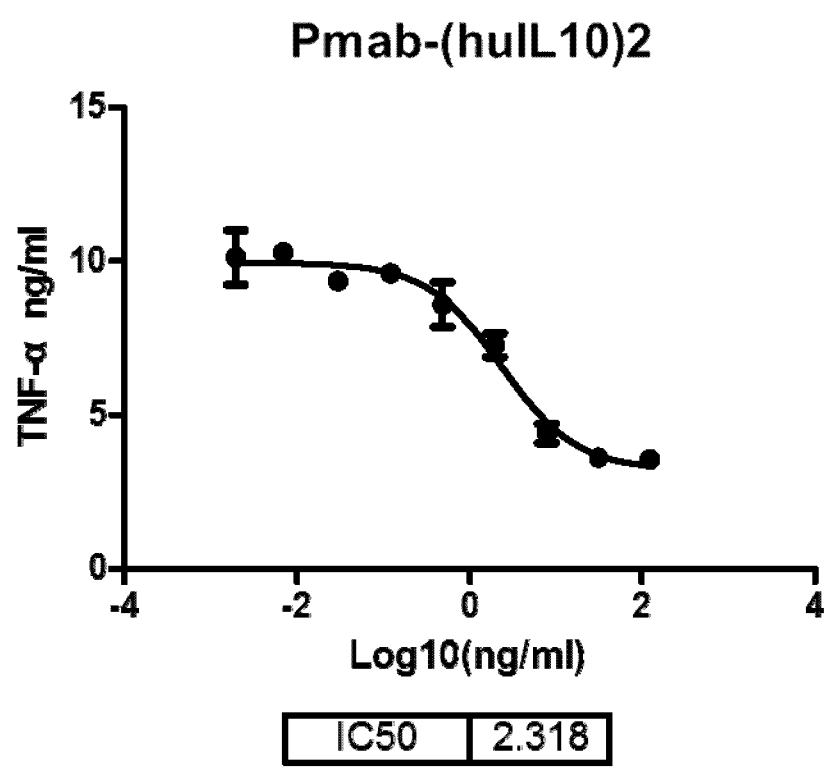
FIG. 21 illustrates the activity of Pmab-(huIL10)2 in inhibiting lipopolysaccharide (LPS) stimulated release of TNF-α by human peripheral blood mononuclear cells (PBMC).

Similarly, biological activities of the immunoregulators in other proteinaceous heterodimers of the present disclosure were also examined. FIG. 19 shows that Mab806-(huIL10)2 of the present disclosure effectively inhibits release of TNF-α in a dosage dependent manner. FIG. 20 shows the dosage dependent inhibition of TNF-α release by Tmab-(huIL10)2 of the present disclosure. FIG. 21 shows that Pmab-(huIL10)2 of the present disclosure effectively inhibits release of TNF-α in a dosage dependent manner.

Example 8 In Vitro Anti-Tumor Activity of the Proteinaceous Heterodimers

Figure 8:
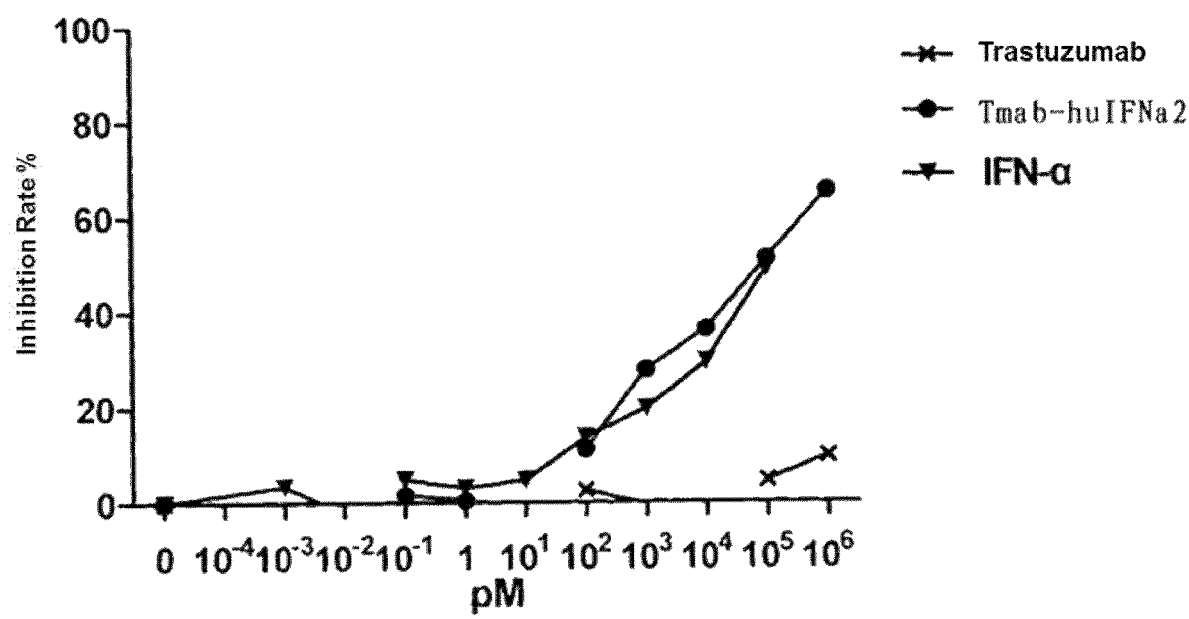
FIG. 8 illustrates the in vitro anti-tumor activity of the heterodimer Tmab-huIFNa2 on MCF-7 cell line.

Human breast cancer cell-line MCF-7 (ATCC, HTB-22™) expressing low level of Her2 antigen was used to evaluate in vitro anti-tumor effect of Tmab-huIFNa2 heterodimers. Briefly, cells were cultured in the presence of series diluted antibody Trastuzumab, interferon α, or Tmab-huIFNa2 heterodimers for 72 hours, cell proliferation was then examined using the CCK8 (Cell Counting Kit 8) assay. Cell proliferation inhibition rate was calculated and dosage-effect curve was obtained. Apoptosis was examined with 7AAD staining and flow cytometry assay. It can be seen from FIG. 8 that Trastuzumab alone did not inhibit tumor cell proliferation, while the proteinaceous heterodimers of the present disclosure significantly inhibited MCF7 cell growth in a dosage dependent manner. The inhibition effect of the proteinaceous heterodimers is comparable to that of the interferons. Apoptosis results are not significantly different among various groups (data not shown), suggesting that the proteinaceous heterodimers of the present disclosure could effectively inhibit tumor cell growth, while not affecting cell apoptosis.

Figure 9:
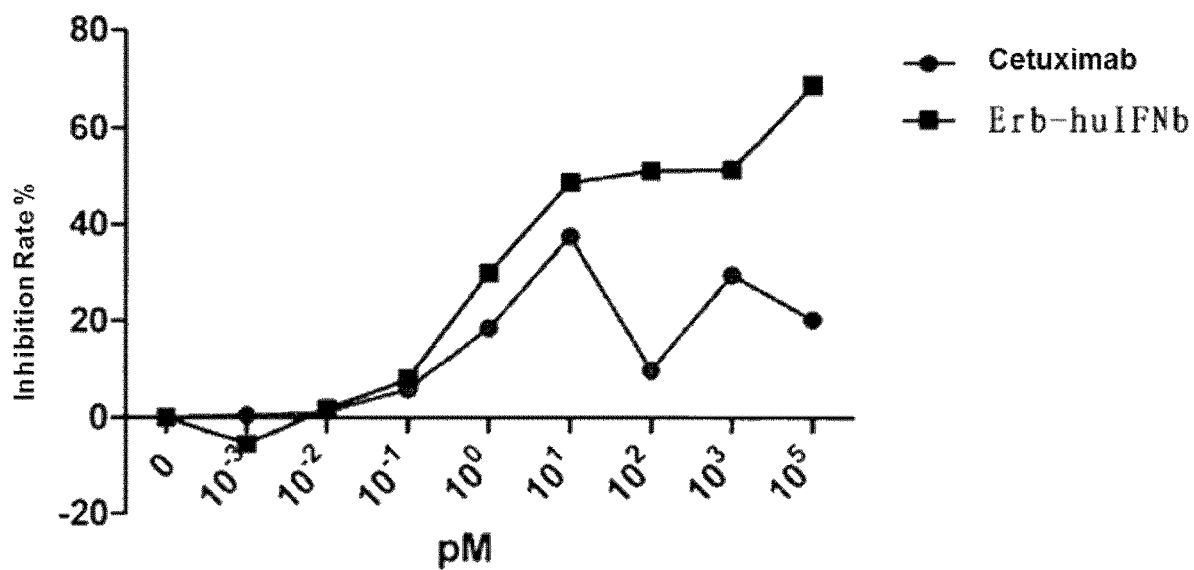
FIG. 9 illustrates the in vitro anti-tumor activity of the heterodimer Erb-huIFNb on A431 cell line.

Similarly, tumor cell line A431 expressing EGFR was used to evaluate the anti-tumor activity of Erb-huIFNb heterodimers. Briefly, the cells were cultured in the presence of series diluted antibody Cetuximab, or Erb-huIFNb heterodimers for 72 hours, cell proliferation was examined using the MTT colorimetric method. Cell proliferation inhibition rate was calculated and dosage-effect curve was obtained. As can be seen from FIG. 9, the anti-tumor effect of the proteinaceous heterodimers of the present disclosure is significantly stronger than that of Cetuximab, and the inhibition is dosage dependent.

Figure 6:
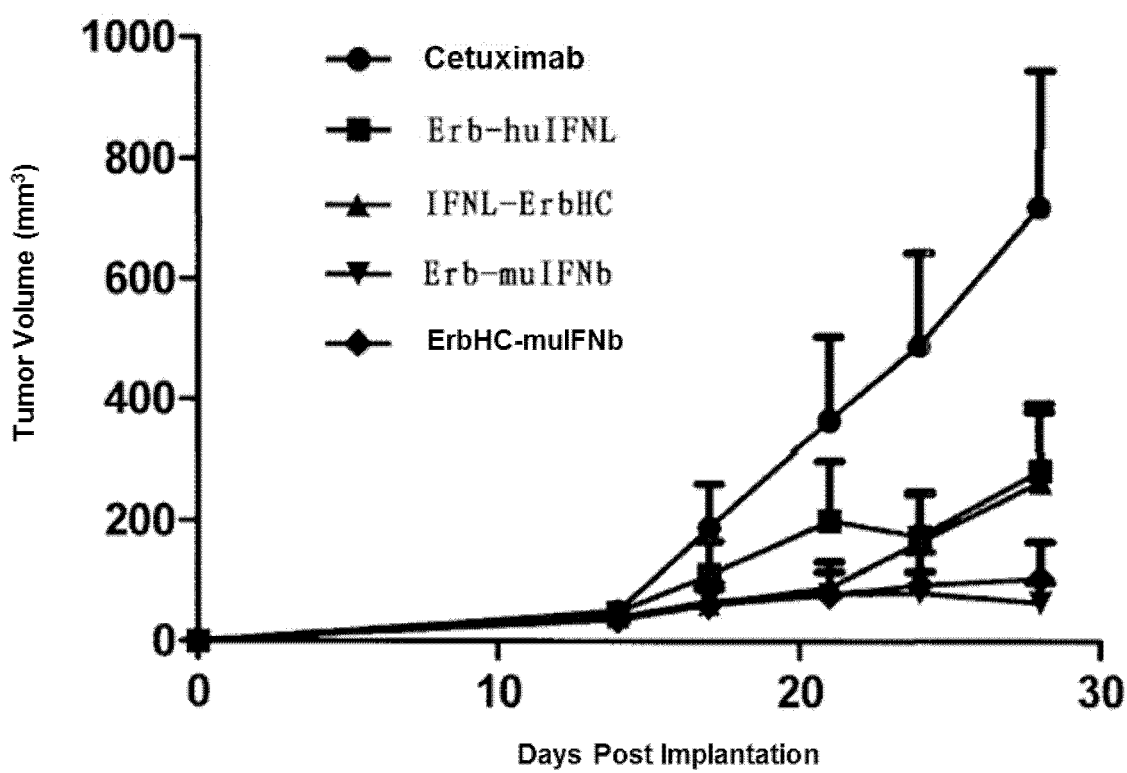
FIG. 6 illustrates the in vivo anti-tumor activity of the heterodimers Erb-muIFNb and Erb-huIFNL.

Example 9 In Vivo Anti-Tumor Activity of the Proteinaceous Heterodimers 9.1 In Vivo Anti-Tumor Activity of Erb-Interferon Heterodimers of the Present Disclosure B16-EGFR mouse model was used to examine the activity of the proteinaceous heterodimers of the present disclosure. Briefly, 8-week old female C57 BL/6 mice were subcutaneously injected with $7 \times 10^5$ B16-EGFR-SIY cells. After 14 days, the tumor volume was measured to be around 70 mm$^3$. Erb-muIFNb heterodimer, C-terminal fusion protein ErbHC-muIFNb, Erb-huIFNL heterodimer, or N-terminal fusion protein IFNL-ErbHC was administrated in situ at the site of the tumors, respectively (25 µg/time, once every two days, 3 times in total). Tumor size was measured every three days, the volume of the tumors was calculated to obtain a curve of tumor growth. The results are shown in FIG. 6. As can be seen in FIG. 6, in vivo anti-tumor activity of the proteinaceous heterodimers of the present disclosure is comparable to that of the corresponding fusion proteins.

Figure 7:
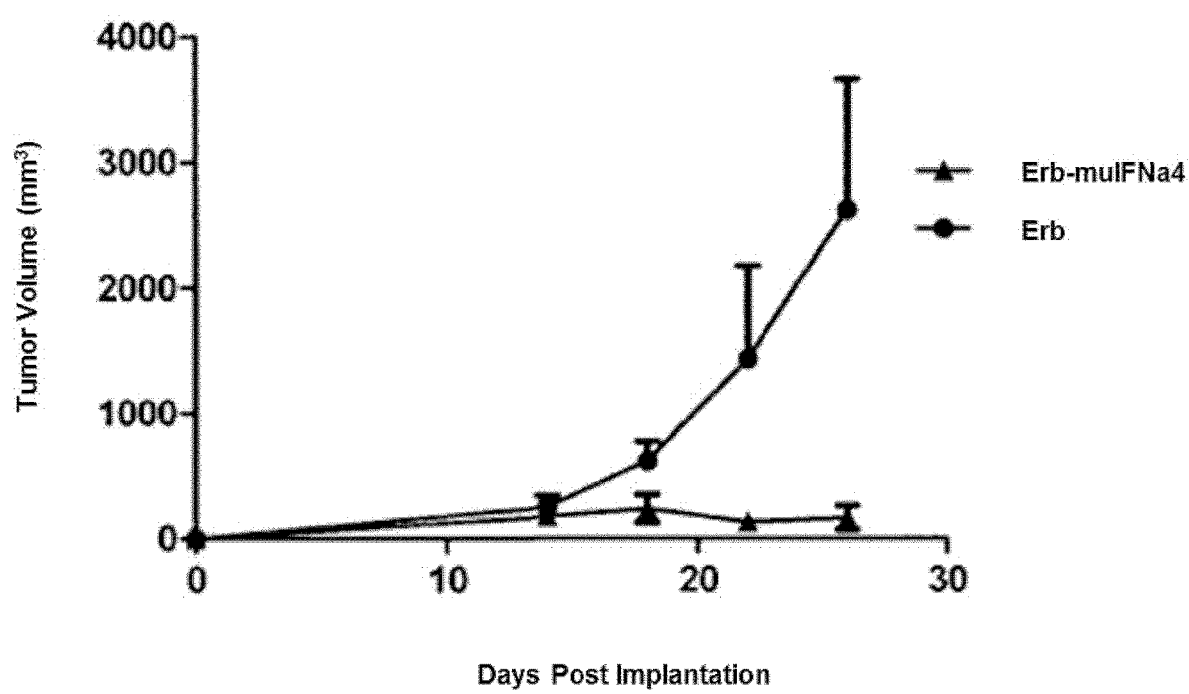
FIG. 7 illustrates the in vivo anti-tumor activity of the heterodimer Erb-muIFNa4.

In human, EGFR is not only highly expressed at the site of tumors, it is also expressed at a low baseline level in normal tissues. To obtain an animal model that more closely mimics the conditions in human beings, EGFR transgenic mice inoculated with B16-EGFR tumor cells were also used as a model system to evaluate the effect of the heterodimers of the present disclosure. Briefly, 8-week old female EGFR transgenic C57 BL/6 mice were subcutaneously injected with $5 \times 10^5$ B16-EGFR-SIY cells. After 14 days, the tumor volume was measured to be around 70 mm$^3$. Erb-muIFNa4 heterodimers or control Cetuximab antibody was administered intravenously (200 µg/time, once every three days, 2 times in total). Tumor size was measured every three days, the volume of the tumors was calculated to obtain a curve of tumor growth. The results are shown in FIG. 7. As can be seen in FIG. 7, in vivo anti-tumor activity of the proteinaceous heterodimers of the present disclosure is very remarkable. In addition, in this experiment, the proteinaceous heterodimers of the present disclosure was administered systematically instead of at the site of the tumor, accordingly, the excellent anti-tumor effects observed indicate that the proteinaceous heterodimers effectively target the tumor cells in vivo.

Figure 22:
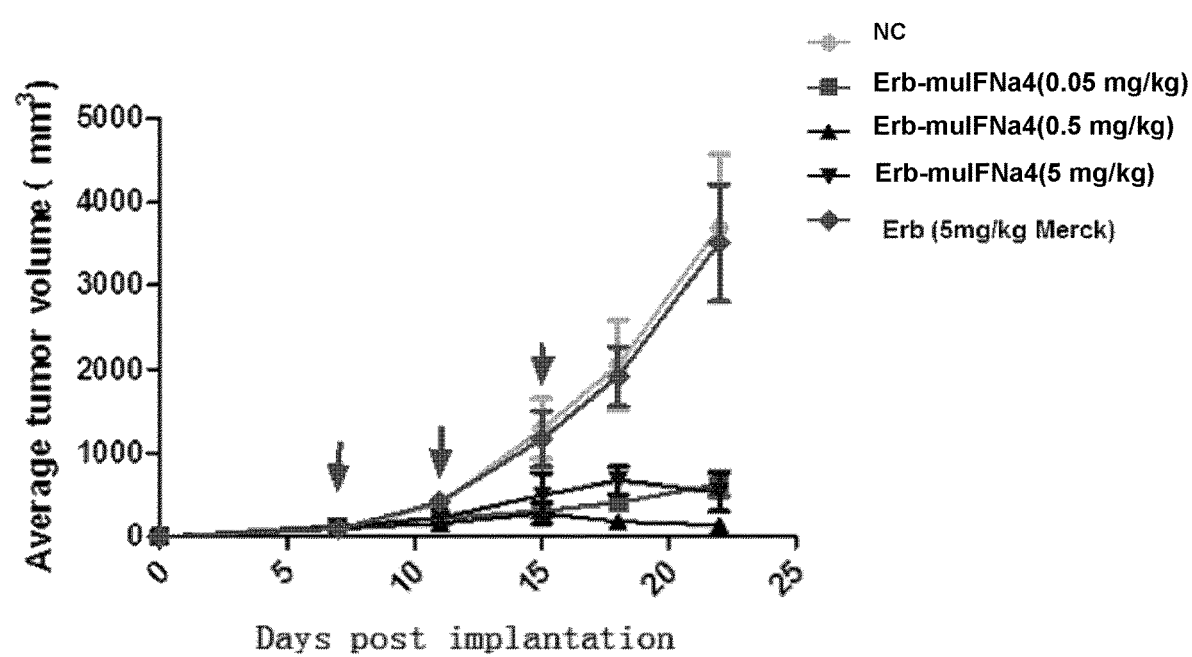
FIG. 22 illustrates inhibition of tumor growth in vivo after intraperitoneal injection of different concentrations of Erb-muIFNa4.

The in vivo anti-tumor activity of Erb-muIFNa4 heterodimer was also tested using C57 BL/6 wide type mouse model. Briefly, 8-week old female C57 BL/6 mice were subcutaneously injected with $7 \times 10^5$ B16-EGFR-SIY cells. After 7 days, the tumor volume was measured to be around 45 mm$^3$. Erb-muIFNa4 heterodimer or control antibody Cetuximab (Erbitux, Merck) was injected intra-peritoneally (i.p.). Erb-muIFNa4 heterodimer was injected at three different doses (5 mg/kg, 0.5 mg/kg and 0.05 mg/kg, respectively), and the dosage of Cetuximab was 5 mg/kg, both were administered twice per week, totally 3 doses. Tumor size was measured twice per week, and the volume of the tumors was calculated to obtain a curve of tumor growth. The results are demonstrated in FIG. 22, for each dosage administered, the Erb-muIFNa4 heterodimer effectively reduced tumor volume in vivo.

Figure 23:
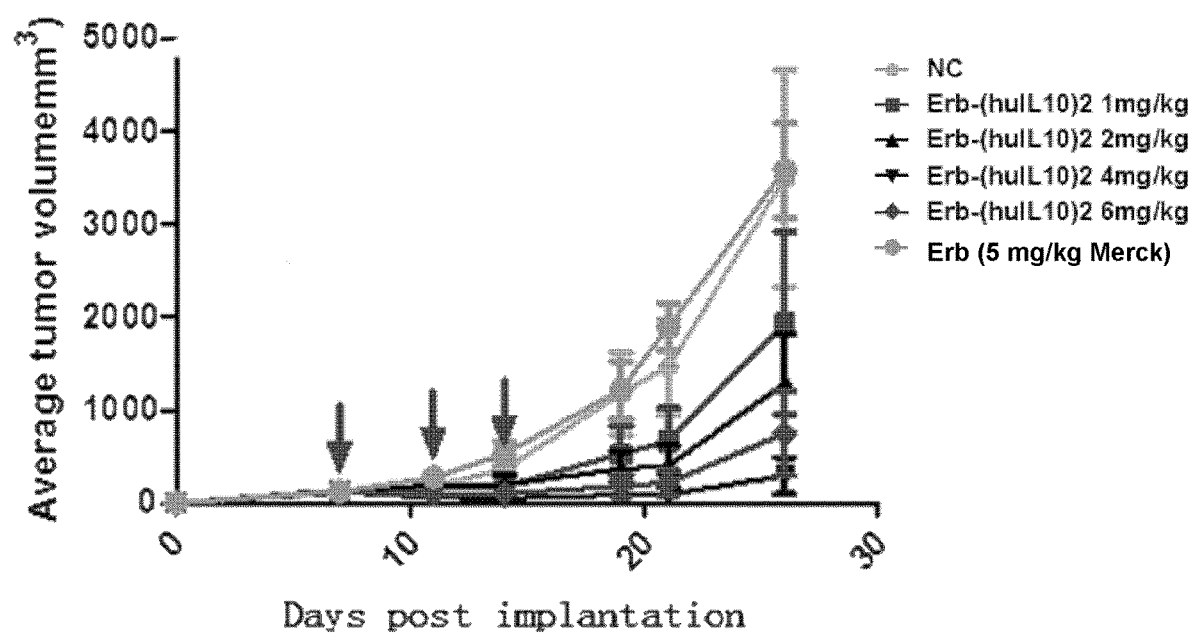
FIG. 23 illustrates inhibition of tumor growth in vivo after intraperitoneal injection of different concentrations of Erb-(huIL10)2.

9.2 In Vivo Anti-Tumor Activity of Erb-Interleukin Heterodimers of the Present Disclosure Similar to Example 9.1, in vivo anti-tumor activity of Erb-(huIL10)2 was tested using C57 BL/6 mouse model. Briefly, 8-week old female C57 BL/6 mice were subcutaneously injected with $7 \times 10^5$ B16-EGFR-SIY cells. After 7 days, the tumor volume was measured to be around 45 mm$^3$. Erb-(huIL10)2 heterodimer or control antibody Cetuximab (Erbitux, Merck) was injected intra-peritoneally (i.p.). Erb-(huIL10)2 heterodimer was injected at four different doses (1 mg/kg, 2 mg/kg, 4 mg/kg and 6 mg/kg, respectively), and the dosage of Cetuximab was 5 mg/kg, both were administered twice per week, 3 doses in total. Tumor size was measured twice per week, the volume of the tumors was calculated to obtain a curve of tumor growth. The results are demonstrated in FIG. 23. Erb-(huIL10)2 effectively reduced tumor volume in vivo in a dosage dependent manner. In addition, in this experiment, the proteinaceous heterodimers of the present disclosure was administered systematically instead of at the site of the tumor, accordingly, the excellent anti-tumor effects observed indicate that the proteinaceous heterodimers effectively target the tumor cells in vivo.

Figure 24:
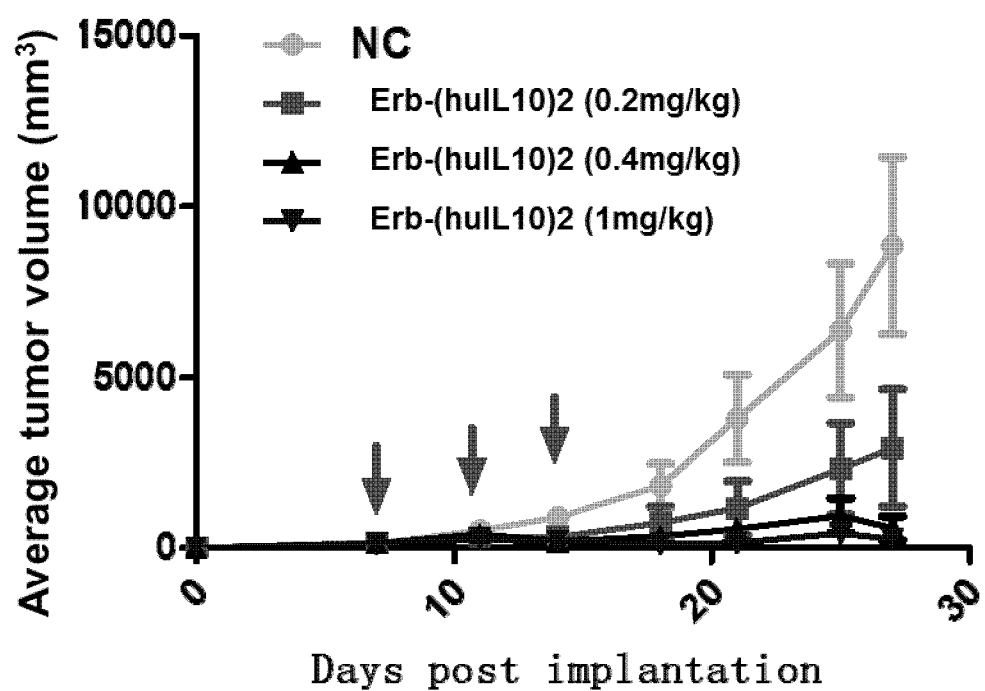
FIG. 24 illustrates dosage dependent inhibition of tumor growth in vivo after intratumor injection of different concentrations of Erb-(huIL10)2.

The in vivo anti-tumor effect of Erb-(huIL10)2 was also examined by injecting the heterodimer Erb-(huIL10)2 in situ at the site of tumors. The mouse tumor models were prepared as described in Example 9.2. Erb-(huIL10)2 heterodimer was injected at three different doses (0.2 mg/kg, 0.4 mg/kg, and 1 mg/kg, respectively) from day 7 after tumor inoculation, administered every 3 days and three doses were administered in total. Phosphate buffer saline (PBS) was used as a negative control. The results are demonstrated in FIG. 24. As can be seen from FIG. 24, Erb-(huIL10)2 effectively reduced tumor volume in vivo in a dosage dependent manner when injected at the site of tumors.

Figure 25:
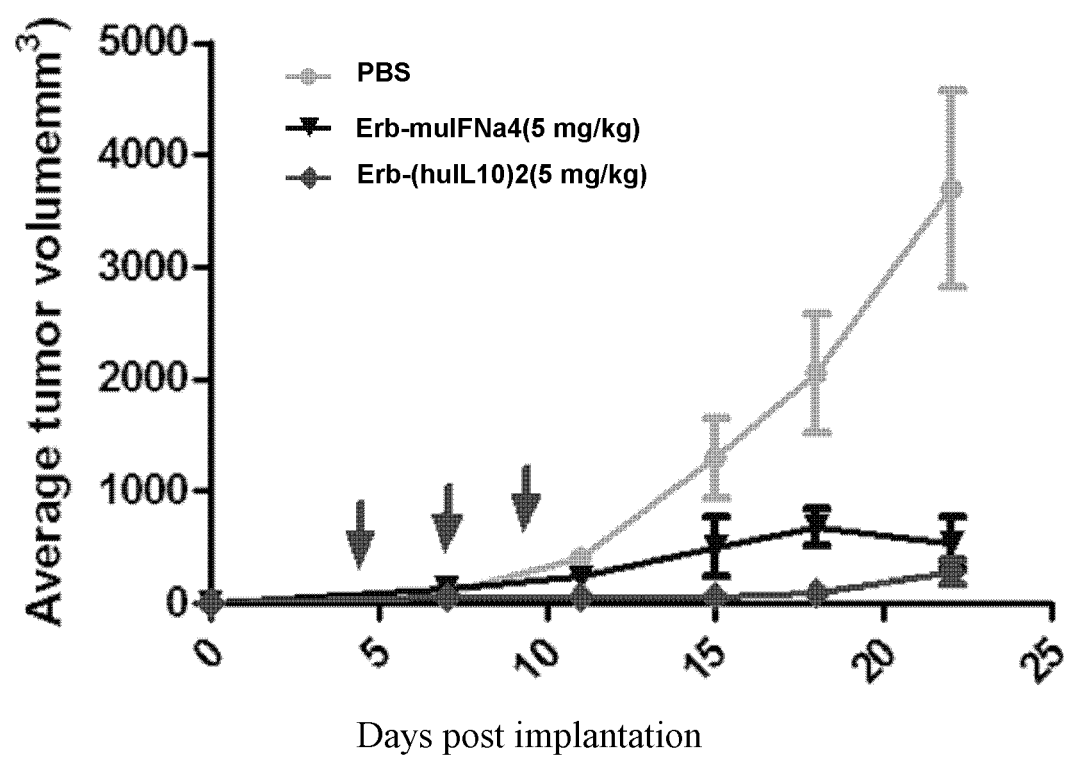
FIG. 25 illustrates comparison of inhibition of tumor growth in vivo by intraperitoneal injection of Erb-muIFNa4 and Erb-(huIL10)2.

A comparison of the in vivo anti-tumor effect between Erb-(huIL10)2 and Erb-muIFNa4 is shown in FIG. 25. The mouse tumor models were prepared as described in Example 9.2. Erb-(huIL10)2 and Erb-muIFNa4 were injected intra-peritoneally (i.p.) at a dosage of 5 mg/kg, respectively. They were injected from day 7 after tumor inoculation, administered every 3 days, and three doses were administered in total. PBS was used as a negative control. As can be seen from FIG. 25, both Erb-(huIL10)2 and Erb-muIFNa4 effectively inhibited increase of tumor size, with the effect of Erb-(huIL10)2 appearing more prominent.

Figure 26:
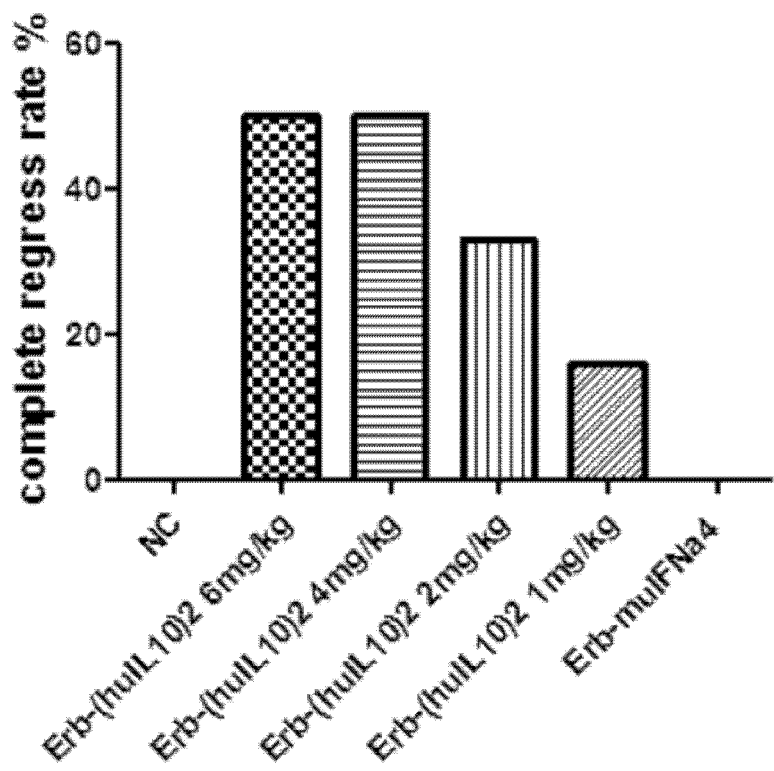
FIG. 26 illustrates comparison of tumor regression in vivo by different doses of Erb-muIFNa4 and Erb-(huIL10)2.

In the study, it was found that although both Erb-(huIL10)2 and Erb-muIFNa4 effectively inhibited increase of tumor size, only Erb-(huIL10)2 results in complete tumor regression in part of the mice treated and the percentage of tumor regression mice increased dose dependently. An analysis of tumor regression rate was shown in FIG. 26. Erb-muIFNa4 inhibited tumor growth in mice, but no complete tumor regression was observed, while Erb-(huIL10)2 administration resulted in complete tumor regression in as high as 50% of the mice tested.

Figure 27:
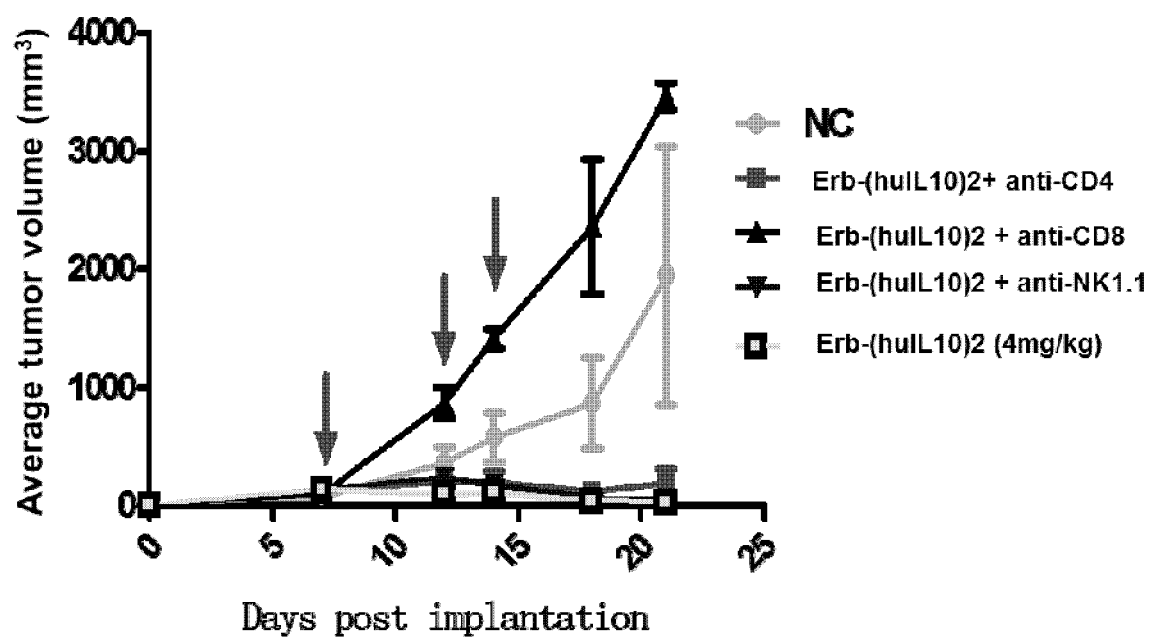
FIG. 27 illustrates effect of anti-CD4, anti-CD8 and anti-NK1.1 on the inhibition of tumor growth in vivo by Erb-(huIL10)2.

Mechanisms leading to the anti-tumor activity of Erb-(huIL10)2 were further investigated. Mouse tumor models were prepared as described in 9.2. The heterodimer Erb-(huIL10)2 was injected intra-peritoneally (i.p.) at 4 mg/kg since day 7 after tumor inoculation, it was administered every 3 days and three doses were administered in total. PBS was used as a negative control. 200 µg of CD8, CD4, and NK cell depleting antibodies were administered at day 5 in the groups indicated, the depleting antibodies were administered repeatedly every 3 days, and 5 doses were administered in total for each of the depleting antibodies. As can be seen from FIG. 27, the anti-tumor effect of Erb-(huIL10)2 was depleted with anti-CD8 antibody, while depletion of CD4 or NK1.1 did not significantly affect the anti-tumor activity of Erb-(huIL10)2, suggesting that the anti-tumor activity of Erb-(huIL10)2 is likely to be CD8+ T cell dependent.

Example 10 Targeting Behavior of the Proteinaceous Heterodimers In Vivo

Figure 30:
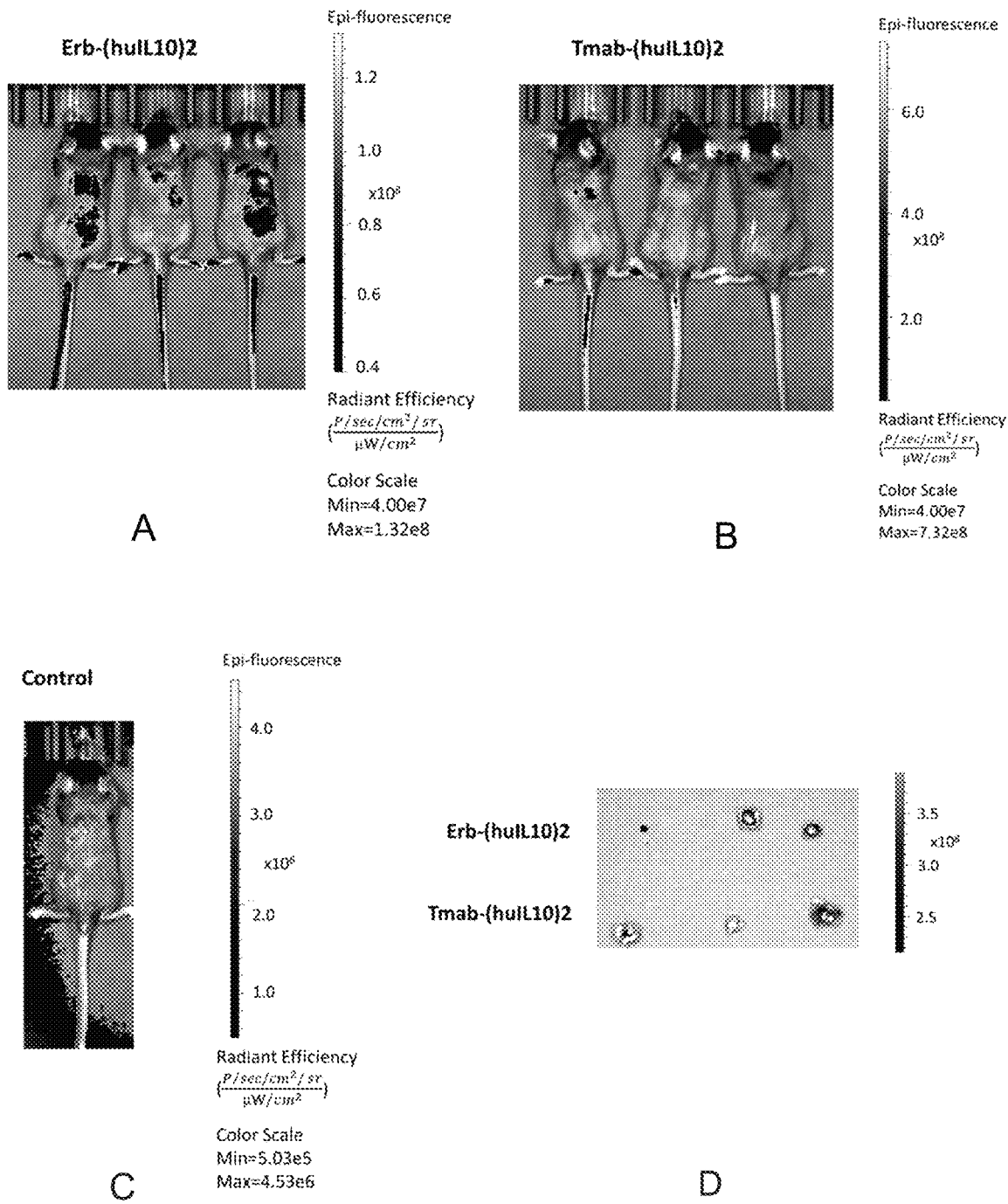
FIG. 30 illustrates the in vivo distribution of Erb-(huIL10)2 in mice.

Similar to the procedures shown in Example 9.1, in vivo distribution of Erb-(huIL10)2 was examined using C57BL/6 B16-EGFR mouse model. Briefly, 8-week old female C57 BL/6 mice were subcutaneously injected with $7 \times 10^5$ B16-EGFR-SIY cells. After 7 days, tumor volume was measured to be around 45 mm$^3$. Alexa Fluor 750 (AF750) labelled Erb-(huIL10)2 heterodimer or control heterodimer Tmab-(huIL10)2 was injected intra-peritoneally (i.p). 24 hrs after injection, the AF750 immunofluorescence signal was screened for in vivo with IVIS spectrum in vivo imaging system (Perkin Elmer) or in vitro after removing the tumors. The results (as shown in FIG. 30) demonstrated that the concentration of Erb-(huIL10)2 is much higher than that of Tmab-(huIL10)2 in EGFR positive tumors. Thus, proteinaceous heterodimers of the present disclosure could be effectively directed to the targeting tissues (e.g., tumors) in vivo.

Figure 31:
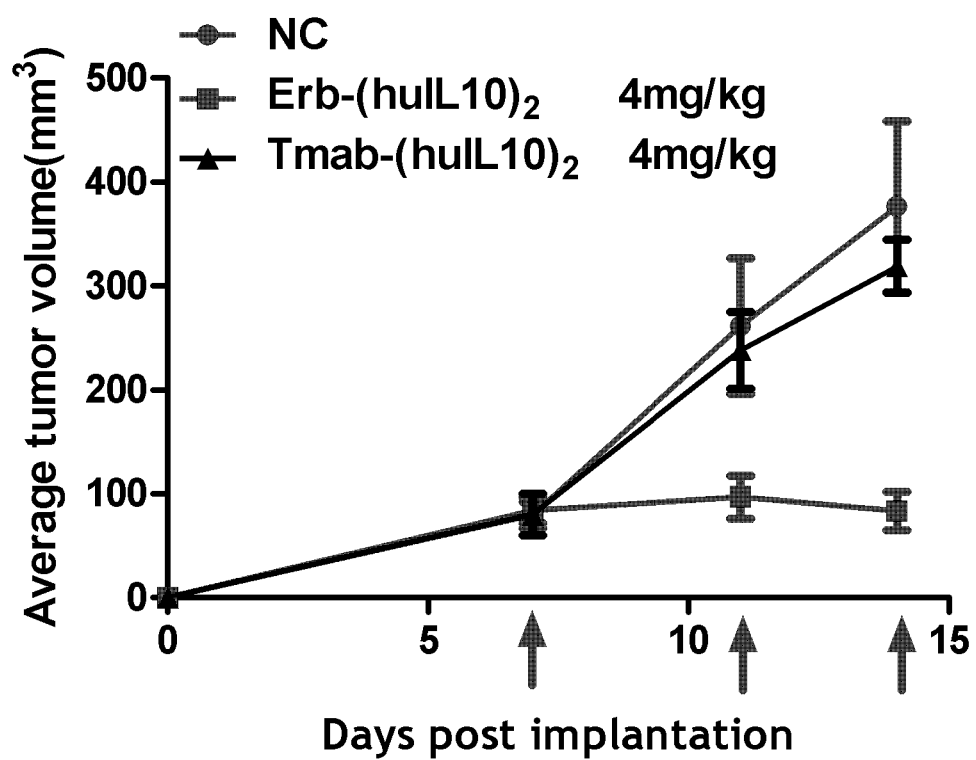
FIG. 31 illustrates a comparison of the in vivo anti-tumor effects between Erb-(huIL10)2 and Tmab-(huIL10)2 in C57BL/6 B16-EGFR mouse model.

To further examine the importance of tumor targeting to the anti-tumor effect of the proteinaceous heterodimers, in vivo anti-tumor effect of Erb-(huIL10)2 and Tmab-(huIL10)2 was tested using C57BL/6 B16-EGFR mouse model. The procedures were similar to those described in Example 9.1. Briefly, 8-week old female C57 BL/6 mice were subcutaneously injected with $7 \times 10^5$ B16-EGFR-SIY cells. After 7 days, tumor volume was measured to be around 45 mm$^3$. The heterodimer Erb-(huIL10)2, Tmab-(huIL10)2 or PBS (negative control) was injected intra-peritoneally (i.p.) at 4 mg/kg. The injection was performed twice per week, and three doses were injected in total. Tumor size was measured twice per week, the volume of the tumors was calculated to obtain a tumor growth curve, as shown in FIG. 31. The results demonstrated that only Erb-(huIL10)2 effectively inhibited tumor growth, indicating the importance of tumor targeting for its in vivo therapeutic effect.

What is claimed is:

1. A proteinaceous complex, comprising (i) a light chain and a heavy chain of an antibody; and (ii) a fusion polypeptide comprising, from N-terminus to C-terminus, an immunoregulator fused to an antibody Fc region, optionally via a linker;
  wherein said light chain of the antibody and said heavy chain of the antibody respectively comprises an amino acid sequence as set forth in: SEQ ID NO: 11 and SEQ ID NO: 13, SEQ ID NO: 15 and SEQ ID NO: 17, SEQ ID NO: 55 and SEQ ID NO: 53, or SEQ ID NO: 65 and SEQ ID NO: 67; and
  said fusion polypeptide comprises an amino acid sequence as set forth in SEQ ID NO: 1, SEQ ID NO: 3, SEQ ID NO: 5, SEQ ID NO: 7, SEQ ID NO: 9, SEQ ID NO: 49, or SEQ ID NO: 51.

2. The proteinaceous complex of claim 1, wherein the immunoregulator is selected from the group consisting of interferon alpha, interferon lamda and interferon beta.

3. The proteinaceous complex of claim 1, wherein the immunoregulator is interleukin 10.

* * * * *

SEQUENCE LISTING

```
<160> NUMBER OF SEQ ID NOS: 79

<210> SEQ ID NO 1
<211> LENGTH: 418
<212> TYPE: PRT
<213> ORGANISM: Mus musculus

<400> SEQUENCE: 1

Met Ala Arg Leu Cys Ala Phe Leu Met Ile Leu Val Met Met Ser Tyr
1               5                   10                  15

Tyr Trp Ser Ala Cys Ser Leu Gly Cys Asp Leu Pro His Thr Tyr Asn
            20                  25                  30

Leu Gly Asn Lys Arg Ala Leu Thr Val Leu Glu Glu Met Arg Arg Leu
        35                  40                  45

Pro Pro Leu Ser Cys Leu Lys Asp Arg Lys Asp Phe Gly Phe Pro Leu
    50                  55                  60

Glu Lys Val Asp Asn Gln Gln Ile Gln Lys Ala Gln Ala Ile Leu Val
65                  70                  75                  80

Leu Arg Asp Leu Thr Gln Gln Ile Leu Asn Leu Phe Thr Ser Lys Asp
                85                  90                  95

Leu Ser Ala Thr Trp Asn Ala Thr Leu Leu Asp Ser Phe Cys Asn Asp
            100                 105                 110

Leu His Gln Gln Leu Asn Asp Leu Lys Ala Cys Val Met Gln Glu Pro
        115                 120                 125

Pro Leu Thr Gln Glu Asp Ser Leu Leu Ala Val Arg Thr Tyr Phe His
    130                 135                 140

Arg Ile Thr Val Tyr Leu Arg Lys Lys Lys His Ser Leu Cys Ala Trp
145                 150                 155                 160

Glu Val Ile Arg Ala Glu Val Trp Arg Ala Leu Ser Ser Ser Thr Asn
                165                 170                 175

Leu Leu Ala Arg Leu Ser Glu Glu Lys Glu Gly Ser Gly Gly Gly Asp
            180                 185                 190

Lys Thr His Thr Cys Pro Pro Cys Pro Ala Pro Glu Leu Leu Gly Gly
        195                 200                 205
```

```
Pro Ser Val Phe Leu Phe Pro Pro Lys Pro Lys Asp Thr Leu Met Ile
    210                 215                 220
Ser Arg Thr Pro Glu Val Thr Cys Val Val Asp Val Ser His Glu
225                 230                 235                 240
Asp Pro Glu Val Lys Phe Asn Trp Tyr Val Asp Gly Val Glu Val His
                245                 250                 255
Asn Ala Lys Thr Lys Pro Arg Glu Glu Gln Tyr Asn Ser Thr Tyr Arg
            260                 265                 270
Val Val Ser Val Leu Thr Val Leu His Gln Asp Trp Leu Asn Gly Lys
        275                 280                 285
Glu Tyr Lys Cys Lys Val Ser Asn Lys Ala Leu Pro Ala Pro Ile Glu
    290                 295                 300
Lys Thr Ile Ser Lys Ala Lys Gly Gln Pro Arg Glu Pro Gln Val Cys
305                 310                 315                 320
Thr Leu Pro Pro Ser Arg Asp Glu Leu Thr Lys Asn Gln Val Ser Leu
                325                 330                 335
Ser Cys Ala Val Lys Gly Phe Tyr Pro Ser Asp Ile Ala Val Glu Trp
            340                 345                 350
Glu Ser Asn Gly Gln Pro Glu Asn Asn Tyr Lys Thr Thr Pro Pro Val
        355                 360                 365
Leu Asp Ser Asp Gly Ser Phe Phe Leu Val Ser Lys Leu Thr Val Asp
    370                 375                 380
Lys Ser Arg Trp Gln Gln Gly Asn Val Phe Ser Cys Ser Val Met His
385                 390                 395                 400
Glu Ala Leu His Asn His Tyr Thr Gln Lys Ser Leu Ser Leu Ser Pro
                405                 410                 415
Gly Lys

<210> SEQ ID NO 2
<211> LENGTH: 1254
<212> TYPE: DNA
<213> ORGANISM: Mus musculus

<400> SEQUENCE: 2
atggctaggc tctgtgcttt cctcatgatc ctggtaatga tgagctacta ctggtcagcc      60
tgttctctag gatgtgacct gcctcacact tataacctcg gaacaagag ggccttgaca     120 gtcctggaag aaatgagaag actccccccct ctttcctgcc tgaaggacag gaaggatttt    180
ggattcccct tggagaaggt tggataaccaa cagatccaga aggctcaagc catccttgtg    240
ctaagagatc ttacccagca gattttgaac ctcttcacat caaaagactt gtctgctact    300
tggaatgcaa ctctactaga ctcattctgc aatgacctcc atcagcagct caatgacctc    360
aaagcctgtg tgatgcagga acctcctctg acccaggaag actccctgct ggctgtgagg    420
acatacttcc acaggatcac tgtgtacctg agaaagaaga acacagcct tgtgcctgg     480 gaggtgatca gagcagaagt ctggagagcc ctctcttcct caaccaactt gctggcaaga    540
ctgagtgagg agaaggaggg atccggtgga ggtgacaaga cccacacctg ccccccctgc    600 cccgccccccg agctgctggg cggccccagc gtgttcctgt tccccccccaa gcccaaggac    660 accctgatga tcagccgcac ccccgaggtg acctgcgtgg tggtggacgt gagccacgag    720
gaccccgagg tgaagttcaa ctggtacgtg gacggcgtgg aggtgcacaa cgccaagacc    780
aagccccgcg aggagcagta caacagcacc taccgcgtgg tgagcgtgct gaccgtgctg    840
caccaggact ggctgaacgg caaggagtac aagtgcaagg tgagcaacaa ggccctgccc    900
```

```
gcccccatcg agaagaccat cagcaaggcc aagggccagc cccgcgagcc ccaggtgtgc      960
accctgcccc ccagccgcga cgagctgacc aagaaccagg tgagcctgag ctgcgccgtg     1020
aagggcttct accccagcga catcgccgtg gagtgggaga gcaacggcca gcccgagaac     1080
aactacaaga ccaccccccc cgtgctggac agcgacggca gcttcttcct ggtgagcaag     1140
ctgaccgtgg acaagagccg ctggcagcag ggcaacgtgt tcagctgcag cgtgatgcac     1200
gaggccctgc acaaccacta cacccagaag agcctgagcc tgagccccgg caag           1254
```

```
<210> SEQ ID NO 3
<211> LENGTH: 420
<212> TYPE: PRT
<213> ORGANISM: Homo sapiens

<400> SEQUENCE: 3

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu Gly Ser Gly Gly
            180                 185                 190

Gly Asp Lys Thr His Thr Cys Pro Pro Cys Pro Ala Pro Glu Leu Leu
        195                 200                 205

Gly Gly Pro Ser Val Phe Leu Phe Pro Pro Lys Pro Lys Asp Thr Leu
    210                 215                 220

Met Ile Ser Arg Thr Pro Glu Val Thr Cys Val Val Val Asp Val Ser
225                 230                 235                 240

His Glu Asp Pro Glu Val Lys Phe Asn Trp Tyr Val Asp Gly Val Glu
                245                 250                 255

Val His Asn Ala Lys Thr Lys Pro Arg Glu Glu Gln Tyr Asn Ser Thr
            260                 265                 270

Tyr Arg Val Val Ser Val Leu Thr Val Leu His Gln Asp Trp Leu Asn
        275                 280                 285

Gly Lys Glu Tyr Lys Cys Lys Val Ser Asn Lys Ala Leu Pro Ala Pro
    290                 295                 300

Ile Glu Lys Thr Ile Ser Lys Ala Lys Gly Gln Pro Arg Glu Pro Gln
305                 310                 315                 320
```

Val Cys Thr Leu Pro Pro Ser Arg Asp Glu Leu Thr Lys Asn Gln Val
                325                 330                 335

Ser Leu Ser Cys Ala Val Lys Gly Phe Tyr Pro Ser Asp Ile Ala Val
                340                 345                 350

Glu Trp Glu Ser Asn Gly Gln Pro Glu Asn Asn Tyr Lys Thr Thr Pro
                355                 360                 365

Pro Val Leu Asp Ser Asp Gly Ser Phe Phe Leu Val Ser Lys Leu Thr
            370                 375                 380

Val Asp Lys Ser Arg Trp Gln Gln Gly Asn Val Phe Ser Cys Ser Val
385                 390                 395                 400

Met His Glu Ala Leu His Asn His Tyr Thr Gln Lys Ser Leu Ser Leu
                405                 410                 415

Ser Pro Gly Lys
            420

<210> SEQ ID NO 4
<211> LENGTH: 1260
<212> TYPE: DNA
<213> ORGANISM: Homo sapiens

<400> SEQUENCE: 4
atggccttga cctttgcttt actggtggcc ctcctggtgc tcagctgcaa gtcaagctgc      60
tctgtgggct gtgatctgcc tcaaacccac agcctgggta gcaggaggac cttgatgctc     120
ctggcacaga tgaggagaat ctctcttttc tcctgcttga aggacagaca tgactttgga     180
tttccccagg aggagtttgg caaccagttc caaaaggctg aaaccatccc tgtcctccat     240
gagatgatcc agcagatctt caatctcttc agcacaaagg actcatctgc tgcttgggat     300
gagaccctcc tagacaaatt ctacactgaa ctctaccagc agctgaatga cctggaagcc     360
tgtgtgatac aggggtgggg ggtgacagag actcccctga tgaaggagga ctccattctg     420
gctgtgagga aatacttcca agaatcact ctctatctga agagaagaa atacagccct     480 tgtgcctggg aggttgtcag agcagaaatc atgagatctt tttctttgtc aacaaacttg     540
caagaaagtt taagaagtaa ggaaggatcc ggtggaggtg acaagaccca cacctgcccc     600
ccctgccccg ccccgagct gctgggcggc ccagcgtgt tcctgttccc cccaagccc     660 aaggacaccc tgatgatcag ccgcaccccc gaggtgacct gcgtggtggt ggacgtgagc     720
cacgaggacc ccgaggtgaa gttcaactgg tacgtggacg gcgtggaggt gcacaacgcc     780
aagaccaagc ccgcgagga gcagtacaac agcacctacc gcgtggtgag cgtgctgacc     840
gtgctgcacc aggactggct gaacggcaag gagtacaagt gcaaggtgag caacaaggcc     900
ctgcccgccc ccatcgagaa gaccatcagc aaggccaagg gccagccccg cgagccccag     960
gtgtgcaccc tgccccccag ccgcgacgag ctgaccaaga accaggtgag cctgagctgc    1020
gccgtgaagg gcttctaccc cagcgacatc gccgtggagt gggagagcaa cggccagccc    1080
gagaacaact acaagaccac cccccccgtg ctggacagcg acggcagctt cttcctggtg    1140
agcaagctga ccgtggacaa gagccgctgg cagcagggca acgtgttcag ctgcagcgtg    1200
atgcacgagg ccctgcacaa ccactacacc cagaagagcc tgagcctgag ccccggcaag    1260

<210> SEQ ID NO 5
<211> LENGTH: 414
<212> TYPE: PRT
<213> ORGANISM: Mus musculus

<400> SEQUENCE: 5

-continued

```
Met Asn Asn Arg Trp Ile Leu His Ala Ala Phe Leu Leu Cys Phe Ser
 1               5                  10                  15

Thr Thr Ala Leu Ser Ile Asn Tyr Lys Gln Leu Gln Leu Gln Glu Arg
             20                  25                  30

Thr Asn Ile Arg Lys Cys Gln Glu Leu Leu Glu Gln Leu Asn Gly Lys
             35                  40                  45

Ile Asn Leu Thr Tyr Arg Ala Asp Phe Lys Ile Pro Met Glu Met Thr
 50                  55                  60

Glu Lys Met Gln Lys Ser Tyr Thr Ala Phe Ala Ile Gln Glu Met Leu
 65              70                  75                  80

Gln Asn Val Phe Leu Val Phe Arg Asn Asn Phe Ser Thr Gly Trp
                 85                  90                  95

Asn Glu Thr Ile Val Val Arg Leu Leu Asp Glu Leu His Gln Gln Thr
                100                 105                 110

Val Phe Leu Lys Thr Val Leu Glu Glu Lys Gln Glu Glu Arg Leu Thr
         115                 120                 125

Trp Glu Met Ser Ser Thr Ala Leu His Leu Lys Ser Tyr Tyr Trp Arg
 130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn Gly Ser Gly Gly Asp Lys Thr His Thr
                180                 185                 190

Cys Pro Pro Cys Pro Ala Pro Glu Leu Leu Gly Gly Pro Ser Val Phe
            195                 200                 205

Leu Phe Pro Pro Lys Pro Lys Asp Thr Leu Met Ile Ser Arg Thr Pro
210                 215                 220

Glu Val Thr Cys Val Val Val Asp Val Ser His Glu Asp Pro Glu Val
225                 230                 235                 240

Lys Phe Asn Trp Tyr Val Asp Gly Val Glu Val His Asn Ala Lys Thr
                245                 250                 255

Lys Pro Arg Glu Glu Gln Tyr Asn Ser Thr Tyr Arg Val Val Ser Val
            260                 265                 270

Leu Thr Val Leu His Gln Asp Trp Leu Asn Gly Lys Glu Tyr Lys Cys
            275                 280                 285

Lys Val Ser Asn Lys Ala Leu Pro Ala Pro Ile Glu Lys Thr Ile Ser
    290                 295                 300

Lys Ala Lys Gly Gln Pro Arg Glu Pro Gln Val Cys Thr Leu Pro Pro
305                 310                 315                 320

Ser Arg Asp Glu Leu Thr Lys Asn Gln Val Ser Leu Ser Cys Ala Val
                325                 330                 335

Lys Gly Phe Tyr Pro Ser Asp Ile Ala Val Glu Trp Glu Ser Asn Gly
            340                 345                 350

Gln Pro Glu Asn Asn Tyr Lys Thr Thr Pro Pro Val Leu Asp Ser Asp
        355                 360                 365

Gly Ser Phe Phe Leu Val Ser Lys Leu Thr Val Asp Lys Ser Arg Trp
370                 375                 380

Gln Gln Gly Asn Val Phe Ser Cys Ser Val Met His Glu Ala Leu His
385                 390                 395                 400

Asn His Tyr Thr Gln Lys Ser Leu Ser Leu Ser Pro Gly Lys
                405                 410
```

<210> SEQ ID NO 6
<211> LENGTH: 1242
<212> TYPE: DNA
<213> ORGANISM: Mus musculus

<400> SEQUENCE: 6

| | | |
|---|---|---|
| atgaacaaca ggtggattct ccacgctgcg ttcctgctgt gcttctccac cacagccctc | 60 |
| tccatcaact ataagcagct ccagctccaa gaaaggacga acattcggaa atgtcaggag | 120 |
| ctcctggagc agctgaatgg aaagatcaac ctcacctaca gggcggactt caagatccct | 180 |
| atggagatga cggagaagat gcagaagagt tacactgcct ttgccatcca agagatgctc | 240 |
| cagaatgtct ttcttgtctt cagaaacaat ttctccagca ctgggtggaa tgagactatt | 300 |
| gttgtacgtc tcctggatga actccaccag cagacagtgt ttctgaagac agtactagag | 360 |
| gaaaagcaag aggaaagatt gacgtgggag atgtcctcaa ctgctctcca cttgaagagc | 420 |
| tattactgga gggtgcaaag gtatcttaaa ctcatgaagt acaacagcta cgcctggatg | 480 |
| gtggtccgag cagagatctt caggaacttt ctcatcattc gaagacttac cagaaacttc | 540 |
| caaaacggat ccggtggagg tgacaagacc cacacctgcc cccctgccc cgccccgag | 600 |
| ctgctgggcg gccccagcgt gttcctgttc ccccccaagc caaggacac cctgatgatc | 660 |
| agccgcaccc ccgaggtgac ctgcgtggtg gtggacgtga gccacgagga ccccgaggtg | 720 |
| aagttcaact ggtacgtgga cggcgtggag gtgcacaacg ccaagaccaa gccccgcgag | 780 |
| gagcagtaca acagcaccta ccgcgtggtg agcgtgctga ccgtgctgca ccaggactgg | 840 |
| ctgaacggca aggagtacaa gtgcaaggtg agcaacaagg ccctgcccgc ccccatcgag | 900 |
| aagaccatca gcaaggccaa gggccagccc cgcgagcccc aggtgtgcac cctgcccccc | 960 |
| agccgcgacg agctgaccaa gaaccaggtg agcctgagct cgccgtgaa gggcttctac | 1020 |
| cccagcgaca tcgccgtgga gtgggagagc aacggccagc ccgagaacaa ctacaagacc | 1080 |
| accccccccg tgctggacag cgacggcagc ttcttcctgg tgagcaagct gaccgtggac | 1140 |
| aagagccgct ggcagcaggg caacgtgttc agctgcagcg tgatgcacga ggccctgcac | 1200 |
| aaccactaca cccagaagag cctgagcctg agccccggca ag | 1242 |

<210> SEQ ID NO 7
<211> LENGTH: 432
<212> TYPE: PRT
<213> ORGANISM: Homo sapiens

<400> SEQUENCE: 7

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

| | | | | | | | | | | | | |
|---|---|---|---|---|---|---|---|---|---|---|---|---|
|Val|Leu|Asp|Gln|Pro|Leu|His|Thr|Leu|His|His|Ile|Leu|Ser|Gln|Leu|
| | |115| | | |120| | | |125| | | | | |

Val Leu Asp Gln Pro Leu His Thr Leu His His Ile Leu Ser Gln Leu
             115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr Gly Ser Gly Gly Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
            245                 250                 255

Glu Val Lys Phe Asn Trp Tyr Val Asp Gly Val Glu Val His Asn Ala
                260                 265                 270

Lys Thr Lys Pro Arg Glu Glu Gln Tyr Asn Ser Thr Tyr Arg Val Val
    275                 280                 285

Ser Val Leu Thr Val Leu His Gln Asp Trp Leu Asn Gly Lys Glu Tyr
        290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Cys Thr Leu
            325                 330                 335

Pro Pro Ser Arg Asp Glu Leu Thr Lys Asn Gln Val Ser Leu Ser Cys
                340                 345                 350

Ala Val Lys Gly Phe Tyr Pro Ser Asp Ile Ala Val Glu Trp Glu Ser
    355                 360                 365

Asn Gly Gln Pro Glu Asn Asn Tyr Lys Thr Thr Pro Pro Val Leu Asp
370                 375                 380

Ser Asp Gly Ser Phe Phe Leu Val Ser Lys Leu Thr Val Asp Lys Ser
385                 390                 395                 400

Arg Trp Gln Gln Gly Asn Val Phe Ser Cys Ser Val Met His Glu Ala
            405                 410                 415

Leu His Asn His Tyr Thr Gln Lys Ser Leu Ser Leu Ser Pro Gly Lys
                420                 425                 430

<210> SEQ ID NO 8
<211> LENGTH: 1296
<212> TYPE: DNA
<213> ORGANISM: Homo sapiens

<400> SEQUENCE: 8

```
atggctgcag cttggaccgt ggtgctggtg actttggtgc taggcttggc cgtggcaggc     60
cctgtcccca cttccaagcc caccacaact gggaagggct gccacattgg caggttcaaa    120
tctctgtcac acaggagct agcgagcttc aagaaggcca gggacgcctt ggaagagtca    180
ctcaagctga aaaactggag ttgcagtctc ctgtcttcc cgggaattg gacctgagg      240
cttctccagg tgagggagcg ccctgtggcc ttggaggctg agctggccct gacgctgaag    300
gtcctggagg ccgctgctgg cccagccctg aggacgtcc tagaccagcc ccttcacacc    360
```

-continued

```
ctgcaccaca tcctctccca gctccaggcc tgtatccagc ctcagcccac agcagggccc      420
aggccccggg gccgcctcca ccactggctg caccggctcc aggaggcccc caaaaaggag      480
tccgctggct gcctggaggc atctgtcacc ttcaacctct tccgcctcct cacgcgagac      540
ctcaaatatg tggccgatgg gaacctgtgt ctgagaacgt caacccaccc tgagtccacc      600
ggatccggtg gaggtgacaa gacccacacc tgccccccct gccccgcccc cgagctgctg      660
ggcggcccca gcgtgttcct gttcccccc aagcccaagg acaccctgat gatcagccgc       720
acccccgagg tgacctgcgt ggtggtggac gtgagccacg aggaccccga ggtgaagttc      780
aactggtacg tggacggcgt ggaggtgcac aacgccaaga ccaagcccg cgaggagcag       840 tacaacagca cctaccgcgt ggtgagcgtg ctgaccgtgc tgcaccagga ctggctgaac      900
ggcaaggagt acaagtgcaa ggtgagcaac aaggccctgc cgccccat cgagaagacc       960 atcagcaagg ccaagggcca gccccgcgag ccccaggtgt gcaccctgcc cccagccgc     1020 gacgagctga ccaagaacca ggtgagcctg agctgcgccg tgaagggctt ctaccccagc    1080
gacatcgccg tggagtggga gagcaacggc cagcccgaga caactacaa gaccaccccc     1140 cccgtgctgg acagcgacgg cagcttcttc ctggtgagca agctgaccgt ggacaagagc    1200
cgctggcagc agggcaacgt gttcagctgc agcgtgatgc acgaggccct gcacaaccac    1260
tacacccaga gagcctgag cctgagcccc ggcaag                              1296
```

<210> SEQ ID NO 9
<211> LENGTH: 419
<212> TYPE: PRT
<213> ORGANISM: Homo sapiens

<400> SEQUENCE: 9

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Gly Ser Gly Gly Gly
            180                 185                 190

Asp Lys Thr His Thr Cys Pro Pro Cys Pro Ala Pro Glu Leu Leu Gly
        195                 200                 205

-continued

Gly Pro Ser Val Phe Leu Phe Pro Lys Pro Lys Asp Thr Leu Met
    210                 215                 220

Ile Ser Arg Thr Pro Glu Val Thr Cys Val Val Asp Val Ser His
225                 230                 235                 240

Glu Asp Pro Glu Val Lys Phe Asn Trp Tyr Val Asp Gly Val Glu Val
                245                 250                 255

His Asn Ala Lys Thr Lys Pro Arg Glu Glu Gln Tyr Asn Ser Thr Tyr
            260                 265                 270

Arg Val Val Ser Val Leu Thr Val Leu His Gln Asp Trp Leu Asn Gly
        275                 280                 285

Lys Glu Tyr Lys Cys Lys Val Ser Asn Lys Ala Leu Pro Ala Pro Ile
    290                 295                 300

Glu Lys Thr Ile Ser Lys Ala Lys Gly Gln Pro Arg Glu Pro Gln Val
305                 310                 315                 320

Cys Thr Leu Pro Pro Ser Arg Asp Glu Leu Thr Lys Asn Gln Val Ser
                325                 330                 335

Leu Ser Cys Ala Val Lys Gly Phe Tyr Pro Ser Asp Ile Ala Val Glu
            340                 345                 350

Trp Glu Ser Asn Gly Gln Pro Glu Asn Asn Tyr Lys Thr Thr Pro Pro
        355                 360                 365

Val Leu Asp Ser Asp Gly Ser Phe Phe Leu Val Ser Lys Leu Thr Val
    370                 375                 380

Asp Lys Ser Arg Trp Gln Gln Gly Asn Val Phe Ser Cys Ser Val Met
385                 390                 395                 400

His Glu Ala Leu His Asn His Tyr Thr Gln Lys Ser Leu Ser Leu Ser
                405                 410                 415

Pro Gly Lys

<210> SEQ ID NO 10
<211> LENGTH: 1178
<212> TYPE: DNA
<213> ORGANISM: Homo sapiens

<400> SEQUENCE: 10
ttggattcct acaaagaagc agcaattttc agtgtcagaa gctcctgtgg caattgaatg      60
ggaggcttga atactgcctc aaggacagga tgaactttga catccctgag agattaagc     120 agctgcagca gttccagaag gaggacgccg cattgaccat ctatgagatg ctccagaaca     180
tctttgctat tttcagacaa gattcatcta gcactggctg aatgagact attgttgaga     240 acctcctggc taatgtctat catcagataa accatctgaa gacagtcctg gaagaaaaac     300
tggagaaaga agatttcacc aggggaaaac tcatgagcag tctgcacctg aaagatatt     360 atgggaggat tctgcattac ctgaaggcca aggagtacag tcactgtgcc tggaccatag     420
tcagagtgga aatcctaagg aactttttact tcattaacag acttacaggt tacctccgaa     480
acggatccgg tggaggtgac aagacccaca cctgccccc ctgccccgcc cccgagctgc     540
tgggcggccc cagcgtgttc ctgttccccc ccaagcccaa ggacaccctg atgatcagcc     600
gcacccccga ggtgacctgc gtggtggtgg acgtgagcca cgaggacccc gaggtgaagt     660
tcaactggta cgtggacggc gtggaggtgc acaacgccaa gaccaagccc cgcgaggagc     720
agtacaacag cacctaccgc gtggtgagcg tgctgaccgt gctgcaccag gactggctga     780
acggcaagga gtacaagtgc aaggtgagca acaaggccct gccgccccc atcgagaaga     840 ccatcagcaa ggccaagggc cagccccgcg agccccaggt gtgcaccctg ccccccagcc     900

```
gcgacgagct gaccaagaac caggtgagcc tgagctgcgc cgtgaagggc ttctacccca    960
gcgacatcgc cgtggagtgg gagagcaacg gccagcccga gaacaactac aagaccaccc   1020 ccccgtgct ggacagcgac ggcagcttct tcctggtgag caagctgacc gtggacaaga   1080
gccgctggca gcagggcaac gtgttcagct gcagcgtgat gcacgaggcc ctgcacaacc   1140
actacaccca aagagcctg agcctgagcc ccggcaag                            1178
```

<210> SEQ ID NO 11
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 11

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 12
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 12

```
gacatcctgc tgacccagag ccccgtgatc ctgagcgtga gccccggcga gcgcgtgagc     60
ttcagctgcc gcgccagcca gagcatcggc accaacatcc actggtacca gcagcgcacc    120
aacggcagcc ccgcctgct gatcaagtac gccagcgaga gcatcagcgg catccccagc    180
```

-continued

```
cgcttcagcg gcagcggcag cggcaccgac ttcaccctga gcatcaacag cgtggagagc    240
gaggacatcg ccgactacta ctgccagcag aacaacaact ggcccaccac cttcggcgcc    300
ggcaccaagc tggagctgaa gcgcaccgtg gccgccccca gcgtgttcat cttccccccc    360
agcgacgagc agctgaagag cggcaccgcc agcgtggtgt gcctgctgaa caacttctac    420
ccccgcgagg ccaaggtgca gtggaaggtg gacaacgccc tgcagagcgg caacagccag    480
gagagcgtga ccgagcagga cagcaaggac agcacctaca gcctgagcag caccctgacc    540
ctgagcaagg ccgactacga gaagcacaag gtgtacgcct gcgaggtgac ccaccagggc    600
ctgagcagcc ccgtgaccaa gagcttcaac cgcggcgagt gc                       642

<210> SEQ ID NO 13
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 13

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Cys Arg Asp Glu Leu Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 14
<211> LENGTH: 1347
<212> TYPE: DNA
<213> ORGANISM: Artificial Sequence
<220> FEATURE:
<223> OTHER INFORMATION: Synthetic polynucleotide

<400> SEQUENCE: 14
caggtgcagc tgaagcagag cggccccggc ctggtgcagc ccagccagag cctgagcatc    60
acctgcaccg tgagcggctt cagcctgacc aactacggcg tgcactgggt gcgccagagc   120
cccggcaagg gcctggagtg gctgggcgtg atctggagcg gcggcaacac cgactacaac   180 accccttca ccagccgcct gagcatcaac aaggacaaca gcaagagcca ggtgttcttc   240
aagatgaaca gcctgcagag caacgacacc gccatctact actgcgcccg cgccctgacc   300
tactacgact acgagttcgc ctactggggc cagggcaccc tggtgaccgt gagcgccgcc   360
agcaccaagg gcccagcgt gttccccctg gccccagca gcaagagcac cagcggcggc   420
accgccgccc tgggctgcct ggtgaaggac tacttccccg agcccgtgac cgtgagctgg   480
aacagcggcg ccctgaccag cggcgtgcac accttccccg ccgtgctgca gagcagcggc   540
ctgtacagcc tgagcagcgt ggtgaccgtg ccagcagca gcctgggcac ccagacctac   600
atctgcaacg tgaaccacaa gcccagcaac accaaggtgg acaagcgcgt ggagcccaag   660
agctgcgaca gacccacac tgccccccc tgccccgccc cgagctgct gggcggcccc   720 agcgtgttcc tgttcccccc caagcccaag gacaccctga tgatcagccg cacccccgag   780
gtgacctgcg tggtggtgga cgtgagccac gaggacccccg aggtgaagtt caactggtac   840
gtggacggcg tggaggtgca caacgccaag accaagcccc gcgaggagca gtacaacagc   900
acctaccgcg tggtgagcgt gctgaccgtg ctgcaccagg actggctgaa cggcaaggag   960
tacaagtgca aggtgagcaa caaggccctg cccgccccca tcgagaagac catcagcaag  1020
gccaagggcc agccccgcga gccccaggtg tacaccctgc cccctgccg cgacgagctg  1080

```
accaagaacc aggtgagcct gtggtgcctg gtgaagggct tctaccccag cgacatcgcc      1140
gtggagtggg agagcaacgg ccagcccgag aacaactaca agaccacccc ccccgtgctg      1200
gacagcgacg gcagcttctt cctgtacagc aagctgaccg tggacaagag ccgctggcag      1260
cagggcaacg tgttcagctg cagcgtgatg cacgaggccc tgcacaacca ctacacccag      1320
aagagcctga gcctgagccc cggcaag                                         1347

<210> SEQ ID NO 15
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 16
gacatccaaa tgacacagtc accctcaagc ctgagcgcct ccgtgggcga cagggtgacc      60
attacctgta gagcctcaca ggacgtgaac actgccgttg catggtatca acagaagcct     120
ggtaaagcac ccaaactgct catttatagc gcctcctttc tgtactctgg ggtgccttcc     180
cggttttctg gctcccggag cggcaccgac tttacactga ctatctcttc cctccagccc     240
```

```
gaagatttg  caacatacta  ctgtcagcag  cactatacta  ctcctccaac  attcggccag    300
gggacaaaag  tggagataaa  gcgcaccgtg  gccgcccca   gcgtgttcat  cttccccccc   360
agcgacgagc  agctgaagag  cggcaccgcc  agcgtggtgt  gcctgctgaa  caacttctac   420
ccccgcgagg  ccaaggtgca  gtggaaggtg  gacaacgccc  tgcagagcgg  caacagccag   480
gagagcgtga  ccgagcagga  cagcaaggac  agcacctaca  gcctgagcag  caccctgacc   540
ctgagcaagg  ccgactacga  gaagcacaag  gtgtacgcct  gcgaggtgac  ccaccagggc   600
ctgagcagcc  ccgtgaccaa  gagcttcaac  cgcggcgagt  gc                      642
```

<210> SEQ ID NO 17
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 18
<211> LENGTH: 1350
<212> TYPE: DNA
<213> ORGANISM: Artificial Sequence
<220> FEATURE:
<223> OTHER INFORMATION: Synthetic polynucleotide

<400> SEQUENCE: 18
gaagtccagc tggtcgaatc cggtggcggg ctggtccagc caggaggatc tctgagactg    60
tcctgcgccg caagcggctt caacatcaag gatacataca tccactgggt gaggcaggca   120
cccggcaaag gcctggagtg gtggcccgg atctacccaa ccaacggtta taccaggtat   180
gccgactcag tcaaaggcag gtttactatt tctgctgaca catcaaagaa tacagcctac   240
ctgcaaatga atagcctgag ggctgaagat accgctgtgt actactgctc cagatgggga   300
ggtgatggct tttatgccat ggattattgg ggacaaggca cactcgtgac cgtttcttct   360
gccagcacca agggcccag cgtgttcccc ctggccccca gcagcaagag caccagcggc   420
ggcaccgccg ccctgggctg cctggtgaag gactacttcc ccgagcccgt gaccgtgagc   480
tggaacagcg gcgccctgac cagcggcgtg cacaccttcc ccgccgtgct gcagagcagc   540
ggcctgtaca gcctgagcag cgtggtgacc gtgcccagca gcagcctggg cacccagacc   600
tacatctgca acgtgaacca caagcccagc aacaccaagg tggacaagcg cgtggagccc   660
aagagctgcg acaagaccca cacctgcccc cctgccccg cccccgagct gctgggcggc   720
cccagcgtgt tcctgttccc ccccaagccc aaggacaccc tgatgatcag ccgcacccccc   780 gaggtgacct gcgtggtggt ggacgtgagc cacgaggacc ccgaggtgaa gttcaactgg   840
tacgtggacg gcgtggaggt gcacaacgcc aagaccaagc ccgcgagga gcagtacaac   900 agcacctacc gcgtggtgag cgtgctgacc gtgctgcacc aggactggct gaacggcaag   960
gagtacaagt gcaaggtgag caacaaggcc ctgcccgccc ccatcgagaa gaccatcagc  1020
aaggccaagg gccagccccg cgagccccag gtgtacaccc tgcccccctg ccgcgacgag  1080
```

```
ctgaccaaga accaggtgag cctgtggtgc ctggtgaagg gcttctaccc cagcgacatc    1140
gccgtggagt gggagagcaa cggccagccc gagaacaact acaagaccac ccccccgtg     1200 ctggacagcg acggcagctt cttcctgtac agcaagctga ccgtggacaa gagccgctgg    1260
cagcagggca cgtgttcag ctgcagcgtg atgcacgagg ccctgcacaa ccactacacc     1320
cagaagagcc tgagcctgag ccccggcaag                                     1350
```

<210> SEQ ID NO 19
<211> LENGTH: 630
<212> TYPE: PRT
<213> ORGANISM: Artificial Sequence
<220> FEATURE:
<223> OTHER INFORMATION: Synthetic polypeptide

<400> SEQUENCE: 19

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Ser Gly Gly Gly Gly Ser Gly Gly Gly Ser Gly Gly Gly Gly
            450                 455                 460

Ser Gly Gly Gly Gly Ile Asn Tyr Lys Gln Leu Gln Leu Gln Glu Arg
465                 470                 475                 480

Thr Asn Ile Arg Lys Cys Gln Glu Leu Leu Glu Gln Leu Asn Gly Lys
            485                 490                 495

Ile Asn Leu Thr Tyr Arg Ala Asp Phe Lys Ile Pro Met Glu Met Thr
            500                 505                 510

Glu Lys Met Gln Lys Ser Tyr Thr Ala Phe Ala Ile Gln Glu Met Leu
            515                 520                 525

Gln Asn Val Phe Leu Val Phe Arg Asn Asn Phe Ser Ser Thr Gly Trp
            530                 535                 540

Asn Glu Thr Ile Val Val Arg Leu Leu Asp Glu Leu His Gln Gln Thr
545                 550                 555                 560

Val Phe Leu Lys Thr Val Leu Glu Glu Lys Gln Glu Arg Leu Thr
            565                 570                 575

Trp Glu Met Ser Ser Thr Ala Leu His Leu Lys Ser Tyr Tyr Trp Arg
            580                 585                 590

Val Gln Arg Tyr Leu Lys Leu Met Lys Tyr Asn Ser Tyr Ala Trp Met
            595                 600                 605

Val Val Arg Ala Glu Ile Phe Arg Asn Phe Leu Ile Ile Arg Arg Leu
            610                 615                 620

Thr Arg Asn Phe Gln Asn
625                 630

<210> SEQ ID NO 20
<211> LENGTH: 1890
<212> TYPE: DNA
<213> ORGANISM: Artificial Sequence
<220> FEATURE:
<223> OTHER INFORMATION: Synthetic polynucleotide

<400> SEQUENCE: 20
caggtgcagc tgaagcagag cggccccggc ctggtgcagc ccagccagag cctgagcatc      60
acctgcaccg tgagcggctt cagcctgacc aactacggcg tgcactgggt gcgccagagc     120
cccggcaagg gcctggagtg gctgggcgtg atctggagcg gcggcaacac cgactacaac     180 accccccttca ccagccgcct gagcatcaac aaggacaaca gcaagagcca ggtgttcttc     240

| | |
|---|---|
| aagatgaaca gcctgcagag caacgacacc gccatctact actgcgcccg cgccctgacc | 300 |
| tactacgact acgagttcgc ctactggggc cagggcaccc tggtgaccgt gagcgccgcc | 360 |
| agcaccaagg gcccagcgt gttccccctg gcccccagca gcaagagcac cagcggcggc | 420 |
| accgccgccc tgggctgcct ggtgaaggac tacttccccg agcccgtgac cgtgagctgg | 480 |
| aacagcggcg ccctgaccag cggcgtgcac accttccccg ccgtgctgca gagcagcggc | 540 |
| ctgtacagcc tgagcagcgt ggtgaccgtg cccagcagca gcctgggcac ccagacctac | 600 |
| atctgcaacg tgaaccacaa gcccagcaac accaaggtgg acaagcgcgt ggagcccaag | 660 |
| agctgcgata gacacacac ctgccctcca tgccccgcac ctgaactcct gggcgggcct | 720 |
| tccgttttcc tgtttcctcc caagcccaag gatacactga tgattagccg cacccccgaa | 780 |
| gtcacttgcg tggtggtgga tgtgagccat gaagatccag aagttaagtt taactggtat | 840 |
| gtggacgggg tcgaggtgca caatgctaaa acaaagccca gggaggagca atataactcc | 900 |
| acatacagag tggtgtccgt tctgacagtc ctgcaccagg actggctgaa cgggaaggaa | 960 |
| tacaagtgca aggtgtctaa taaggcactg ccagccccca tagagaagac aatctctaaa | 1020 |
| gctaaaggcc aaccacgcga gcctcaggtc tacacactgc caccatccag ggacgaactg | 1080 |
| accaagaatc aggtgagcct gacttgtctc gtcaaaggat tctacccaag cgacatcgcc | 1140 |
| gtggagtggg aatccaacgg ccaaccagag aacaactaca agaccacccc accagtcctg | 1200 |
| gactctgatg gagctttttt cctgtattcc aagctgacag tggacaagtc tcggtggcaa | 1260 |
| cagggcaacg tgttcagctg ctccgtgatg catgaagccc tgcataacca ctatacccag | 1320 |
| aaaagcctca gcctgtcccc cgggaaaagc ggcggcggcg gcagcggggg cggcggcagc | 1380 |
| ggaggaggcg gcagcggagg aggcggcatc aactataagc agctccagct ccaagaaagg | 1440 |
| acgaacattc ggaaatgtca ggagctcctg agcagctga atggaaagat caacctcacc | 1500 |
| tacagggcgg acttcaagat ccctatggag atgacggaga agatgcagaa gagttacact | 1560 |
| gcctttgcca tccaagagat gctccagaat gtctttcttg tcttcagaaa caatttctcc | 1620 |
| agcactgggt ggaatgagac tattgttgta cgtctcctgg atgaactcca ccagcagaca | 1680 |
| gtgtttctga agacagtact agaggaaaag caagaggaaa gattgacgtg ggagatgtcc | 1740 |
| tcaactgctc tccacttgaa gagctattac tggagggtgc aaaggtatct taaactcatg | 1800 |
| aagtacaaca gctacgcctg gatggtggtc cgagcagaga tcttcaggaa ctttctcatc | 1860 |
| attcgaagac ttaccagaaa cttccaaaac | 1890 |

<210> SEQ ID NO 21
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 21

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg

-continued

```
             65                  70                  75                  80
Leu Leu Gln Val Arg Glu Arg Pro Val Ala Leu Glu Ala Glu Leu Ala
                 85                  90                  95
Leu Thr Leu Lys Val Leu Glu Ala Ala Ala Gly Pro Ala Leu Glu Asp
                100                 105                 110
Val Leu Asp Gln Pro Leu His Thr Leu His His Ile Leu Ser Gln Leu
                115                 120                 125
Gln Ala Cys Ile Gln Pro Gln Pro Thr Ala Gly Pro Arg Pro Arg Gly
                130                 135                 140
Arg Leu His His Trp Leu His Arg Leu Gln Glu Ala Pro Lys Lys Glu
145                 150                 155                 160
Ser Ala Gly Cys Leu Glu Ala Ser Val Thr Phe Asn Leu Phe Arg Leu
                165                 170                 175
Leu Thr Arg Asp Leu Lys Tyr Val Ala Asp Gly Asn Leu Cys Leu Arg
                180                 185                 190
Thr Ser Thr His Pro Glu Ser Thr Gly Ser Gly Gly Gln Val Gln
                195                 200                 205
Leu Lys Gln Ser Gly Pro Gly Leu Val Gln Pro Ser Gln Ser Leu Ser
                210                 215                 220
Ile Thr Cys Thr Val Ser Gly Phe Ser Leu Thr Asn Tyr Gly Val His
225                 230                 235                 240
Trp Val Arg Gln Ser Pro Gly Lys Gly Leu Glu Trp Leu Gly Val Ile
                245                 250                 255
Trp Ser Gly Gly Asn Thr Asp Tyr Asn Thr Pro Phe Thr Ser Arg Leu
                260                 265                 270
Ser Ile Asn Lys Asp Asn Ser Lys Ser Gln Val Phe Phe Lys Met Asn
                275                 280                 285
Ser Leu Gln Ser Asn Asp Thr Ala Ile Tyr Tyr Cys Ala Arg Ala Leu
                290                 295                 300
Thr Tyr Tyr Asp Tyr Glu Phe Ala Tyr Trp Gly Gln Gly Thr Leu Val
305                 310                 315                 320
Thr Val Ser Ala Ala Ser Thr Lys Gly Pro Ser Val Phe Pro Leu Ala
                325                 330                 335
Pro Ser Ser Lys Ser Thr Ser Gly Gly Thr Ala Ala Leu Gly Cys Leu
                340                 345                 350
Val Lys Asp Tyr Phe Pro Glu Pro Val Thr Val Ser Trp Asn Ser Gly
                355                 360                 365
Ala Leu Thr Ser Gly Val His Thr Phe Pro Ala Val Leu Gln Ser Ser
                370                 375                 380
Gly Leu Tyr Ser Leu Ser Ser Val Val Thr Val Pro Ser Ser Ser Leu
385                 390                 395                 400
Gly Thr Gln Thr Tyr Ile Cys Asn Val Asn His Lys Pro Ser Asn Thr
                405                 410                 415
Lys Val Asp Lys Arg Val Glu Pro Lys Ser Cys Asp Lys Thr His Thr
                420                 425                 430
Cys Pro Pro Cys Pro Ala Pro Glu Leu Leu Gly Gly Pro Ser Val Phe
                435                 440                 445
Leu Phe Pro Pro Lys Pro Lys Asp Thr Leu Met Ile Ser Arg Thr Pro
                450                 455                 460
Glu Val Thr Cys Val Val Val Asp Val Ser His Glu Asp Pro Glu Val
465                 470                 475                 480
Lys Phe Asn Trp Tyr Val Asp Gly Val Glu Val His Asn Ala Lys Thr
                485                 490                 495
```

```
Lys Pro Arg Glu Glu Gln Tyr Asn Ser Thr Tyr Arg Val Val Ser Val
                500                 505                 510

Leu Thr Val Leu His Gln Asp Trp Leu Asn Gly Lys Glu Tyr Lys Cys
            515                 520                 525

Lys Val Ser Asn Lys Ala Leu Pro Ala Pro Ile Glu Lys Thr Ile Ser
        530                 535                 540

Lys Ala Lys Gly Gln Pro Arg Glu Pro Gln Val Tyr Thr Leu Pro Pro
545                 550                 555                 560

Ser Arg Asp Glu Leu Thr Lys Asn Gln Val Ser Leu Thr Cys Leu Val
                565                 570                 575

Lys Gly Phe Tyr Pro Ser Asp Ile Ala Val Glu Trp Glu Ser Asn Gly
            580                 585                 590

Gln Pro Glu Asn Asn Tyr Lys Thr Thr Pro Pro Val Leu Asp Ser Asp
        595                 600                 605

Gly Ser Phe Phe Leu Tyr Ser Lys Leu Thr Val Asp Lys Ser Arg Trp
610                 615                 620

Gln Gln Gly Asn Val Phe Ser Cys Ser Val Met His Glu Ala Leu His
625                 630                 635                 640

Asn His Tyr Thr Gln Lys Ser Leu Ser Leu Ser Pro Gly Lys
                645                 650
```

<210> SEQ ID NO 22
<211> LENGTH: 1962
<212> TYPE: DNA
<213> ORGANISM: Artificial Sequence
<220> FEATURE:
<223> OTHER INFORMATION: Synthetic polynucleotide

<400> SEQUENCE: 22

```
atggctgcag cttggaccgt ggtgctggtg actttggtgc taggcttggc cgtggcaggc      60
cctgtcccca cttccaagcc caccacaact gggaagggct gccacattgg caggttcaaa     120
tctctgtcac acaggagct agcgagcttc aagaaggcca gggacgcctt ggaagagtca     180
ctcaagctga aaaactggag ttgcagtctt cctgtcttcc ccgggaattg ggacctgagg     240
cttctccagg tgagggagcg ccctgtggcc ttggaggctg agctggccct gacgctgaag     300
gtcctggagg ccgctgctgg cccagccctg aggacgtcc tagaccagcc ccttcacacc     360
ctgcaccaca tcctctccca gctccaggcc tgtatccagc tcagcccac agcagggccc     420
aggccccggg ccgcctcca ccactggctg caccggctcc aggaggcccc caaaaaggag     480
tccgctggct gcctggaggc atctgtcacc ttcaacctct ccgcctcct cacgcgagac     540
ctcaaatatg tggccgatgg gaacctgtgt ctgagaacgt caacccaccc tgagtccacc     600
ggatccggtg gaggtcaggt gcagctgaag cagagcggcc ccggcctggt gcagcccagc     660
cagagcctga gcatcacctg caccgtgagc ggcttcagcc tgaccaacta cggcgtgcac     720
tgggtgcgcc agagccccgg caagggcctg gagtggctgg gcgtgatctg gagcggcggc     780
aacaccgact acaacacccc cttcaccagc cgcctgagca tcaacaagga caacagcaag     840
agccaggtgt tcttcaagat gaacagcctg cagagcaacg acaccgccat ctactactgc     900
gccccgcccc tgacctacta cgactacgag ttcgcctact ggggccaggg caccctggtg     960
accgtgagcg ccgccagcac caagggcccc agcgtgttcc ccctggcccc cagcagcaag    1020
agcaccagcg gcggcaccgc cgccctgggc tgcctggtga aggactactt ccccgagccc    1080
gtgaccgtga gctggaacag cggcgccctg accagcggcg tgcacacctt ccccgccgtg    1140
```
ctgcagagca gcggcctgta cagcctgagc agcgtggtga ccgtgcccag cagcagcctg    1200
ggcacccaga cctacatctg caacgtgaac cacaagccca gcaacaccaa ggtggacaag    1260
cgcgtggagc ccaagagctg cgataagaca cacacctgcc ctccatgccc cgcacctgaa    1320
ctcctgggcg gccttccgt tttcctgttt cctcccaagc ccaaggatac actgatgatt    1380
agccgcaccc ccgaagtcac ttgcgtggtg gtggatgtga gccatgaaga tccagaagtt    1440
aagtttaact ggtatgtgga cggggtcgag gtgcacaatg ctaaaacaaa gcccagggag    1500
gagcaatata actccacata cagagtggtg tccgttctga cagtcctgca ccaggactgg    1560
ctgaacggga aggaatacaa gtgcaaggtg tctaataagg cactgccagc ccccatagag    1620
aagacaatct ctaaagctaa aggccaacca cgcgagcctc aggtctacac actgccacca    1680
tccagggacg aactgaccaa gaatcaggtg agcctgactt gtctcgtcaa aggattctac    1740
ccaagcgaca tcgccgtgga gtgggaatcc aacggccaac agagaacaa ctacaagacc    1800 acccccaccag tcctggactc tgatgggagc ttttttcctgt attccaagct gacagtggac    1860
aagtctcggt ggcaacaggg caacgtgttc agctgctccg tgatgcatga agccctgcat    1920
aaccactata cccagaaaag cctcagcctg tccccggga aa    1962

<210> SEQ ID NO 23
<211> LENGTH: 635
<212> TYPE: PRT
<213> ORGANISM: Artificial Sequence
<220> FEATURE:
<223> OTHER INFORMATION: Synthetic polypeptide

<400> SEQUENCE: 23

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Ser Gly Gly Gly Gly Ser Gly Gly Gly Gly Ser Gly Gly Gly Gly
    450                 455                 460

Ser Gly Gly Gly Gly Met Ser Tyr Asn Leu Leu Gly Phe Leu Gln Arg
465                 470                 475                 480

Ser Ser Asn Phe Gln Cys Gln Lys Leu Leu Trp Gln Leu Asn Gly Arg
                485                 490                 495

Leu Glu Tyr Cys Leu Lys Asp Arg Met Asn Phe Asp Ile Pro Glu Glu
            500                 505                 510

Ile Lys Gln Leu Gln Gln Phe Gln Lys Glu Asp Ala Ala Leu Thr Ile
        515                 520                 525

Tyr Glu Met Leu Gln Asn Ile Phe Ala Ile Phe Arg Gln Asp Ser Ser
530                 535                 540

Ser Thr Gly Trp Asn Glu Thr Ile Val Glu Asn Leu Leu Ala Asn Val
545                 550                 555                 560

Tyr His Gln Ile Asn His Leu Lys Thr Val Leu Glu Glu Lys Leu Glu
                565                 570                 575

Lys Glu Asp Phe Thr Arg Gly Lys Leu Met Ser Ser Leu His Leu Lys
            580                 585                 590

Arg Tyr Tyr Gly Arg Ile Leu His Tyr Leu Lys Ala Lys Glu Tyr Ser
        595                 600                 605

His Cys Ala Trp Thr Ile Val Arg Val Glu Ile Leu Arg Asn Phe Tyr
610                 615                 620

Phe Ile Asn Arg Leu Thr Gly Tyr Leu Arg Asn
625                 630                 635
```

<210> SEQ ID NO 24
<211> LENGTH: 1905
<212> TYPE: DNA
<213> ORGANISM: Artificial Sequence
<220> FEATURE:
<223> OTHER INFORMATION: Synthetic polynucleotide

<400> SEQUENCE: 24

```
caggtgcagc tgaagcagag cggccccggc ctggtgcagc ccagccagag cctgagcatc     60
acctgcaccg tgagcggctt cagcctgacc aactacggcg tgcactgggt gcgccagagc    120
cccggcaagg gcctggagtg gctgggcgtg atctggagcg gcggcaacac cgactacaac    180
accccctcca ccagccgcct gagcatcaac aaggacaaca gcaagagcca ggtgttcttc    240
aagatgaaca gcctgcagag caacgacacc gccatctact actgcgcccg cgccctgacc    300
tactacgact acgagttcgc ctactggggc cagggcaccc tggtgaccgt gagcgccgcc    360
agcaccaagg gcccagcgt gttcccctg gccccagca gcaagagcac cagcggcggc    420
accgccgccc tgggctgcct ggtgaaggac tacttccccg agcccgtgac cgtgagctgg    480
aacagcggcg ccctgaccag cggcgtgcac accttccccg ccgtgctgca gagcagcggc    540
ctgtacagcc tgagcagcgt ggtgaccgtg cccagcagca gcctgggcac ccagacctac    600
atctgcaacg tgaaccacaa gcccagcaac accaaggtgg acaagcgcgt ggagcccaag    660
agctgcgata agacacacac ctgccctcca tgccccgcac ctgaactcct gggcgggcct    720
tccgttttcc tgtttcctcc caagcccaag gatacactga tgattagccg cacccccgaa    780
gtcacttgcg tggtggtgga tgtgagccat gaagatccag aagttaagtt taactggtat    840
gtggacgggg tcgaggtgca caatgctaaa acaaagccca gggaggagca atataactcc    900
acatacagag tggtgtccgt tctgacagtc ctgcaccagg actggctgaa cgggaaggaa    960
tacaagtgca aggtgtctaa taaggcactg ccagccccca tagagaagac aatctctaaa   1020
gctaaaggcc aaccacgcga gcctcaggtc tacacactgc caccatccag ggacgaactg   1080
accaagaatc aggtgagcct gacttgtctc gtcaaaggat tctacccaag cgacatcgcc   1140
gtggagtggg aatccaacgg ccaaccagag aacaactaca agaccacccc accagtcctg   1200
gactctgatg gagcttttt cctgtattcc aagctgacag tggacaagtc tcggtggcaa   1260
cagggcaacg tgttcagctg ctccgtgatg catgaagccc tgcataacca ctatacccag   1320
aaaagcctca gcctgtcccc cgggaaaagc ggcggcggcg gcagcggggg cggcggcagc   1380
ggaggaggcg gcagcggagg aggcggcatg agctacaact tgcttggatt cctacaaaga   1440
agcagcaatt ttcagtgtca gaagctcctg tggcaattga atgggaggct tgaatactgc   1500
ctcaaggaca ggatgaactt tgacatccct gaggagatta gcagctgca gcagttccag   1560
aaggaggacg ccgcattgac catctatgag atgctccaga catctttgc tattttcaga   1620
caagattcat ctagcactgg ctggaatgag actattgttg agaacctcct ggctaatgtc   1680
tatcatcaga taaaccatct gaagacagtc ctggaagaaa aactggagaa agaagatttc   1740
accaggggaa aactcatgag cagtctgcac ctgaaaagat attatgggag gattctgcat   1800
tacctgaagg ccaaggagta cagtcactgt gcctggacca tagtcagagt ggaaatccta   1860
aggaactttt acttcattaa cagacttaca ggttacctcc gaaac                   1905
```

<210> SEQ ID NO 25
<211> LENGTH: 641
<212> TYPE: PRT
<213> ORGANISM: Artificial Sequence
<220> FEATURE:
<223> OTHER INFORMATION: Synthetic polypeptide

<400> SEQUENCE: 25

```
Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
            35                  40                  45

Leu Glu Tyr Cys Leu Lys Asp Arg Met Asn Phe Asp Ile Pro Glu Glu
        50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Gly Ser Gly Gly Gly
            180                 185                 190

Gln Val Gln Leu Lys Gln Ser Gly Pro Gly Leu Val Gln Pro Ser Gln
            195                 200                 205

Ser Leu Ser Ile Thr Cys Thr Val Ser Gly Phe Ser Leu Thr Asn Tyr
        210                 215                 220

Gly Val His Trp Val Arg Gln Ser Pro Gly Lys Gly Leu Glu Trp Leu
225                 230                 235                 240

Gly Val Ile Trp Ser Gly Gly Asn Thr Asp Tyr Asn Thr Pro Phe Thr
                245                 250                 255

Ser Arg Leu Ser Ile Asn Lys Asp Asn Ser Lys Ser Gln Val Phe Phe
            260                 265                 270

Lys Met Asn Ser Leu Gln Ser Asn Asp Thr Ala Ile Tyr Tyr Cys Ala
        275                 280                 285

Arg Ala Leu Thr Tyr Tyr Asp Tyr Glu Phe Ala Tyr Trp Gly Gln Gly
        290                 295                 300

Thr Leu Val Thr Val Ser Ala Ala Ser Thr Lys Gly Pro Ser Val Phe
305                 310                 315                 320

Pro Leu Ala Pro Ser Ser Lys Ser Thr Ser Gly Gly Thr Ala Ala Leu
                325                 330                 335

Gly Cys Leu Val Lys Asp Tyr Phe Pro Glu Pro Val Thr Val Ser Trp
            340                 345                 350

Asn Ser Gly Ala Leu Thr Ser Gly Val His Thr Phe Pro Ala Val Leu
        355                 360                 365

Gln Ser Ser Gly Leu Tyr Ser Leu Ser Ser Val Val Thr Val Pro Ser
        370                 375                 380

Ser Ser Leu Gly Thr Gln Thr Tyr Ile Cys Asn Val Asn His Lys Pro
385                 390                 395                 400
```

Ser Asn Thr Lys Val Asp Lys Arg Val Glu Pro Lys Ser Cys Asp Lys
            405                 410                 415

Thr His Thr Cys Pro Pro Cys Pro Ala Pro Glu Leu Leu Gly Gly Pro
        420                 425                 430

Ser Val Phe Leu Phe Pro Pro Lys Pro Lys Asp Thr Leu Met Ile Ser
            435                 440                 445

Arg Thr Pro Glu Val Thr Cys Val Val Val Asp Val Ser His Glu Asp
450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
            485                 490                 495

Val Ser Val Leu Thr Val Leu His Gln Asp Trp Leu Asn Gly Lys Glu
            500                 505                 510

Tyr Lys Cys Lys Val Ser Asn Lys Ala Leu Pro Ala Pro Ile Glu Lys
        515                 520                 525

Thr Ile Ser Lys Ala Lys Gly Gln Pro Arg Glu Pro Gln Val Tyr Thr
    530                 535                 540

Leu Pro Pro Ser Arg Asp Glu Leu Thr Lys Asn Gln Val Ser Leu Thr
545                 550                 555                 560

Cys Leu Val Lys Gly Phe Tyr Pro Ser Asp Ile Ala Val Glu Trp Glu
                565                 570                 575

Ser Asn Gly Gln Pro Glu Asn Asn Tyr Lys Thr Thr Pro Pro Val Leu
            580                 585                 590

Asp Ser Asp Gly Ser Phe Phe Leu Tyr Ser Lys Leu Thr Val Asp Lys
        595                 600                 605

Ser Arg Trp Gln Gln Gly Asn Val Phe Ser Cys Ser Val Met His Glu
    610                 615                 620

Ala Leu His Asn His Tyr Thr Gln Lys Ser Leu Ser Leu Ser Pro Gly
625                 630                 635                 640

Lys

<210> SEQ ID NO 26
<211> LENGTH: 1923
<212> TYPE: DNA
<213> ORGANISM: Artificial Sequence
<220> FEATURE:
<223> OTHER INFORMATION: Synthetic polynucleotide

<400> SEQUENCE: 26
atgaccaaca agtgtctcct ccaaattgct ctcctgttgt gcttctccac tacagctctt      60
tccatgagct acaacttgct tggattccta caaagaagca gcaattttca gtgtcagaag     120
ctcctgtggc aattgaatgg gaggcttgaa tactgcctca aggacaggat gaactttgac     180
atccctgagg agattaagca gctgcagcag ttccagaagg aggacgccgc attgaccatc     240
tatgagatgc tccagaacat cttttgctatt ttcagacaag attcatctag cactggctgg     300
aatgagacta ttgttgagaa cctcctggct aatgtctatc atcagataaa ccatctgaag     360
acagtcctgg aagaaaaact ggagaaagaa gatttcacca gggaaaaact catgagcagt     420
ctgcacctga aagatatta tgggaggatt ctgcattacc tgaaggccaa ggagtacagt     480
cactgtgcct ggaccatagt cagagtggaa atcctaagga actttttactt cattaacaga     540 cttacaggtt acctccgaaa cggatccggt ggaggtcagg tgcagctgaa gcagagcggc     600
cccggcctgg tgcagcccag ccagagcctg agcatcacct gcaccgtgag cggcttcagc     660

```
ctgaccaact acggcgtgca ctgggtgcgc cagagccccg gcaagggcct ggagtggctg    720
ggcgtgatct ggagcggcgg caacaccgac tacaacaccc ccttcaccag ccgcctgagc    780
atcaacaagg acaacagcaa gagccaggtg ttcttcaaga tgaacagcct gcagagcaac    840
gacaccgcca tctactactg cgcccgcgcc ctgacctact acgactacga gttcgcctac    900
tggggccagg gcaccctggt gaccgtgagc gccgccagca ccaagggccc cagcgtgttc    960
cccctggccc ccagcagcaa gagcaccagc ggcggcaccg ccgccctggg ctgcctggtg   1020
aaggactact cccccgagcc cgtgaccgtg agctggaaca gcggcgccct gaccagcggc   1080
gtgcacacct tccccgccgt gctgcagagc agcggcctgt acagcctgag cagcgtggtg   1140
accgtgccca gcagcagcct gggcacccag acctacatct gcaacgtgaa ccacaagccc   1200
agcaacacca aggtggacaa gcgcgtggag cccaagagct gcgataagac acacacctgc   1260
cctccatgcc ccgcacctga actcctgggc gggccttccg ttttcctgtt tcctcccaag   1320
cccaaggata cactgatgat tagccgcacc cccgaagtca cttgcgtggt ggtggatgtg   1380
agccatgaag atccagaagt taagtttaac tggtatgtgg acggggtcga ggtgcacaat   1440
gctaaaacaa agcccaggga ggagcaatat aactccacat acagagtggt gtccgttctg   1500
acagtcctgc accaggactg gctgaacggg aaggaataca gtgcaaggt gtctaataag   1560 gcactgccag cccccataga gaagacaatc tctaaagcta aaggccaacc acgcgagcct   1620
caggtctaca cactgccacc atccagggac gaactgacca agaatcaggt gagcctgact   1680
tgtctcgtca aggattctac cccaagcgac atcgccgtgg agtgggaatc caacggccaa   1740
ccagagaaca actacaagac cacccccacca gtcctggact ctgatgggag cttttttcctg   1800 tattccaagc tgacagtgga caagtctcgg tggcaacagg gcaacgtgtt cagctgctcc   1860
gtgatgcatg aagccctgca taaccactat acccagaaaa gcctcagcct gtcccccggg   1920
aaa                                                                 1923
```

```
<210> SEQ ID NO 27
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 27

Gly Ser Gly Gly Gly
1               5

<210> SEQ ID NO 28
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 28

Ser Gly Gly Gly Gly Ser Gly Gly Gly Ser Gly Gly Gly Gly Ser
1               5                   10                  15

Gly Gly Gly Gly
            20

<210> SEQ ID NO 29
<211> LENGTH: 107
<212> TYPE: PRT
<213> ORGANISM: Artificial Sequence
```

```
<220> FEATURE:
<223> OTHER INFORMATION: Synthetic polypeptide

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 30
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 31
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 31

Arg Ala Ser Gln Asp Val Asn Thr Ala Val Ala
1               5                   10

<210> SEQ ID NO 32
<211> LENGTH: 7
<212> TYPE: PRT
<213> ORGANISM: Artificial Sequence
<220> FEATURE:
```

```
<223> OTHER INFORMATION: Synthetic polypeptide

<400> SEQUENCE: 32

Ser Ala Ser Phe Leu Tyr Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 33

Gln Gln His Tyr Thr Thr Pro Pro Thr
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 34

Asp Thr Tyr Ile His
1               5

<210> SEQ ID NO 35
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 35

Arg Ile Tyr Pro Thr Asn Gly Tyr Thr Arg Tyr Ala Asp Ser Val Lys
1               5                   10                  15

Gly

<210> SEQ ID NO 36
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 36

Trp Gly Gly Asp Gly Phe Tyr Ala Met Asp Tyr
1               5                   10

<210> SEQ ID NO 37
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 37

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45
```

```
Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 38
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 38

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 39
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 39

Arg Ala Ser Gln Ser Ile Gly Thr Asn Ile His
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 40

Tyr Ala Ser Glu Ser Ile Ser
1               5

<210> SEQ ID NO 41
<211> LENGTH: 9
<212> TYPE: PRT
<213> ORGANISM: Artificial Sequence
<220> FEATURE:
```

```
<223> OTHER INFORMATION: Synthetic polypeptide

<400> SEQUENCE: 41

Gln Gln Asn Asn Asn Trp Pro Thr Thr
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 42

Asn Tyr Gly Val His
1               5

<210> SEQ ID NO 43
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 43

Val Ile Trp Ser Gly Gly Asn Thr Asp Tyr Asn Thr Pro Phe Thr Ser
1               5                   10                  15

<210> SEQ ID NO 44
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 44

Ala Leu Thr Tyr Tyr Asp Tyr Glu Phe Ala Tyr
1               5                   10

<210> SEQ ID NO 45
<211> LENGTH: 330
<212> TYPE: PRT
<213> ORGANISM: Artificial Sequence
<220> FEATURE:
<223> OTHER INFORMATION: Synthetic polypeptide

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 326
<212> TYPE: PRT
<213> ORGANISM: Artificial Sequence
<220> FEATURE:
<223> OTHER INFORMATION: Synthetic polypeptide

<400> SEQUENCE: 46

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160
```

Val Glu Val His Asn Ala Lys Thr Lys Pro Arg Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 47
<211> LENGTH: 377
<212> TYPE: PRT
<213> ORGANISM: Artificial Sequence
<220> FEATURE:
<223> OTHER INFORMATION: Synthetic polypeptide

<400> SEQUENCE: 47

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

```
Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 48
<211> LENGTH: 327
<212> TYPE: PRT
<213> ORGANISM: Artificial Sequence
<220> FEATURE:
<223> OTHER INFORMATION: Synthetic polypeptide

<400> SEQUENCE: 48

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 49
<211> LENGTH: 402
<212> TYPE: PRT
<213> ORGANISM: Artificial Sequence
<220> FEATURE:
<223> OTHER INFORMATION: Synthetic polypeptide

<400> SEQUENCE: 49

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Gly Ser Asp
                165                 170                 175

Lys Thr His Thr Cys Pro Pro Cys Pro Ala Pro Glu Leu Leu Gly Gly
            180                 185                 190

Pro Ser Val Phe Leu Phe Pro Pro Lys Pro Lys Asp Thr Leu Met Ile
        195                 200                 205
```

Ser Arg Thr Pro Glu Val Thr Cys Val Val Val Asp Val Ser His Glu
        210                 215                 220

Asp Pro Glu Val Lys Phe Asn Trp Tyr Val Asp Gly Val Glu Val His
225                 230                 235                 240

Asn Ala Lys Thr Lys Pro Arg Glu Glu Gln Tyr Asn Ser Thr Tyr Arg
            245                 250                 255

Val Val Ser Val Leu Thr Val Leu His Gln Asp Trp Leu Asn Gly Lys
        260                 265                 270

Glu Tyr Lys Cys Lys Val Ser Asn Lys Ala Leu Pro Ala Pro Ile Glu
    275                 280                 285

Lys Thr Ile Ser Lys Ala Lys Gly Gln Pro Arg Glu Pro Gln Val Cys
290                 295                 300

Thr Leu Pro Pro Ser Arg Asp Glu Leu Thr Lys Asn Gln Val Ser Leu
305                 310                 315                 320

Ser Cys Ala Val Lys Gly Phe Tyr Pro Ser Asp Ile Ala Val Glu Trp
            325                 330                 335

Glu Ser Asn Gly Gln Pro Glu Asn Asn Tyr Lys Thr Thr Pro Pro Val
        340                 345                 350

Leu Asp Ser Asp Gly Ser Phe Phe Leu Val Ser Lys Leu Thr Val Asp
    355                 360                 365

Lys Ser Arg Trp Gln Gln Gly Asn Val Phe Ser Cys Ser Val Met His
370                 375                 380

Glu Ala Leu His Asn His Tyr Thr Gln Lys Ser Leu Ser Leu Ser Pro
385                 390                 395                 400

Gly Lys

<210> SEQ ID NO 50
<211> LENGTH: 1206
<212> TYPE: DNA
<213> ORGANISM: Artificial Sequence
<220> FEATURE:
<223> OTHER INFORMATION: Synthetic polynucleotide

<400> SEQUENCE: 50
agccccggcc agggcacaca gtccgagaac agctgcaccc actttcccgg caacctgcct      60
aacatgctga gggacctgag ggacgccttc agcagggtga agaccttctt ccagatgaag     120
gaccagctgg ataacctgct gctgaaggag agcctgctgg aggacttcaa gggctacctg     180
ggctgccagg ccctgagcga gatgatccag ttctacctgg aggaggtgat gccccaggcc     240
gagaaccagg accccgacat caaggcccac gtgaacagcc tgggcgagaa cctgaagacc     300
ctgaggctga ggctgaggag gtgccacagg ttcctgccct gtgagaacaa atccaaggcc     360
gtggagcagg tgaagaacgc cttcaacaag ctgcaggaaa agggcatcta caaggccatg     420
agcgagttcg acatctttat caactatatc gaggcctaca tgacaatgaa gatcaggaac     480
ggcggcggcg gcagcggggg cggcggcagc ggaggaggcg gcagcgacaa gacccacacc     540
tgcccccctt gccccgctcc ggagctgctg ggcggcccca gcgtgttcct gttcccccc      600 aagcccaagg acaccctgat gatcagccgc acccccgagg tgacctgcgt ggtggtggac     660
gtgagccacg aggaccccga ggtgaagttc aactggtacg tggacggcgt ggaggtgcac     720
aacgccaaga ccaagccccg cgaggagcag tacaacagca cctaccgcgt ggtgagcgtg     780
ctgaccgtgc tgcaccagga ctggctgaac ggcaaggagt acaagtgcaa ggtgagcaac     840
aaggccctgc ccgcccccat cgagaagacc atcagcaagg ccaagggcca gccccgcgag     900

```
cccccaggtgt gcaccctgcc ccccagccgc gacgagctga ccaagaacca ggtgagcctg    960
agctgcgccg tgaagggctt ctaccccagc gacatcgccg tggagtggga gagcaacggc   1020
cagcccgaga caactacaa gaccaccccc ccgtgctgg acagcgacgg cagcttcttc   1080
ctggtgagca agctgaccgt ggacaagagc cgctggcagc agggcaacgt gttcagctgc   1140
agcgtgatgc acgaggccct gcacaaccac tacacccaga gagcctgag cctgagcccc   1200 ggcaag                                                              1206
```

<210> SEQ ID NO 51
<211> LENGTH: 577
<212> TYPE: PRT
<213> ORGANISM: Artificial Sequence
<220> FEATURE:
<223> OTHER INFORMATION: Synthetic polypeptide

<400> SEQUENCE: 51

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Gly Ser Ser
                165                 170                 175

Pro Gly Gln Gly Thr Gln Ser Glu Asn Ser Cys Thr His Phe Pro Gly
            180                 185                 190

Asn Leu Pro Asn Met Leu Arg Asp Leu Arg Asp Ala Phe Ser Arg Val
        195                 200                 205

Lys Thr Phe Phe Gln Met Lys Asp Gln Leu Asp Asn Leu Leu Leu Lys
    210                 215                 220

Glu Ser Leu Leu Glu Asp Phe Lys Gly Tyr Leu Gly Cys Gln Ala Leu
225                 230                 235                 240

Ser Glu Met Ile Gln Phe Tyr Leu Glu Glu Val Met Pro Gln Ala Glu
                245                 250                 255

Asn Gln Asp Pro Asp Ile Lys Ala His Val Asn Ser Leu Gly Glu Asn
            260                 265                 270

Leu Lys Thr Leu Arg Leu Arg Leu Arg Arg Cys His Arg Phe Leu Pro
        275                 280                 285

Cys Glu Asn Lys Ser Lys Ala Val Glu Gln Val Lys Asn Ala Phe Asn
    290                 295                 300
```

```
Lys Leu Gln Glu Lys Gly Ile Tyr Lys Ala Met Ser Glu Phe Asp Ile
305                 310                 315                 320

Phe Ile Asn Tyr Ile Glu Ala Tyr Met Thr Met Lys Ile Arg Asn Gly
            325                 330                 335

Gly Gly Gly Ser Gly Gly Gly Ser Gly Gly Gly Ser Asp Lys
            340                 345                 350

Thr His Thr Cys Pro Pro Cys Pro Ala Pro Glu Leu Leu Gly Gly Pro
            355                 360                 365

Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
    435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Cys Thr
465                 470                 475                 480

Leu Pro Pro Ser Arg Asp Glu Leu Thr Lys Asn Gln Val Ser Leu Ser
                485                 490                 495

Cys Ala Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
    515                 520                 525

Asp Ser Asp Gly Ser Phe Phe Leu Val Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 52
<211> LENGTH: 1731
<212> TYPE: DNA
<213> ORGANISM: Artificial Sequence
<220> FEATURE:
<223> OTHER INFORMATION: Synthetic polynucleotide

<400> SEQUENCE: 52
agccccggcc agggcacaca gtccgagaac agctgcaccc actttcccgg caacctgcct      60
aacatgctga gggacctgag ggacgccttc agcagggtga agaccttctt ccagatgaag     120
gaccagctgg ataacctgct gctgaaggag agcctgctgg aggacttcaa gggctacctg     180
ggctgccagg ccctgagcga gatgatccag ttctacctgg aggaggtgat gccccaggcc     240
gagaaccagg accccgacat caaggcccac gtgaacagcc tgggcgagaa cctgaagacc     300
ctgaggctga ggctgaggag gtgccacagg ttcctgccct gtgagaacaa atccaaggcc     360
gtggagcagg tgaagaacgc cttcaacaag ctgcaggaaa agggcatcta caaggccatg     420
agcgagttcg acatctttat caactatatc gaggcctaca tgacaatgaa gatcaggaac     480
```

```
ggcggcggcg gcagcggggg cggcggcagc ggaggaggcg gcagcagccc cggccagggc      540
acacagtccg agaacagctg cacccacttt cccggcaacc tgcctaacat gctgagggac      600
ctgagggacg ccttcagcag ggtgaagacc ttcttccaga tgaaggacca gctggataac      660
ctgctgctga aggagagcct gctggaggac ttcaagggct acctgggctg ccaggccctg      720
agcgagatga tccagttcta cctggaggag gtgatgcccc aggccgagaa ccaggacccc      780
gacatcaagg cccacgtgaa cagcctgggc gagaacctga gaccctgag gctgaggctg      840 aggaggtgcc acaggttcct gccctgtgag aacaaatcca aggccgtgga gcaggtgaag      900
aacgccttca caagctgca ggaaaagggc atctacaagg ccatgagcga gttcgacatc      960
tttatcaact atatcgaggc ctacatgaca atgaagatca ggaacggcgg cggcggcagc     1020
gggggcggcg gcagcggagg aggcggcagc gacaagaccc acacctgccc ccccttgcccc     1080 gctccggagc tgctgggcgg ccccagcgtg ttcctgttcc cccccaagcc caaggacacc     1140
ctgatgatca gccgcacccc cgaggtgacc tgcgtggtgg tggacgtgag ccacgaggac     1200
cccgaggtga agttcaactg gtacgtggac ggcgtggagg tgcacaacgc caagaccaag     1260
ccccgcgagg agcagtacaa cagcacctac cgcgtggtga gcgtgctgac cgtgctgcac     1320
caggactggc tgaacggcaa ggagtacaag tgcaaggtga gcaacaaggc cctgccccgc     1380
cccatcgaga agaccatcag caaggccaag ggccagcccc gcgagcccca ggtgtgcacc     1440
ctgcccccca gccgcgacga gctgaccaag aaccaggtga gcctgagctg cgccgtgaag     1500
ggcttctacc ccagcgacat cgccgtggag tgggagagca acggccagcc cgagaacaac     1560
tacaagacca cccccccgt gctggacagc gacggcagct tcttcctggt gagcaagctg     1620
accgtggaca gagccgctg gcagcagggc aacgtgttca gctgcagcgt gatgcacgag     1680
gccctgcaca accactacac ccagaagagc ctgagcctga gccccggcaa g              1731
```

<210> SEQ ID NO 53
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 54
<211> LENGTH: 1347
<212> TYPE: DNA
<213> ORGANISM: Artificial Sequence
<220> FEATURE:
<223> OTHER INFORMATION: Synthetic polynucleotide

<400> SEQUENCE: 54
gaggtgcagc tggtggagag cggcggcggc ctggtgcagc ccggcggcag cctgcgcctg      60
agctgcgccg ccagcggctt caccttcacc gactacacca tggactgggt gcgccaggcc     120
cccggcaagg gcctggagtg ggtggccgac gtgaacccca cagcggcgg cagcatctac      180 aaccagcgct tcaagggccg cttcaccctg agcgtggacc gcagcaagaa cacccctgtac    240 ctgcagatga acagcctgcg cgccgaggac accgccgtgt actactgcgc cgcaacctg      300
```

```
ggccccagct tctacttcga ctactggggc cagggcaccc tggtgaccgt gagcagcgcc    360
agcaccaagg gcccagcgt gttccccctg gccccagca gcaagagcac cagcggcggc      420
accgccgccc tgggctgcct ggtgaaggac tacttccccg agcccgtgac cgtgagctgg    480
aacagcggcg ccctgaccag cggcgtgcac accttcccg ccgtgctgca gagcagcggc     540
ctgtacagcc tgagcagcgt ggtgaccgtg cccagcagca gcctgggcac ccagacctac    600
atctgcaacg tgaaccacaa gcccagcaac accaaggtgg acaagcgcgt ggagcccaag    660
agctgcgaca gacccacac ctgcccccc tgccccgcc ccgagctgct gggcggcccc       720
agcgtgttcc tgttccccc caagcccaag gacaccctga tgatcagccg cacccccgag     780
gtgacctgcg tggtggtgga cgtgagccac gaggaccccg aggtgaagtt caactggtac    840
gtggacggcg tggaggtgca acgccaag accaagcccc gcgaggagca gtacaacagc      900
acctaccgcg tggtgagcgt gctgaccgtg ctgcaccagg actggctgaa cggcaaggag    960
tacaagtgca aggtgagcaa caaggccctg cccgccccca tcgagaagac catcagcaag   1020
gccaagggcc agccccgcga gccccaggtg tacaccctgc cccctgccg cgacgagctg    1080 accaagaacc aggtgagcct gtggtgcctg gtgaagggct tctacccag cgacatcgcc    1140 gtggagtggg agagcaacgg ccagcccgag aacaactaca agaccacccc cccgtgctg    1200 gacagcgacg gcagcttctt cctgtacagc aagctgaccg tggacaagag ccgctggcag   1260
cagggcaacg tgttcagctg cagcgtgatg cacgaggccc tgcacaacca ctacacccag   1320
aagagcctga gcctgagccc cggcaag                                       1347
```

<210> SEQ ID NO 55
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

-continued

```
Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 56
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 56

```
gacatccaga tgacccagag ccccagcagc ctgagcgcca gcgtgggcga ccgcgtgacc      60
atcacctgca aggccagcca ggacgtgagc atcggcgtgg cctggtacca gcagaagccc     120
ggcaaggccc ccaagctgct gatctacagc gccagctacc gctacaccgg cgtgcccagc     180
cgcttcagcg gcagcggcag cggcaccgac ttcaccctga ccatcagcag cctgcagccc     240
gaggacttcg ccacctacta ctgccagcag tactacatct accccctcac cttcggccag     300
ggcaccaagg tggagatcaa gcgcaccgtg gccgccccca gcgtgttcat cttcccccc      360 agcgacgagc agctgaagag cggcaccgcc agcgtggtgt gcctgctgaa caacttctac     420
ccccgcgagg ccaaggtgca gtggaaggtg gacaacgccc tgcagagcgg caacagccag     480
gagagcgtga ccgagcagga cagcaaggac agcacctaca gcctgagcag cacccctgacc    540 ctgagcaagg ccgactacga aagcacaag gtgtacgcct gcgaggtgac ccaccagggc      600
ctgagcagcc ccgtgaccaa gagcttcaac cgcggcgagt gc                        642
```

<210> SEQ ID NO 57
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 57

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Thr Asp Tyr
        20                  25                  30

Thr Met Asp Trp Val Arg Gln Ala Pro Gly Lys Gly Leu Glu Trp Val
    35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 58
<211> LENGTH: 107
<212> TYPE: PRT

```
<213> ORGANISM: Artificial Sequence
<220> FEATURE:
<223> OTHER INFORMATION: Synthetic polypeptide

<400> SEQUENCE: 58

Asp Ile Gln Met Thr Gln Ser Pro Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 59
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 59

Asp Tyr Thr Met Asp
1               5

<210> SEQ ID NO 60
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 60

Asp Val Asn Pro Asn Ser Gly Gly Ser Ile Tyr Asn Gln Arg Phe Lys
1               5                   10                  15

Gly

<210> SEQ ID NO 61
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 61

Asn Leu Gly Pro Ser Phe Tyr Phe Asp Tyr
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 62

Lys Ala Ser Gln Asp Val Ser Ile Gly Val Ala
```

```
<210> SEQ ID NO 63
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 63

Ser Ala Ser Tyr Arg Tyr Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 64

Gln Gln Tyr Tyr Ile Tyr Pro Tyr Thr
1               5

<210> SEQ ID NO 65
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 65

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
                20                  25                  30

Ile Gly Trp Leu Gln Gln Arg Pro Gly Lys Ser Phe Lys Gly Leu Ile
            35                  40                  45

Tyr His Gly Thr Asn Leu Asp Asp Glu Val Pro Ser Arg Phe Ser Gly
        50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 66
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 66

```
gacatcctga tgacccagag ccccagcagc atgagcgtga gcctgggcga caccgtgagc      60
atcacctgcc acagcagcca ggacatcaac agcaacatcg ctggctgca gcagcgcccc     120 ggcaagagct tcaagggcct gatctaccac ggcaccaacc tggacgacga ggtgcccagc    180
cgcttcagcg gcagcggcag cggcgccgac tacagcctga ccatcagcag cctggagagc    240
gaggacttcg ccgactacta ctgcgtgcag tacgcccagt cccctggac cttcggcggc    300 ggcaccaagc tggagatcaa gcgcaccgtg gccgccccca gcgtgttcat cttccccccc    360
agcgacgagc agctgaagag cggcaccgcc agcgtggtgt gcctgctgaa caacttctac    420
ccccgcgagg ccaaggtgca gtggaaggtg acaacgccc tgcagagcgg caacagccag    480
gagagcgtga ccgagcagga cagcaaggac agcacctaca gcctgagcag caccctgacc    540
ctgagcaagg ccgactacga aagcacaag gtgtacgcct gcgaggtgac ccaccagggc    600
ctgagcagcc ccgtgaccaa gagcttcaac cgcggcgagt gc                       642
```

<210> SEQ ID NO 67
<211> LENGTH: 446
<212> TYPE: PRT
<213> ORGANISM: Artificial Sequence
<220> FEATURE:
<223> OTHER INFORMATION: Synthetic polypeptide

<400> SEQUENCE: 67

```
Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
    355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
    435                 440                 445
```

<210> SEQ ID NO 68
<211> LENGTH: 1338
<212> TYPE: DNA
<213> ORGANISM: Artificial Sequence
<220> FEATURE:
<223> OTHER INFORMATION: Synthetic polynucleotide

<400> SEQUENCE: 68

```
gacgtgcagc tgcaggagag cggccccagc ctggtgaagc ccagccagag cctgagcctg      60
acctgcaccg tgaccggcta cagcatcacc agcgacttcg cctggaactg gatccgccag     120
ttccccggca acaagctgga gtggatgggc tacatcagct acagcggcaa cacccgctac     180
aaccccagcc tgaagagccg catcagcatc acccgcgaca ccagcaagaa ccagttcttc     240
ctgcagctga acagcgtgac catcgaggac accgccacct actactgcgt gaccgccggc     300
cgcggcttcc cctactgggg ccagggcacc ctggtgaccg tgagcgccgc cagcaccaag     360
ggccccagcg tgttcccccct ggcccccagc agcaagagca ccagcggcgg caccgccgcc     420
ctgggctgcc tggtgaagga ctacttcccc gagcccgtga ccgtgagctg gaacagcggc     480
gccctgacca gcggcgtgca caccttcccc gccgtgctgc agagcagcgg cctgtacagc     540
ctgagcagcg tggtgaccgt gcccagcagc agcctgggca cccagaccta catctgcaac     600
gtgaaccaca gcccagcaa caccaaggtg gacaagcgcg tggagcccaa gagctgcgac     660
```

```
aagacccaca cctgccccc ctgccccgcc cccgagctgc tgggcggccc cagcgtgttc    720
ctgttccccc ccaagcccaa ggacaccctg atgatcagcc gcaccccga ggtgacctgc    780 gtggtggtgg acgtgagcca cgaggacccc gaggtgaagt tcaactggta cgtggacggc    840
gtggaggtgc acaacgccaa gaccaagccc cgcgaggagc agtacaacag cacctaccgc    900
gtggtgagcg tgctgaccgt gctgcaccag gactggctga acggcaagga gtacaagtgc    960
aaggtgagca caaggccct gcccgccccc atcgagaaga ccatcagcaa ggccaagggc    1020
cagccccgcg agccccaggt gtacaccctg ccccctgcc gcgacgagct gaccaagaac    1080
caggtgagcc tgtggtgcct ggtgaagggc ttctacccca gcgacatcgc cgtggagtgg    1140
gagagcaacg gccagcccga gaacaactac aagaccaccc ccccgtgct ggacagcgac    1200 ggcagcttct tcctgtacag caagctgacc gtggacaaga gccgctggca gcagggcaac    1260
gtgttcagct gcagcgtgat gcacgaggcc ctgcacaacc actacaccca gaagagcctg    1320
agcctgagcc ccggcaag                                                  1338
```

```
<210> SEQ ID NO 69
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 69

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys
            100                 105
```

```
<210> SEQ ID NO 70
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 70

Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
```

```
                65                  70                  75                  80
Leu Gln Leu Asn Ser Val Thr Ile Glu Asp Thr Ala Thr Tyr Tyr Cys
                    85                  90                  95

Val Thr Ala Gly Arg Gly Phe Pro Tyr Trp Gly Gln Gly Thr Leu Val
            100                 105                 110

Thr Val Ser Ala
        115

<210> SEQ ID NO 71
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 71

His Ser Ser Gln Asp Ile Asn Ser Asn Ile Gly
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 72

His Gly Thr Asn Leu Asp Asp
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 73

Val Gln Tyr Ala Gln Phe Pro Trp Thr
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 74

Ser Asp Phe Ala Trp Asn
1               5

<210> SEQ ID NO 75
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 75

Tyr Ile Ser Tyr Ser Gly Asn Thr Arg Tyr Asn Pro Ser Leu Lys Ser
1               5                   10                  15

<210> SEQ ID NO 76
<211> LENGTH: 7
```

```
<212> TYPE: PRT
<213> ORGANISM: Artificial Sequence
<220> FEATURE:
<223> OTHER INFORMATION: Synthetic polypeptide

<400> SEQUENCE: 76

Ala Gly Arg Gly Phe Pro Tyr
1               5

<210> SEQ ID NO 77
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 77

Gly Gly Gly Gly Ser Gly Gly Gly Gly Ser Gly Gly Gly Gly Ser
1               5                   10                  15

<210> SEQ ID NO 78
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 78

Gly Gly Gly Gly Ser
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 79

Gly Ala Pro Gly Gly
1               5
```